US009958776B2

(12) United States Patent
Hatakeyama et al.

(10) Patent No.: US 9,958,776 B2
(45) Date of Patent: May 1, 2018

(54) RESIST COMPOSITION AND PATTERNING PROCESS

(71) Applicant: SHIN-ETSU CHEMICAL CO., LTD., Tokyo (JP)

(72) Inventors: Jun Hatakeyama, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days. days.

(21) Appl. No.: 15/390,855

(22) Filed: Dec. 27, 2016

(65) Prior Publication Data
US 2017/0184964 A1   Jun. 29, 2017

(30) Foreign Application Priority Data

Dec. 28, 2015 (JP) .................................. 2015-256346
Jul. 7, 2016 (JP) .................................. 2016-135025

(51) Int. Cl.
| G03F 7/004 | (2006.01) |
| G03F 7/039 | (2006.01) |
| G03F 7/038 | (2006.01) |
| G03F 7/16 | (2006.01) |
| G03F 7/38 | (2006.01) |
| G03F 7/20 | (2006.01) |
| G03F 7/32 | (2006.01) |
| C07F 9/06 | (2006.01) |
| C07C 211/62 | (2006.01) |
| C07C 211/63 | (2006.01) |

(52) U.S. Cl.
CPC .......... *G03F 7/0045* (2013.01); *C07C 211/62* (2013.01); *C07C 211/63* (2013.01); *C07F 9/065* (2013.01); *C07F 9/067* (2013.01); *G03F 7/0382* (2013.01); *G03F 7/0397* (2013.01); *G03F 7/162* (2013.01); *G03F 7/168* (2013.01); *G03F 7/2004* (2013.01); *G03F 7/2006* (2013.01); *G03F 7/2037* (2013.01); *G03F 7/2041* (2013.01); *G03F 7/322* (2013.01); *G03F 7/38* (2013.01)

(58) Field of Classification Search
CPC .......... G03F 7/004; G03F 7/32; G03F 7/2037; G03F 7/0045; G03F 7/0382; G03F 7/0397; G03F 7/2004; G03F 7/2006; C07C 211/62; C07C 211/63; C07F 9/065; C07F 9/062; C07F 9/067
USPC ..... 430/270.1, 942, 322, 325, 329; 558/392; 568/9
See application file for complete search history.

(56) References Cited

U.S. PATENT DOCUMENTS

| 6,673,511 | B1 | 1/2004 | Hatakeyama et al. |
| 6,749,988 | B2 | 6/2004 | Hatakeyama et al. |
| 6,916,593 | B2 | 7/2005 | Hatakeyama et al. |
| 6,936,684 | B2* | 8/2005 | Nobori ..................... C07F 9/065 524/706 |
| 9,250,518 | B2 | 2/2016 | Hatakeyama et al. |
| 9,651,863 | B2* | 5/2017 | Takizawa .............. C08F 212/14 |
| 2005/0181300 | A1* | 8/2005 | Okazaki ............... C07D 487/04 430/270.1 |
| 2011/0028585 | A1* | 2/2011 | Shiraishi ............... C07C 211/63 522/63 |
| 2013/0155381 | A1* | 6/2013 | Chang ................... G03F 7/0045 355/27 |
| 2014/0030654 | A1* | 1/2014 | Masuyama ............... G03F 7/20 430/281.1 |
| 2015/0004533 | A1* | 1/2015 | Hirano ................. C07D 235/12 430/18 |
| 2015/0017576 | A1* | 1/2015 | Inoue ........................ G03F 7/38 430/9 |
| 2015/0147688 | A1* | 5/2015 | Yokokawa ............ G03F 7/0392 430/18 |
| 2016/0009737 | A1* | 1/2016 | Ikeda .................... C07D 487/04 430/17 |
| 2016/0062232 | A1* | 3/2016 | Hong .................. H01L 21/0273 430/325 |
| 2016/0299429 | A1* | 10/2016 | Ikeda .................... C07C 279/04 |

FOREIGN PATENT DOCUMENTS

| JP | 2001-194776 A | 7/2001 |
| JP | 2002-226470 A | 8/2002 |
| JP | 2002-363148 A | 12/2002 |
| JP | 2010-84144 A | 4/2010 |
| JP | 2011236416 A | * 11/2011 |
| JP | 2012237776 A | * 12/2012 |
| JP | 2014098118 A | * 5/2014 |
| JP | 2015-90382 A | 5/2015 |
| WO | 2015/111640 A1 | 7/2015 |

OTHER PUBLICATIONS

Machine translation of JP 2012-237776 (no date).*
Machine translation of JP 2011-236416 (no date).*
Machine translation of JP 2014-098118 (no date).*
Machine translation of JP 2010-084144 (no date).*
Hinsberg et al., "Extendibility of Chemically Amplified Resists: Another Brick Wall?", Proceedings of SPIE, vol. 5039, pp. 1-14, (2003).
Kishikawa et al., "Assessment of trade-off between resist resolution ans sensitivity for optimization of hyper-NA immersion lithography", Proceedings of SPIE, vol. 6520, pp. 65203L-1-65203L-9, (2007).
Wang et al., "Photobase generator and photo decomposable quencher for high-resolution photoresist applications", Proceedings of SPIE, vol. 7639, pp. 76390W-1-76390W-15, (2010).

* cited by examiner

*Primary Examiner* — Amanda C Walke
(74) *Attorney, Agent, or Firm* — Westerman, Hattori, Daniels & Adrian, LLP

(57) ABSTRACT

A resist composition comprising a base polymer and a phosphazene salt compound offers a high dissolution contrast, minimal LWR, and dimensional stability on PPD.

20 Claims, No Drawings

RESIST COMPOSITION AND PATTERNING PROCESS

CROSS-REFERENCE TO RELATED APPLICATION

This non-provisional application claims priority under 35 U.S.C. § 119(a) on Patent Application Nos. 2015-256346 and 2016-135025 filed in Japan on Dec. 28, 2015 and Jul. 7, 2016, respectively, the entire contents of which are hereby incorporated by reference.

TECHNICAL FIELD

This invention relates to a resist composition comprising a phosphazene salt compound and a pattern forming process.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, EUV lithography of wavelength 13.5 nm, and double patterning version of the ArF lithography, on which active research efforts have been made.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein crosslinking reaction takes place under the action of acid. Quenchers are often added to these resist compositions for the purpose of suppressing the diffusion of the acid to unexposed areas to improve the contrast. The addition of quenchers is fully effective to this purpose. A number of amine quenchers were proposed as disclosed in Patent Documents 1 to 3.

As the pattern feature size is reduced, approaching to the diffraction limit of light, light contrast lowers. In the case of positive resist film, a lowering of light contrast leads to reductions of resolution and focus margin of hole and trench patterns.

For mitigating the influence of reduced resolution of resist pattern due to a lowering of light contrast, an attempt is made to enhance the dissolution contrast of resist film. Another attempt is also made to control acid diffusion which causes image blurs to resist patterns.

There is known a chemically amplified resist material utilizing an acid amplifying mechanism that a compound is decomposed with an acid to generate another acid. In general, the concentration of acid creeps up linearly with an increase of exposure dose. In the case of the acid amplifying mechanism, the concentration of acid jumps up non-linearly as the exposure dose increases. The acid amplifying system is beneficial for further enhancing the advantages of chemically amplified resist film including high contrast and high sensitivity, but worsens the drawbacks of chemically amplified resist film that environmental resistance is degraded by amine contamination and maximum resolution is reduced by an increase of acid diffusion distance. The acid amplifying system is very difficult to control when implemented in practice.

Another approach for enhanced contrast is by reducing the concentration of amine with an increasing exposure dose. This may be achieved by applying a compound which loses the quencher function upon light exposure.

With respect to the acid labile group used in (meth) acrylate polymers for the ArF lithography, deprotection reaction takes place when a photoacid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher.

Further, the sulfonium or iodonium salt capable of generating an α-non-fluorinated sulfonic acid also functions as a photodegradable quencher since it loses the quencher function by photodegradation. Non-Patent Document 3 points out that the addition of a photodegradable quencher expands the margin of a trench pattern although the structural formula is not illustrated. However, it has only a little influence on performance improvement. There is a desire to have a quencher for further improving contrast.

Patent Document 4 discloses a quencher of onium salt type which reduces its basicity through a mechanism that it generates an amino-containing carboxylic acid upon light exposure, which in turn forms a lactam in the presence of acid. Due to the mechanism that basicity is reduced under the action of acid, acid diffusion is controlled by high basicity in the unexposed region where the amount of acid generated is minimal, whereas acid diffusion is promoted due to reduced basicity of the quencher in the overexposed region where the amount of acid generated is large. This expands the difference in acid amount between the exposed and unexposed regions, from which an improvement in contrast is expected. However, this method has the drawback of increased acid diffusion.

Biguanide and phosphazene compounds are known as superstrong base compounds. Since they have a higher basicity than diazabicycloundecene (DBU), their use as a catalyst for curing reaction of epoxy compounds is under study. For example, Patent Documents 5 and 6 disclose base generators capable of generating guanidine, biguanide, phosphazene, and 2,5,8,9-tetraaza-1-phosphabicyclo[3.3.3] undecane compounds upon light exposure. In general, the amount of acid generated by a photoacid generator increases as the exposure dose is increased. In a system where a photoacid generator and a photobase generator coexist with the amounts and generation efficiencies of PAG and PBG being equal, the amount of generated acid does not increase even when the exposure dose is increased. If the amount and generation efficiency of PAG are great, the amount of acid increases as the exposure dose is increased, but that increase is yet insufficient and so the contrast of resist is low.

Attention is now paid to the negative tone pattern forming process via organic solvent development. In an attempt to form a hole pattern by light exposure, a hole pattern having the minimum pitch can be formed by a combination of a bright-pattern mask with a negative tone resist. There is the problem that the pattern as developed varies in size due to a lapse of time, known as post exposure bake to development delay (PEBDD) or post PEB delay (PPD). The reason is that during storage of the resist film at room temperature after PEB, the acid gradually diffuses into the unexposed region where deprotection reaction takes place. One solution to the PPD problem is to use a protective group having a high level of activation energy and to effect PEB at high temperature. Since PPD is a reaction at room temperature, the influence of PPD is mitigated as the temperature gap between PEB and PPD is greater. Use of an acid generator capable of generating an acid having a bulky anion is also effective for mitigating the influence of PPD. While a proton serving as acid pairs with an anion, the hopping of proton is reduced as the size of anion becomes larger.

Another component that is expected effective for mitigating the influence of PPD is a quencher. Conventional quenchers were developed for the purpose of suppressing acid diffusion during PEB at high temperature for thereby enhancing the contrast of deprotection reaction. For mitigating the influence of PPD, it is desired from a different viewpoint to develop a quencher capable of suppressing acid diffusion at room temperature.

CITATION LIST

Patent Document 1: JP-A 2001-194776
Patent Document 2: JP-A 2002-226470
Patent Document 3: JP-A 2002-363148
Patent Document 4: JP-A 2015-090382
Patent Document 5: JP-A 2010-084144
Patent Document 6: WO 2015/111640
Non-Patent Document 1: SPIE Vol. 5039 p 1 (2003)
Non-Patent Document 2: SPIE Vol. 6520 p 65203L-1 (2007)
Non-Patent Document 3: SPIE Vol. 7639 p 76390W (2010)

DISCLOSURE OF INVENTION

As alluded to above, the addition of quenchers is effective for mitigating the influence of PPD. In the case of base generators capable of generating superstrong bases as disclosed in Patent Documents 5 and 6, the site where a base is generated is in the exposed region. When a resist film is allowed to stand at room temperature after PEB, acid diffusion takes place within the resist film from the exposed region to the unexposed region. In this situation, the quencher based on the mechanism that a base is generated only in the exposed region fails to prevent acid diffusion from the exposed region to the unexposed region.

Such quenchers as amine quenchers and sulfonium and iodonium salts of sulfonic acid and carboxylic acid have a high basicity and are fully effective for suppressing acid diffusion in the unexposed region, but their performance is still unsatisfactory. Desired are quenchers capable of suppressing acid diffusion at room temperature, providing a high dissolution contrast, and reducing edge roughness (LWR) rather than these quenchers.

An object of the invention is to provide a resist composition which exhibits a high dissolution contrast, a reduced LWR, and no dimensional changes on PPD, independent of whether it is of positive tone or negative tone; and a pattern forming process using the same.

The inventors have found that using a specific phosphazene salt compound as the quencher, a resist film having a reduced LWR, a high dissolution contrast, and no dimensional changes on PPD is obtainable.

In one aspect, the invention provides a resist composition comprising a base polymer and a phosphazene salt compound having the formula (A).

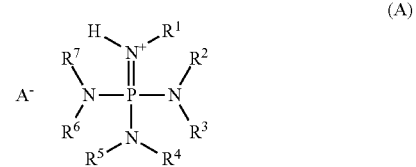

(A)

Herein $R^1$ to $R^7$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, which may contain an ester, ether, sulfide, sulfoxide, carbonate, carbamate, sulfone, halogen, amino, amide, hydroxy, thiol or nitro moiety, a pair of $R^1$ and $R^2$, $R^2$ and $R^3$, $R^3$ and $R^4$, $R^4$ and $R^5$, $R^5$ and $R^6$, or $R^6$ and $R^7$ may bond together to form a ring, or a pair of $R^2$ and $R^3$, $R^4$ and $R^5$, or $R^6$ and taken together, may form a double bond or a group having the formula (A)-1, $R^1$ may be a group having the formula (A)-2,

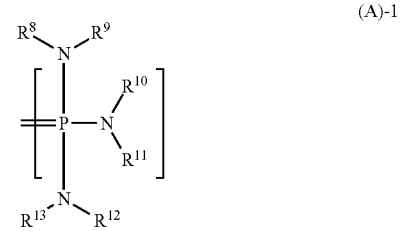

(A)-1

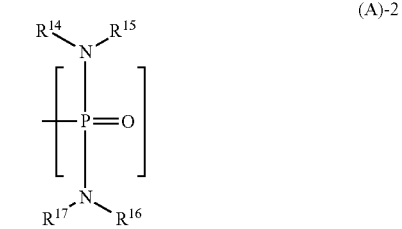

(A)-2 wherein $R^8$ to $R^{17}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{29}$ aryl group, a pair of $R^8$ and $R^9$, $R^9$ and $R^{10}$, $R^{10}$ and $R^{11}$, $R^{11}$ and $R^{12}$, $R^{12}$ and $R^{13}$, $R^{14}$ and $R^{15}$, or $R^{16}$ and $R^{17}$ may bond together to form a ring, or a pair of $R^8$ and $R^9$, $R^{10}$ and $R^{11}$, or $R^{12}$ and $R^{13}$, taken together, may form a double bond or a group having the formula (A)-1. $A^-$ is an anion selected from the group consisting of hydroxide, chloride, bromide, iodide, nitrate, nitrite, chlorate, chlorite, perchlorate, hydrogencarbonate, dihydrogenphosphate, hydrogensulfate, thiocyanate, hydrogenoxalate, cyanide, iodate ions, and anions of the formulae (M-1) and (M-2):

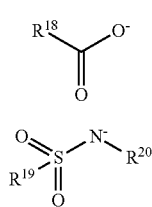

(M)-1

(M)-2 wherein $R^{18}$ is hydrogen, or a $C_1$-$C_{30}$ straight, branched or cyclic alkyl group, $C_2$-$C_{30}$ straight, branched or cyclic alkenyl group, $C_2$-$C_{30}$ straight, branched or cyclic alkynyl group, $C_6$-$C_{20}$ aryl group, $C_7$-$C_{20}$ aralkyl group, or $C_3$-$C_{20}$ aromatic or aliphatic heterocycle-containing group, which may contain an ester, ether, sulfide, sulfoxide, carbonate, carbamate, sulfone, halogen, amino, amide, hydroxy, thiol or nitro moiety, with the proviso that $R^{18}$ does not contain a group of the formula (A)-3:

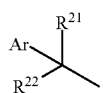

(A)-3 wherein Ar is a $C_6$-$C_{16}$ aromatic group, $R^{21}$ and $R^{22}$ are each independently hydrogen, hydroxy, alkoxy, $C_1$-$C_6$ straight, branched or cyclic alkyl group, or $C_6$-$C_{10}$ aryl group, $R^{19}$ is fluorine, or a $C_1$-$C_{10}$ straight, branched or cyclic fluoroalkyl group or fluorophenyl group, which may contain a hydroxy, ether, ester or alkoxy moiety, $R^{20}$ is hydrogen, or a $C_1$-$C_{10}$ straight, branched or cyclic alkyl group, $C_2$-$C_{10}$ straight, branched or cyclic alkenyl group, $C_2$-$C_{10}$ straight or branched alkynyl group, or $C_6$-$C_{10}$ aryl group, which may contain a hydroxy, ether, ester or alkoxy moiety.

In a preferred embodiment, the resist composition may further comprise an acid generator capable of generating sulfonic acid, sulfonimide or sulfonmethide, and/or an organic solvent.

In a preferred embodiment, the base polymer comprises recurring units having the formula (a1) or recurring units having the formula (a2).

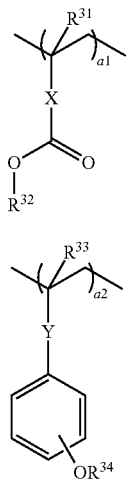

(a1)

(a2)

Herein $R^{31}$ and $R^{33}$ are each independently hydrogen or methyl, $R^{32}$ and $R^{34}$ are each independently an acid labile group, X is a single bond, ester group, phenylene group, naphthylene group or a $C_1$-$C_{12}$ linking group containing lactone ring, and Y is a single bond or ester group.

In a preferred embodiment, the resist composition may further comprise a dissolution inhibitor. Typically the resist composition is a chemically amplified positive resist composition.

In another preferred embodiment, the base polymer is free of an acid labile group; the resist composition may further comprise a crosslinker. Typically the resist composition is a chemically amplified negative resist composition.

In a preferred embodiment, the base polymer further comprises recurring units of at least one type selected from the formulae (f1) to (f3).

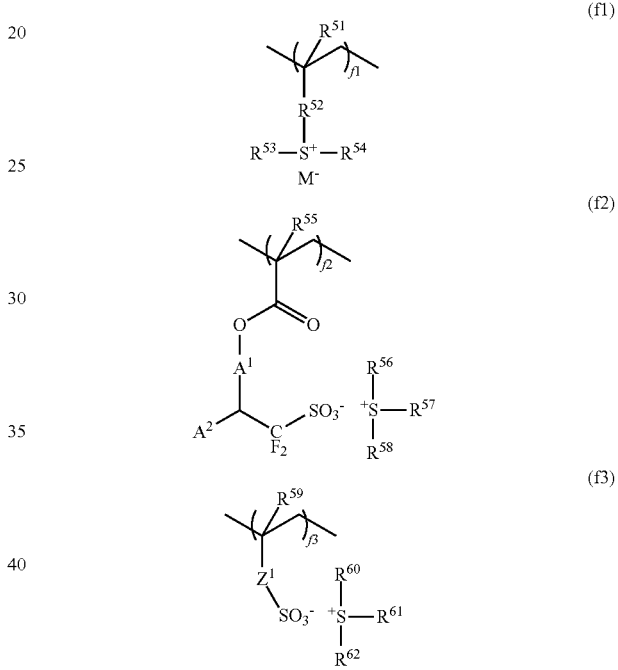

(f1)

(f2)

(f3)

Herein $R^{51}$, $R^{55}$ and $R^{59}$ each are hydrogen or methyl; $R^{52}$ is a single bond, phenylene, —O—$R^{63}$—, or —C(=O)—$Y^1$—$R^{63}$—, $Y^1$ is —O— or —NH—, $R^{63}$ is a $C_1$-$C_6$ straight, branched or cyclic alkylene or alkenylene group which may contain a carbonyl, ester, ether or hydroxyl moiety, or phenylene group; $R^{53}$, $R^{54}$, $R^{56}$, $R^{57}$, $R^{58}$, $R^{60}$, $R^{61}$, and $R^{62}$ are each independently a $C_1$-$C_{12}$ straight, branched or cyclic alkyl group which may contain a carbonyl, ester or ether moiety, or a $C_6$-$C_{12}$ aryl group, $C_7$-$C_{20}$ aralkyl group or mercaptophenyl group; $A^1$ is a single bond, -$A^0$-C(=O)—O—, -$A^0$-O— or -$A^0$-O—C(=O)—, $A^0$ is a $C_1$-$C_{12}$ straight, branched or cyclic alkylene group which may contain a carbonyl, ester or ether moiety; $A^2$ is hydrogen or trifluoromethyl; $Z^1$ is a single bond, methylene, ethylene, phenylene, fluorinated phenylene, —O—$R^{64}$—, or —C(=O)—$Z^2$—$R^{64}$—, $Z^2$ is —O— or —NH—, $R^{64}$ is a $C_1$-$C_6$ straight, branched or cyclic alkylene or alkenylene group which may contain a carbonyl, ester, ether or hydroxyl moiety, or phenylene, fluorinated phenylene or trifluoromethyl-substituted phenylene group; M⁻ is a non-nucleophilic counter ion, and f1, f2 and f3 are numbers in the range: 0≤f1≤0.5, 0≤f2≤0.5, 0≤f3≤0.5, and 0<f1+f2+f3≤0.5.

The resist composition may further comprise a surfactant.

In another aspect, the invention provides a process for forming a pattern comprising the steps of applying the resist composition defined above onto a substrate, baking to form a resist film, exposing the resist film to high-energy radiation, and developing the exposed film in a developer.

In a preferred embodiment, the high-energy radiation is ArF excimer laser radiation of wavelength 193 nm, KrF excimer laser radiation of wavelength 248 nm, EB, or EUV of wavelength 3 to 15 nm.

Advantageous Effects of Invention

Since a resist film containing a specific phosphazene salt compound exhibits an acid diffusion suppressing effect and a high dissolution contrast, it offers improved resolution, a wide focus margin, a reduced LWR, and no dimensional changes on PPD as a positive or negative tone resist film subject to alkaline development and as a negative tone resist film subject to organic solvent development.

DESCRIPTION OF EMBODIMENTS

As used herein, the singular forms "a," "an" and "the" include plural referents unless the context clearly dictates otherwise. The notation ($C_n$-$C_m$) means a group containing from n to m carbon atoms per group. Me stands for methyl, Ac for acetyl, and Ph for phenyl.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PPD: post PEB delay
PAG: photoacid generator
LWR: line width roughness Resist Composition The resist composition of the invention is defined as comprising a base polymer and a specific phosphazene salt compound. The phosphazene salt compound undergoes ion exchange with sulfonic acid, sulfonimide or sulfonmethide generated by an acid generator, especially sulfonic acid having a fluorinated alkyl group, bissulfonimide or trissulfonmethide, to form a salt and release carboxylic acid or sulfonamide. Because of its very high basicity, the phosphazene compound has a high acid trapping ability and acid diffusion suppressing effect. Since the phosphazene salt compound is not photosensitive, it does not convert to a phosphazene compound upon receipt of light and maintains a sufficient acid trapping ability even in the unexposed region. Thus it helps suppress acid diffusion from the exposed region to the unexposed region.

While the resist composition of the invention should essentially contain the phosphazene salt compound, another amine compound, ammonium salt, sulfonium salt or iodonium salt may be separately added as the quencher. Examples of the ammonium, sulfonium or iodonium salt to be added as the quencher include sulfonium or iodonium salts of carboxylic acid, sulfonic acid, sulfonamide and saccharin. The carboxylic acid used herein may or may not be fluorinated at α-position.

The phosphazene salt compound exerts an acid diffusion suppressing effect and contrast enhancing effect, which may stand good either in positive and negative tone pattern formation by alkaline development or in negative tone pattern formation by organic solvent development.

Phosphazene Salt Compound

The phosphazene salt compound to be included in the inventive resist composition has the following formula (A).

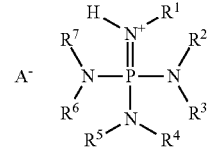

(A)

In formula (A), $R^1$ to $R^7$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, which may contain an ester, ether, sulfide, sulfoxide, carbonate, carbamate, sulfone, halogen, amino, amide, hydroxy, thiol or nitro moiety, a pair of $R^1$ and $R^2$, $R^2$ and $R^3$, $R^3$ and $R^4$, $R^4$ and $R^5$, $R^5$ and $R^6$, or $R^6$ and $R^7$ may bond together to form a ring, or a pair of $R^2$ and $R^3$, $R^4$ and $R^5$, or $R^6$ and $R^7$, taken together, may form a double bond or a group having the formula (A)-1, $R^1$ may be a group having the formula (A)-2.

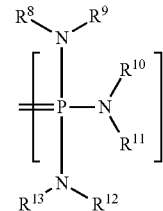

(A)-1

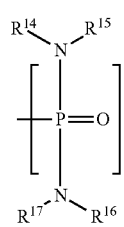

(A)-2

Herein $R^8$ to $R^{17}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, a pair of $R^8$ and $R^9$, $R^9$ and $R^{10}$, $R^{10}$ and $R^{11}$, $R^{11}$ and $R^{12}$, $R^{12}$ and $R^{13}$, $R^{14}$ and $R^{15}$, or $R^{16}$ and $R^{17}$ may bond together to form a ring, or a pair of $R^8$ and $R^9$, $R^{10}$ and $R^{11}$, or $R^{12}$ and $R^{13}$, taken together, may form a double bond or a group having the formula (A)-1.

In formula (A), $A^-$ is an anion selected from among hydroxide, chloride, bromide, iodide, nitrate, nitrite, chlorate, chlorite, perchlorate, hydrogencarbonate, dihydrogenphosphate, hydrogensulfate, thiocyanate, hydrogenoxalate, cyanide, iodate ions, and anions of the formulae (M-1) and (M-2).

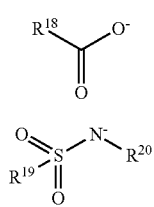
(M)-1

(M)-2

In formula (M-1), $R^{18}$ is hydrogen, or a $C_1$-$C_{30}$ straight, branched or cyclic alkyl group, $C_2$-$C_{30}$ straight, branched or cyclic alkenyl group, $C_2$-$C_{30}$ straight, branched or cyclic alkynyl group, $C_5$-$C_{20}$ aryl group, $C_7$-$C_{20}$ aralkyl group, or $C_3$-$C_{20}$ aromatic or aliphatic heterocycle-containing group, which may contain an ester, ether, sulfide, sulfoxide, carbonate, carbamate, sulfone, halogen, amino, amide, hydroxy, thiol or nitro moiety, with the proviso that $R^{18}$ does not contain a group of the formula (A)-3:

(A)-3 wherein Ar is a $C_6$-$C_{16}$ aromatic group, $R^{21}$ and $R^{22}$ are each independently hydrogen, hydroxy, alkoxy, $C_1$-$C_6$ straight, branched or cyclic alkyl group, or $C_6$-$C_{10}$ aryl group. In formula (M-2), $R^{19}$ is fluorine, or a $C_1$-$C_{13}$ straight, branched or cyclic fluoroalkyl group or fluorophenyl group, which may contain a hydroxy, ether, ester or alkoxy moiety. $R^{20}$ is hydrogen, or a $C_1$-$C_{10}$ straight, branched or cyclic alkyl group, $C_2$-$C_{10}$ straight, branched or cyclic alkenyl group, $C_2$-$C_{10}$ straight or branched alkynyl group, or $C_5$-$C_{13}$ aryl group, which may contain a hydroxy, ether, ester or alkoxy moiety.

Examples of the carboxylate anion having formula (M-1) are given below, but not limited thereto.

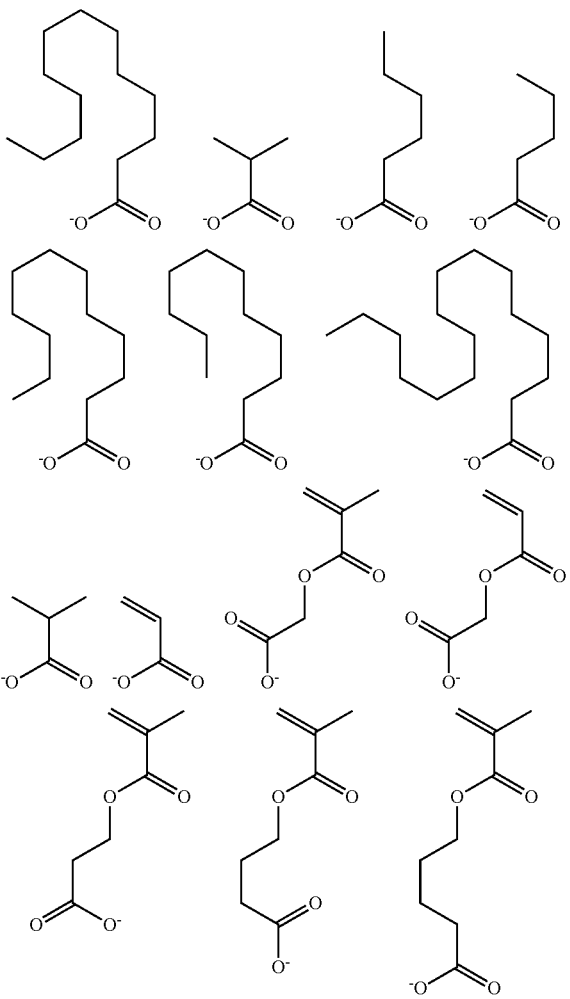

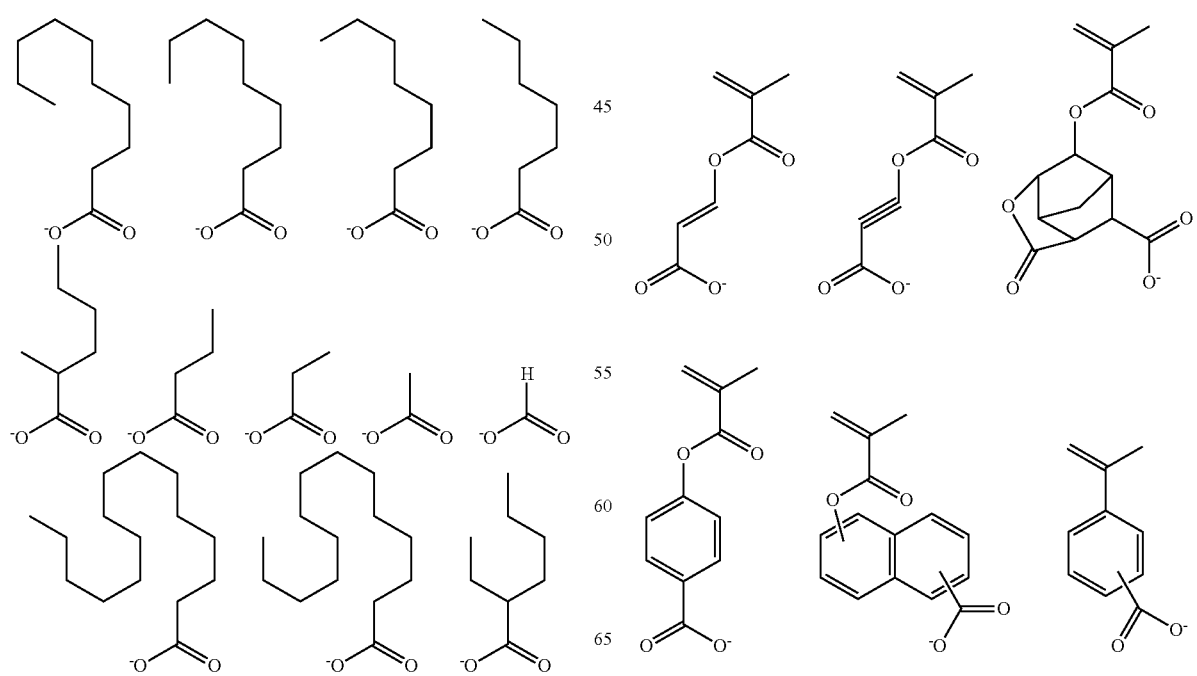

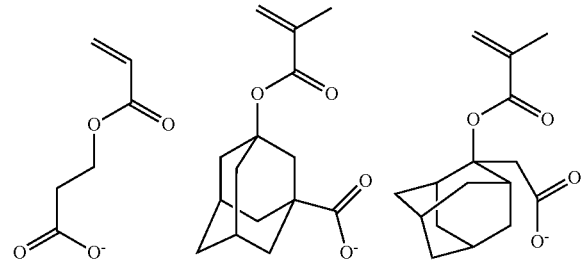
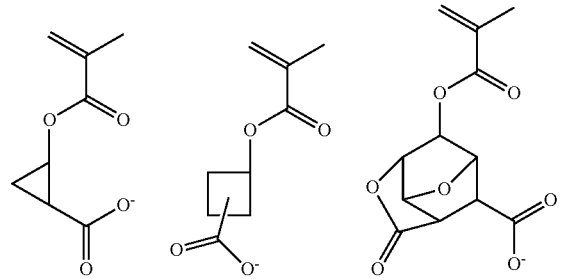
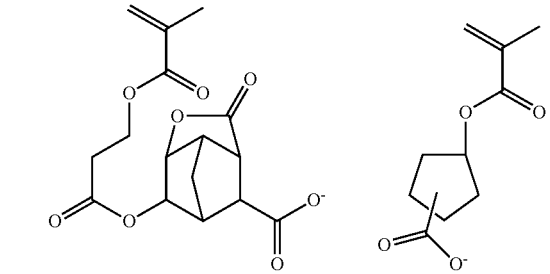
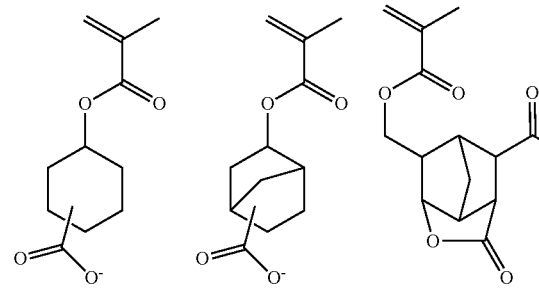
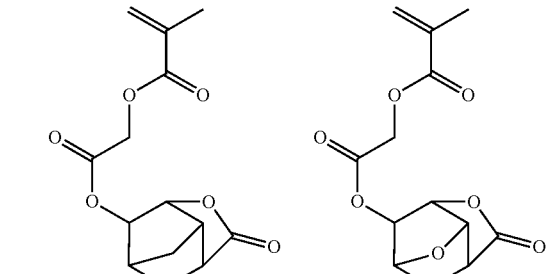
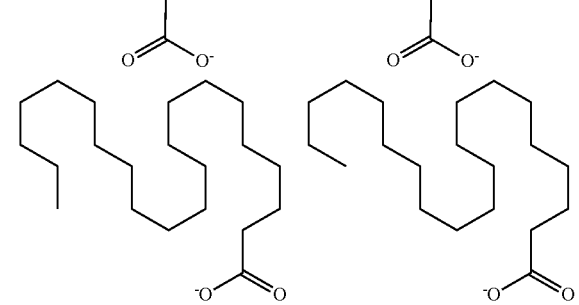
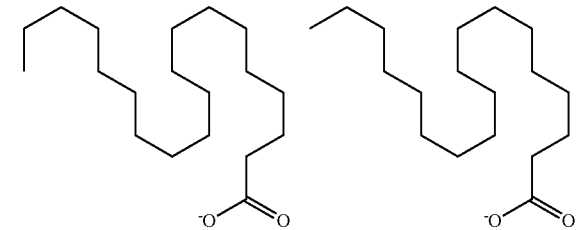
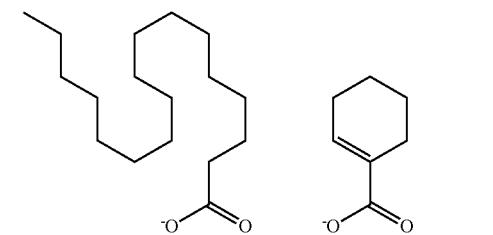
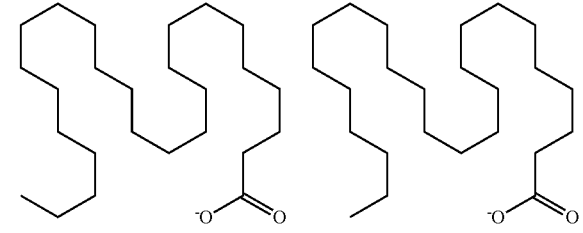
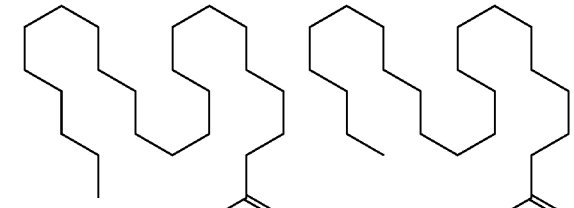
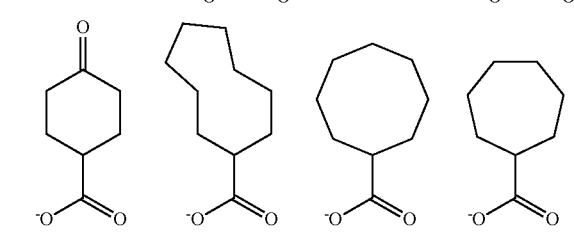
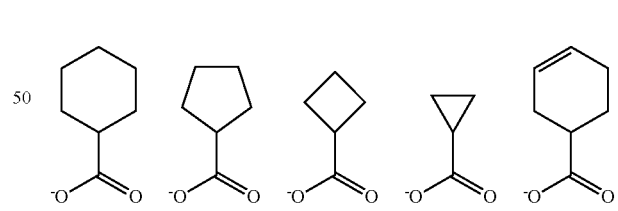
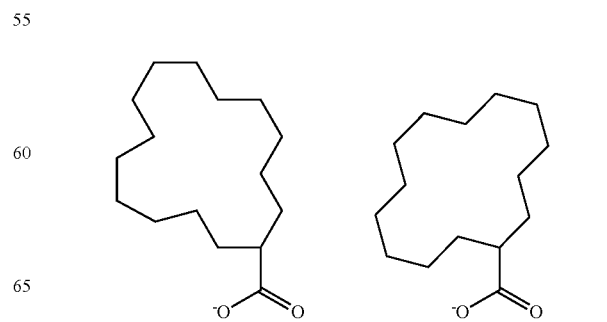

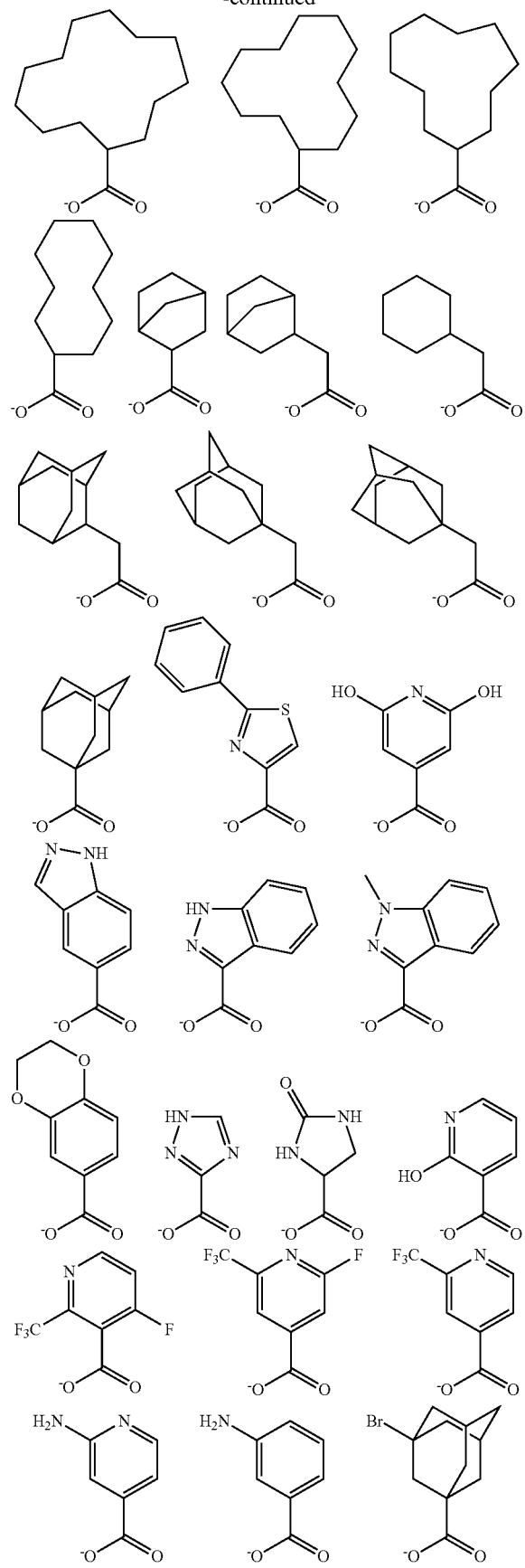
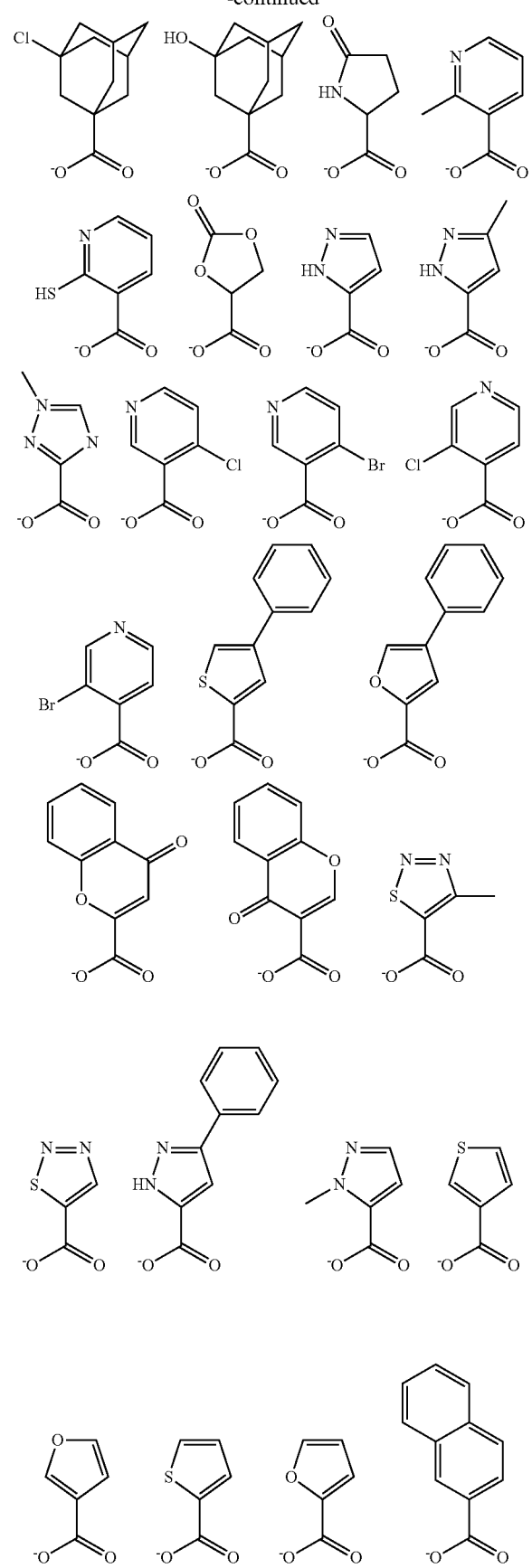

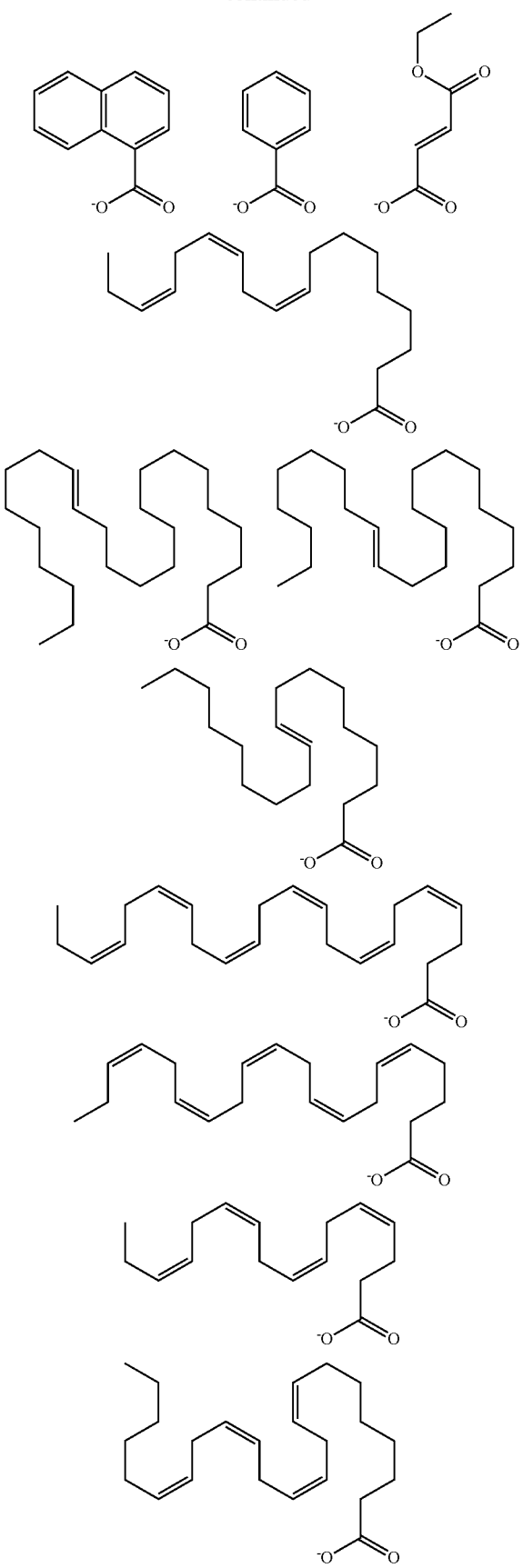
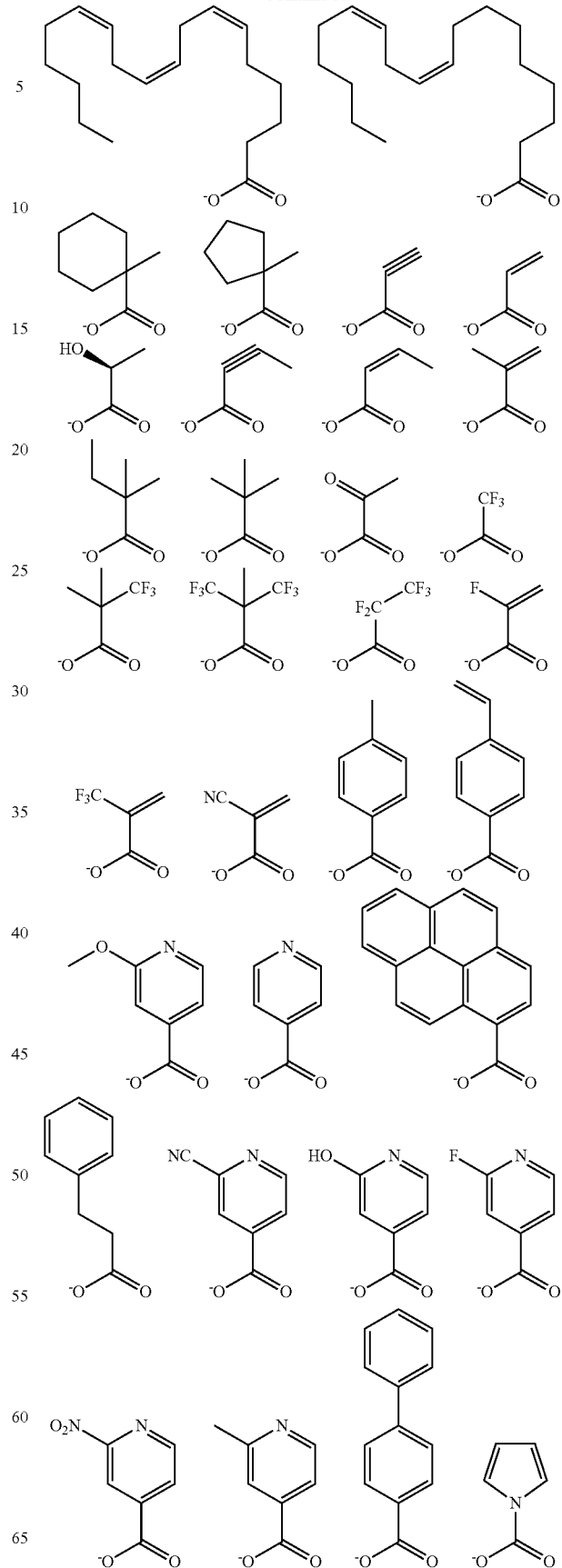

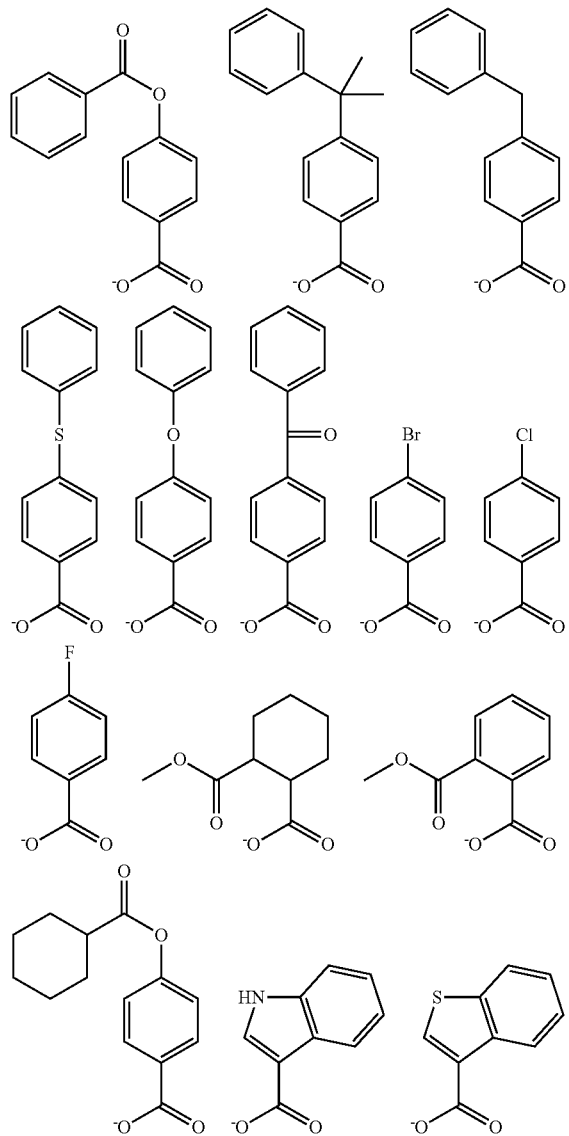
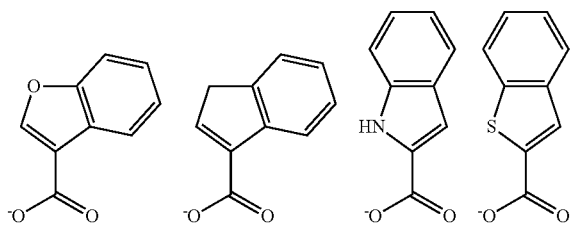
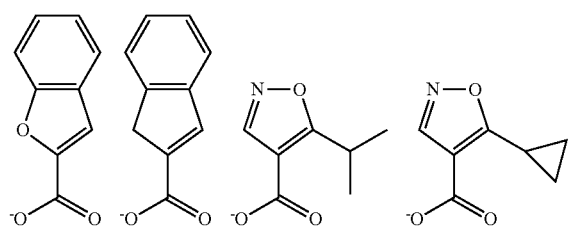
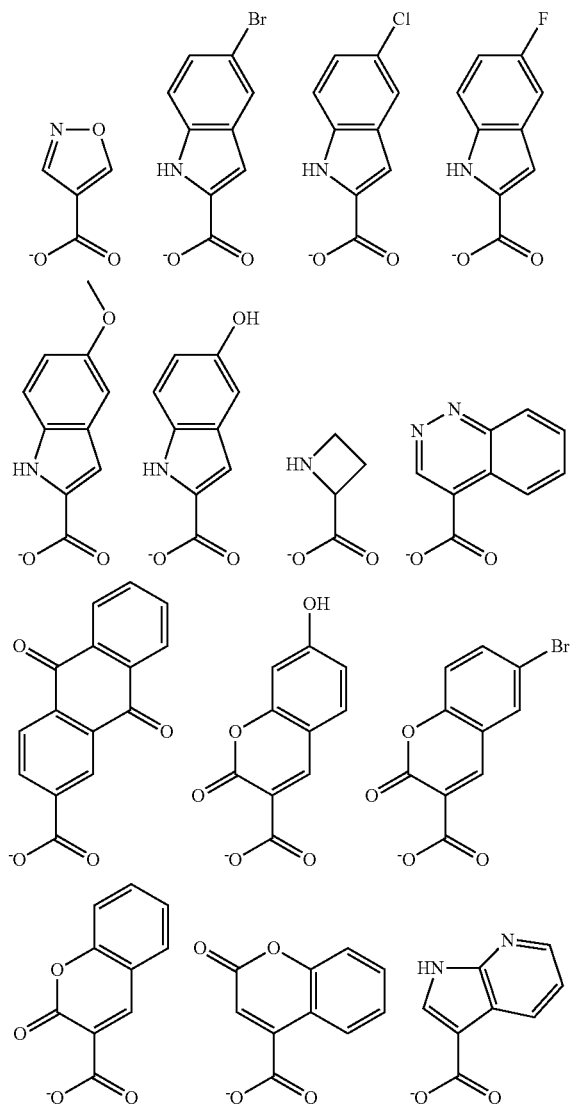
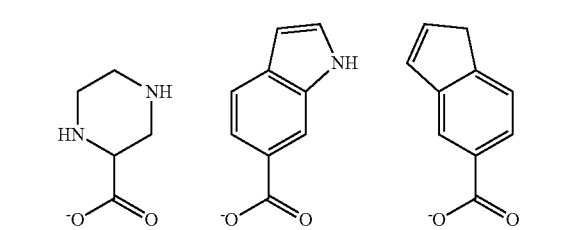

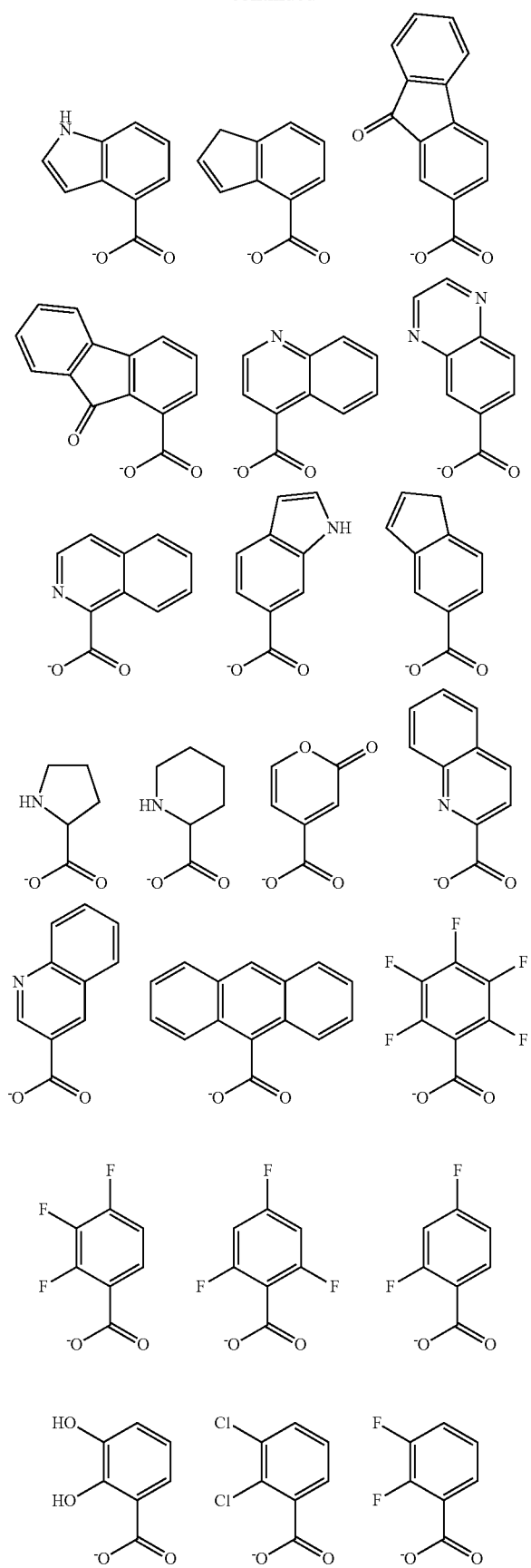
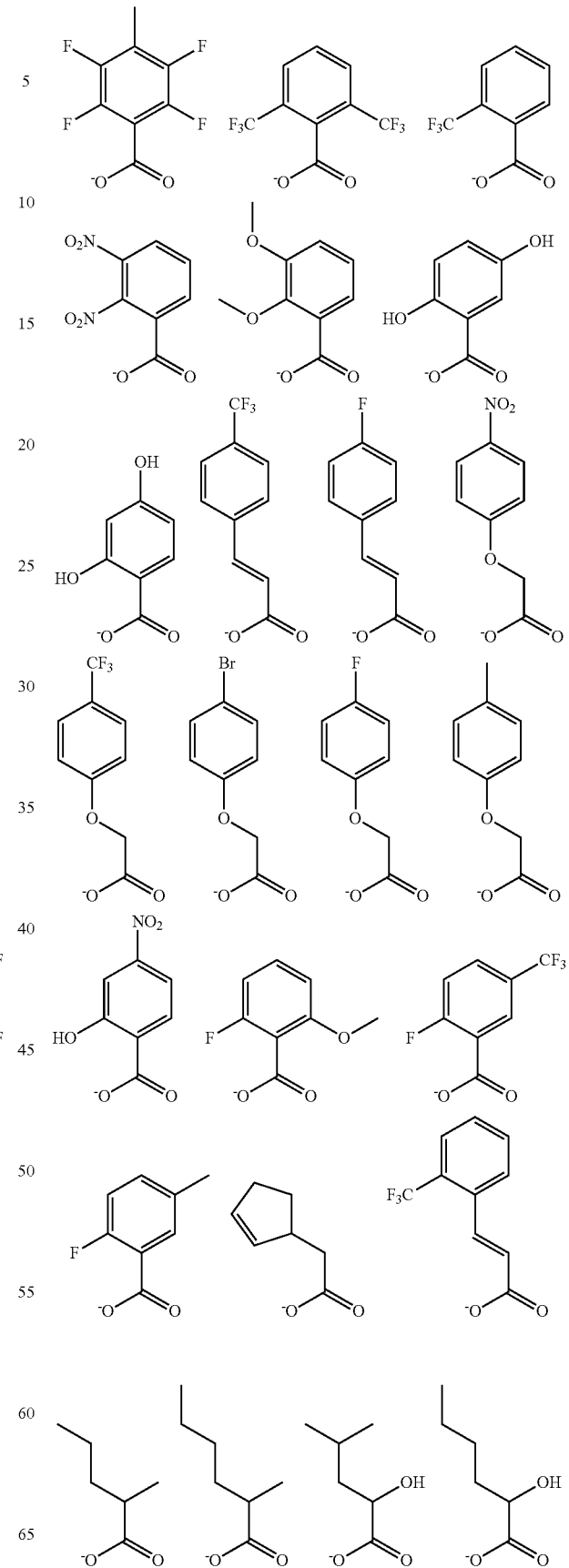

21
-continued
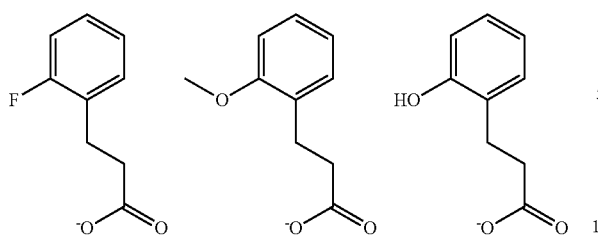
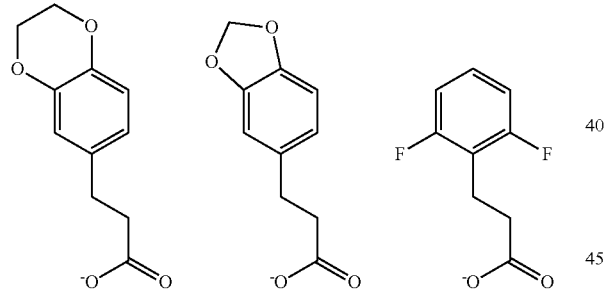
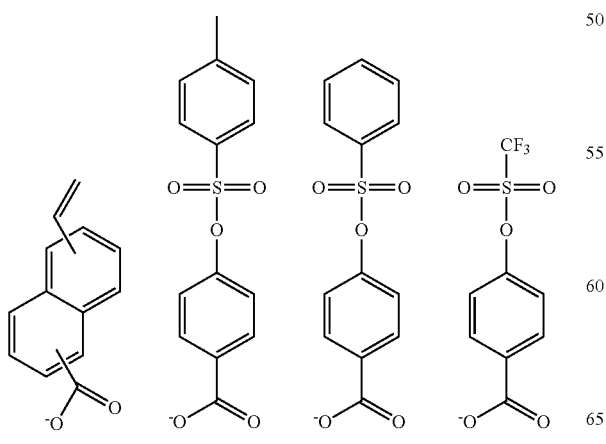
22
-continued
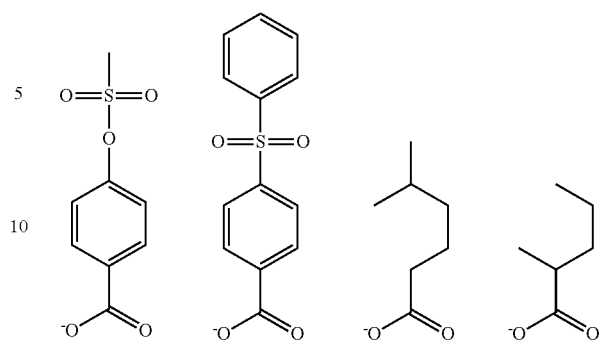
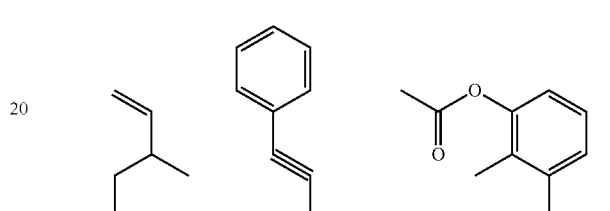
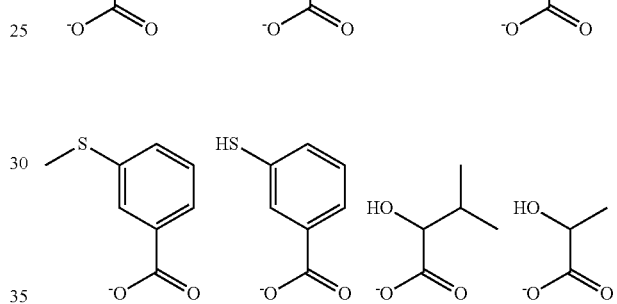
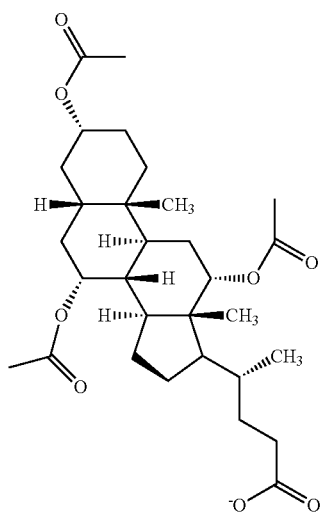

23
-continued
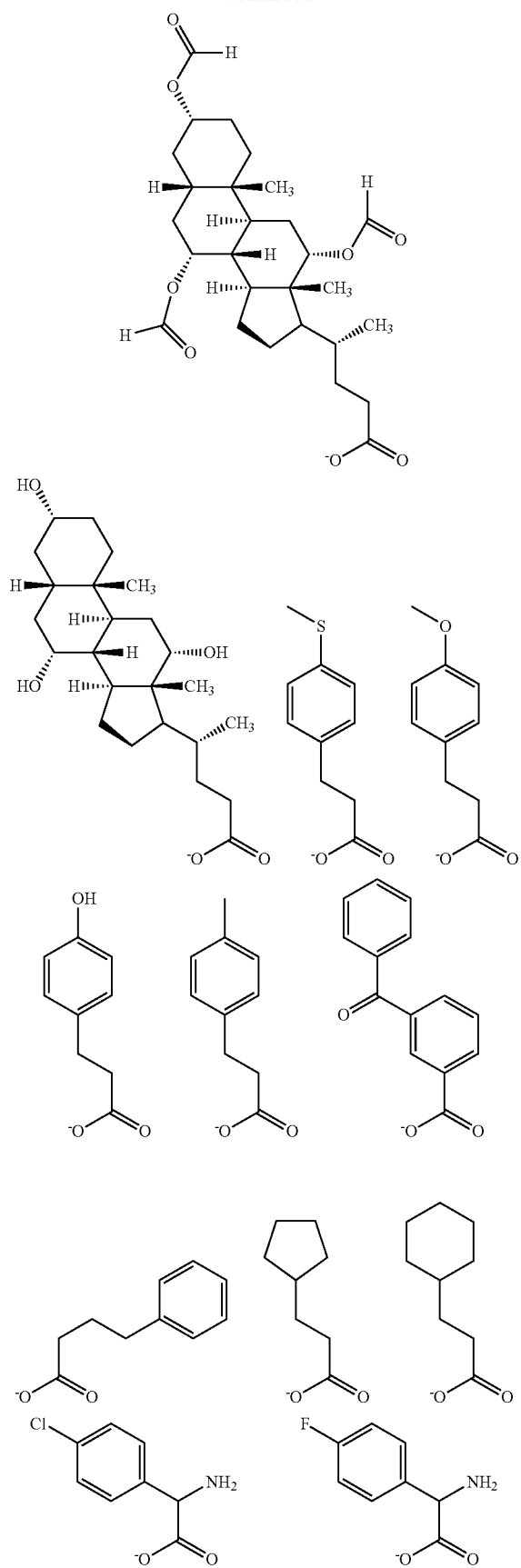
24
-continued
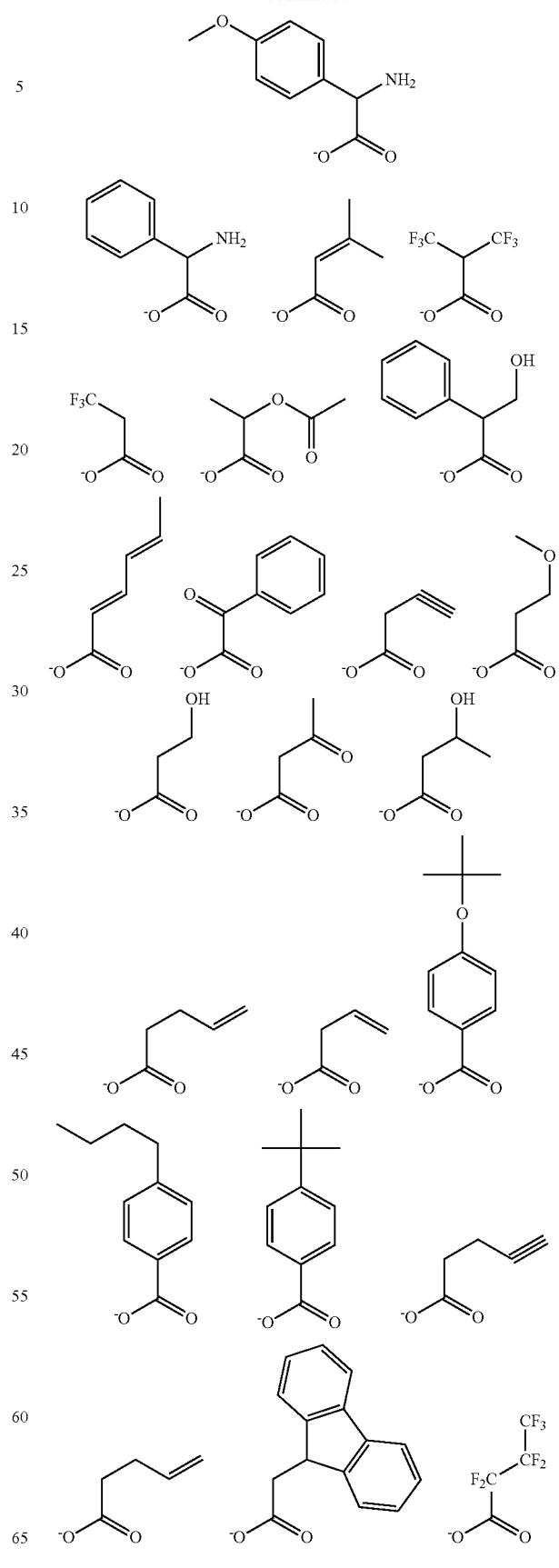

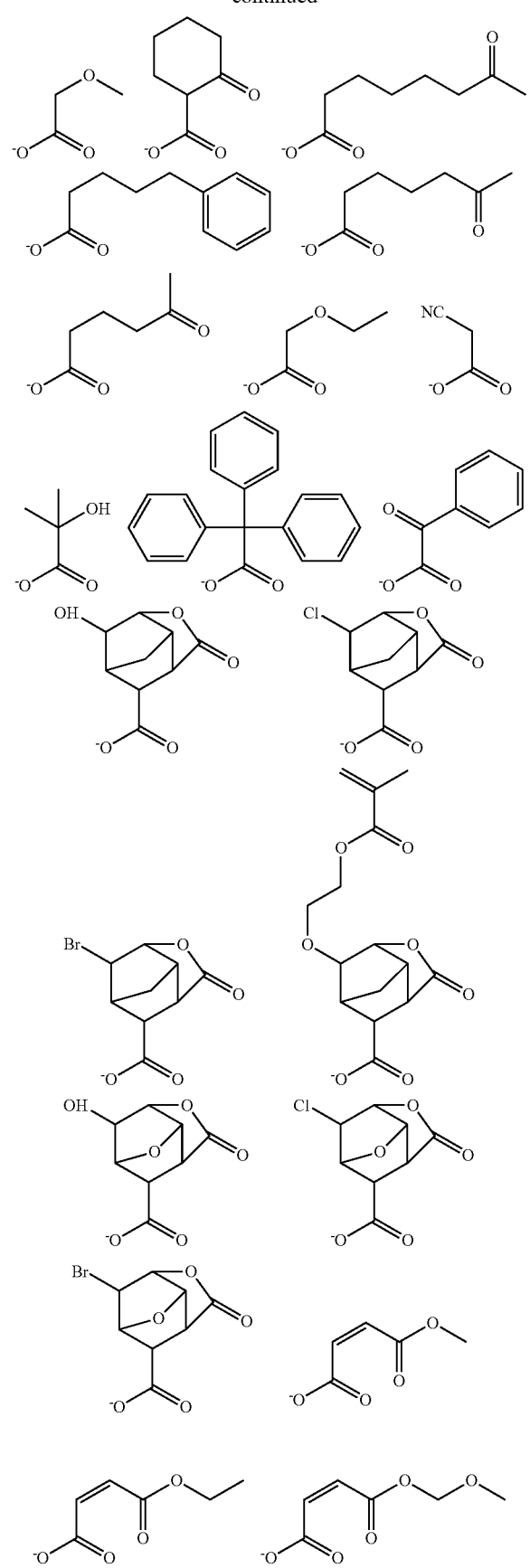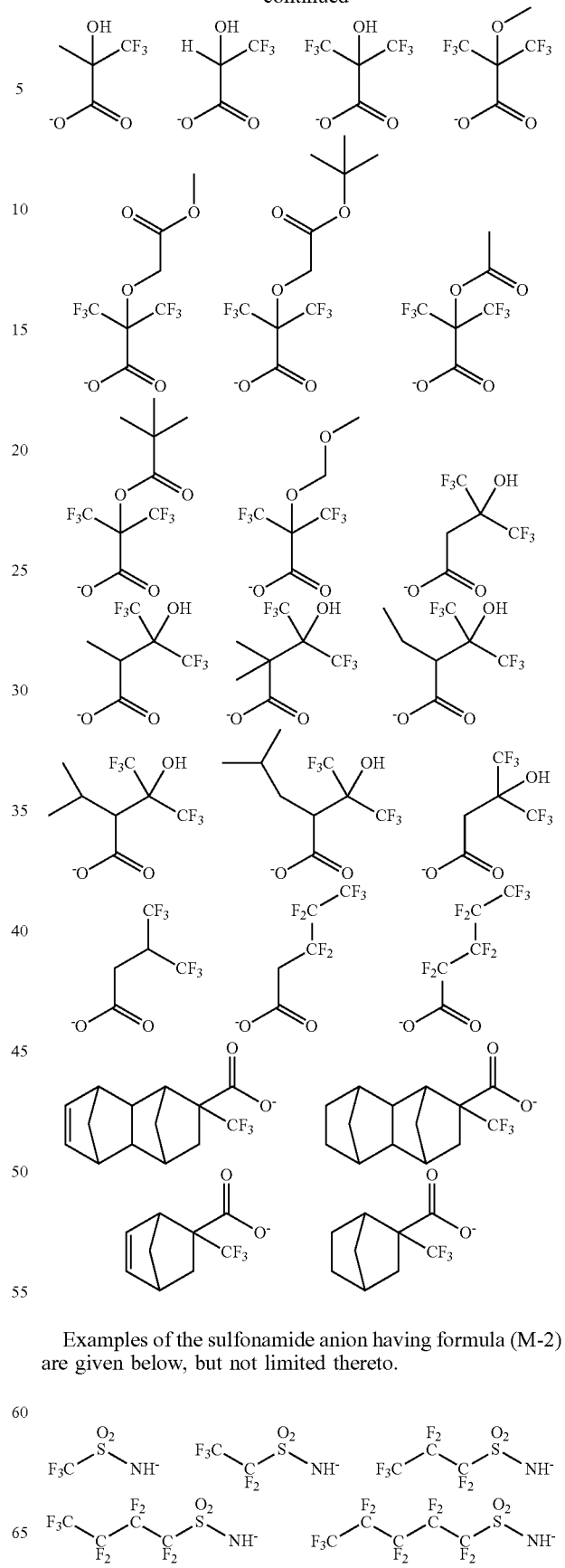
Examples of the sulfonamide anion having formula (M-2) are given below, but not limited thereto.
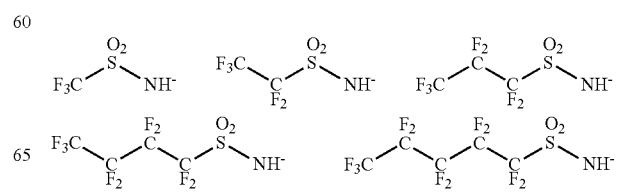

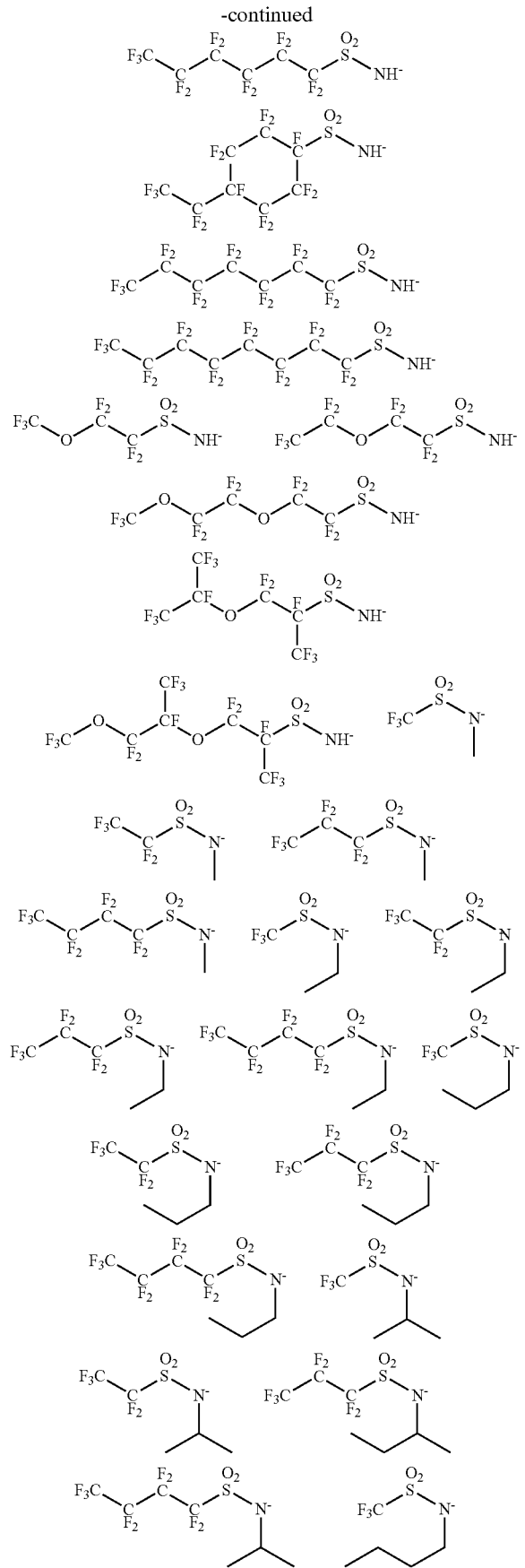
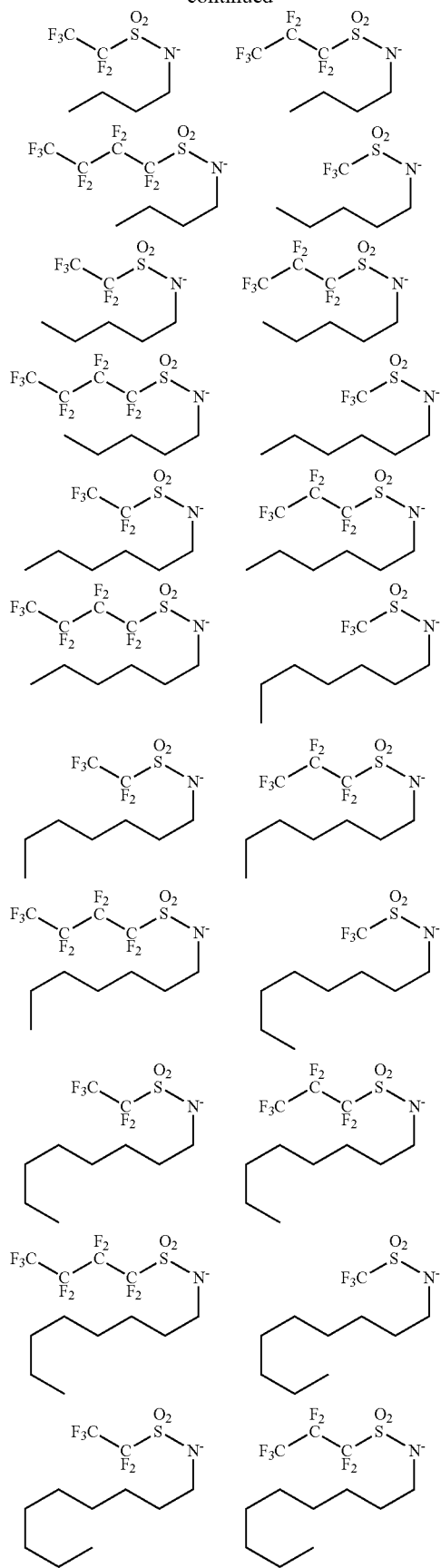

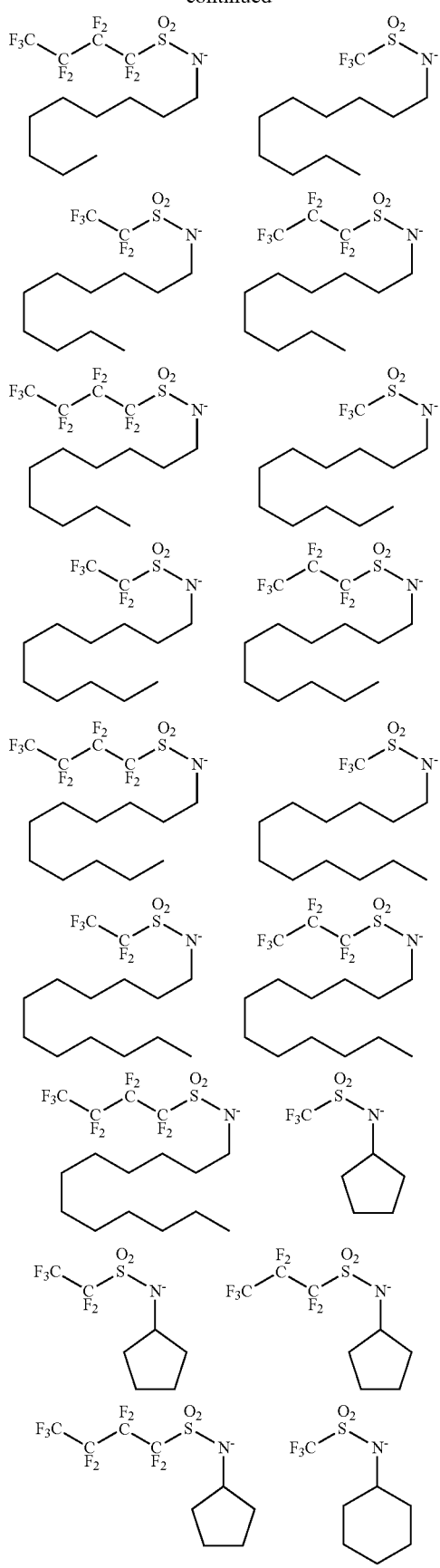
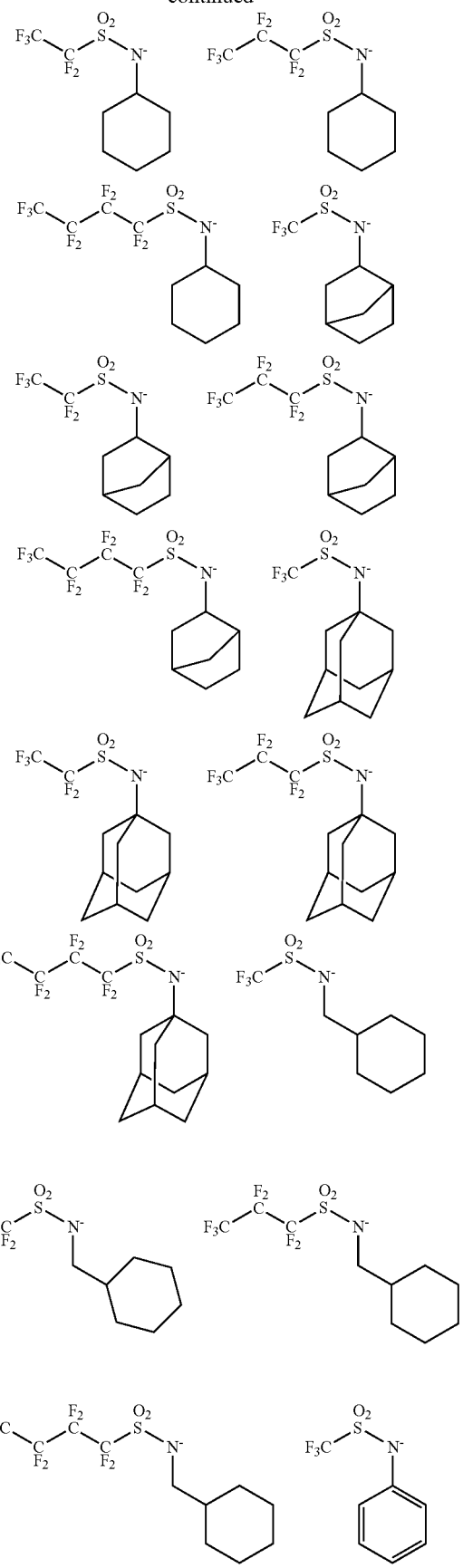

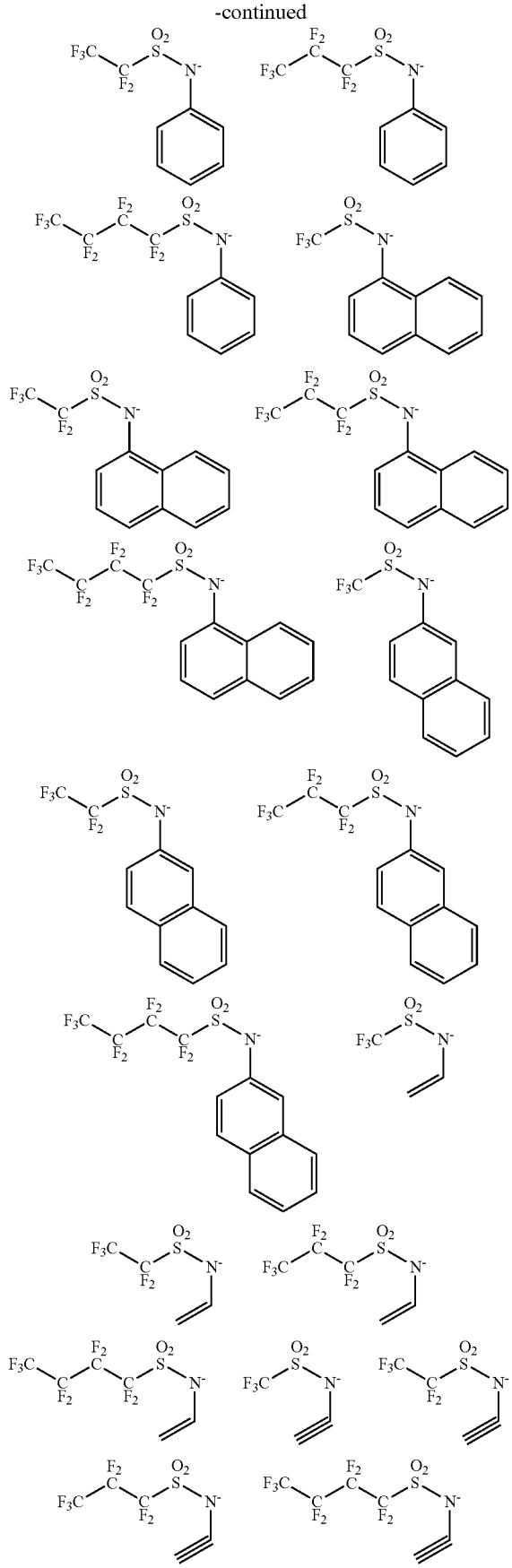
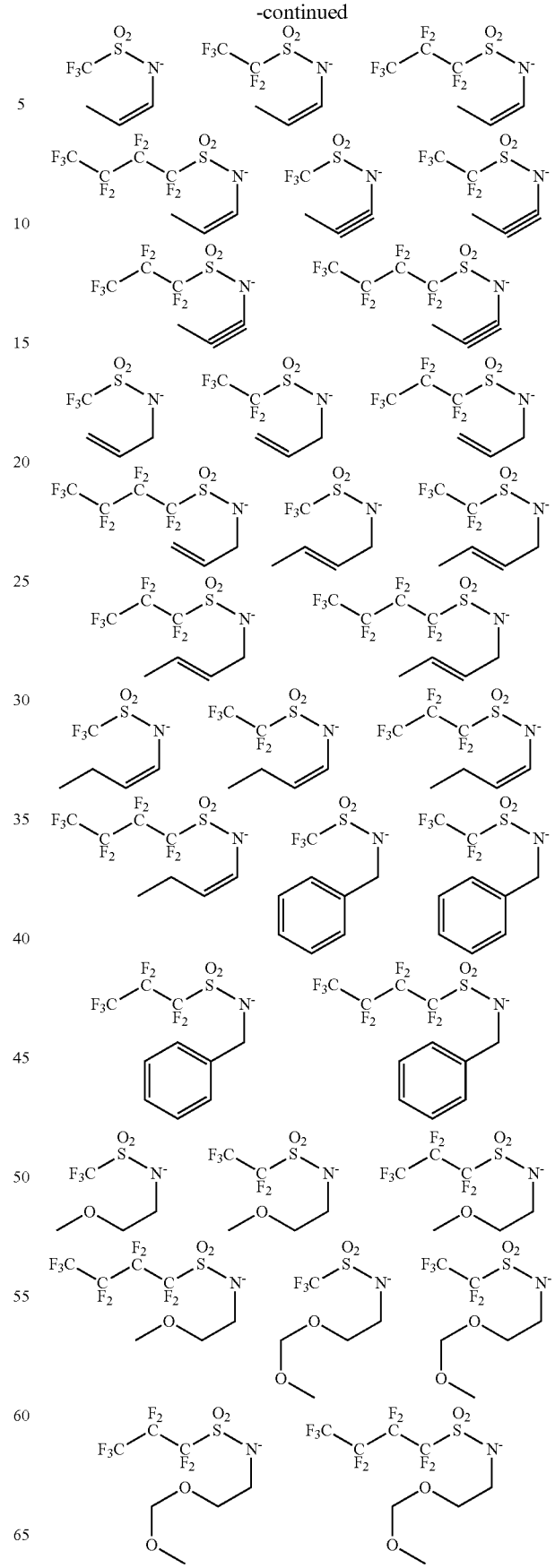

33
-continued
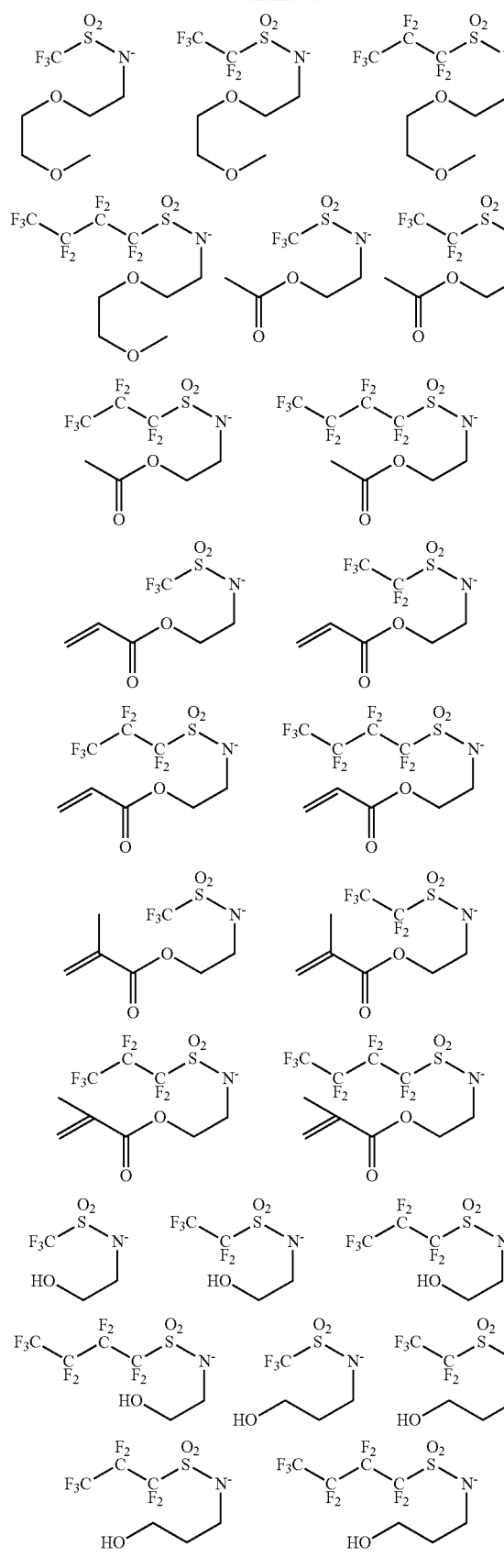
34
-continued
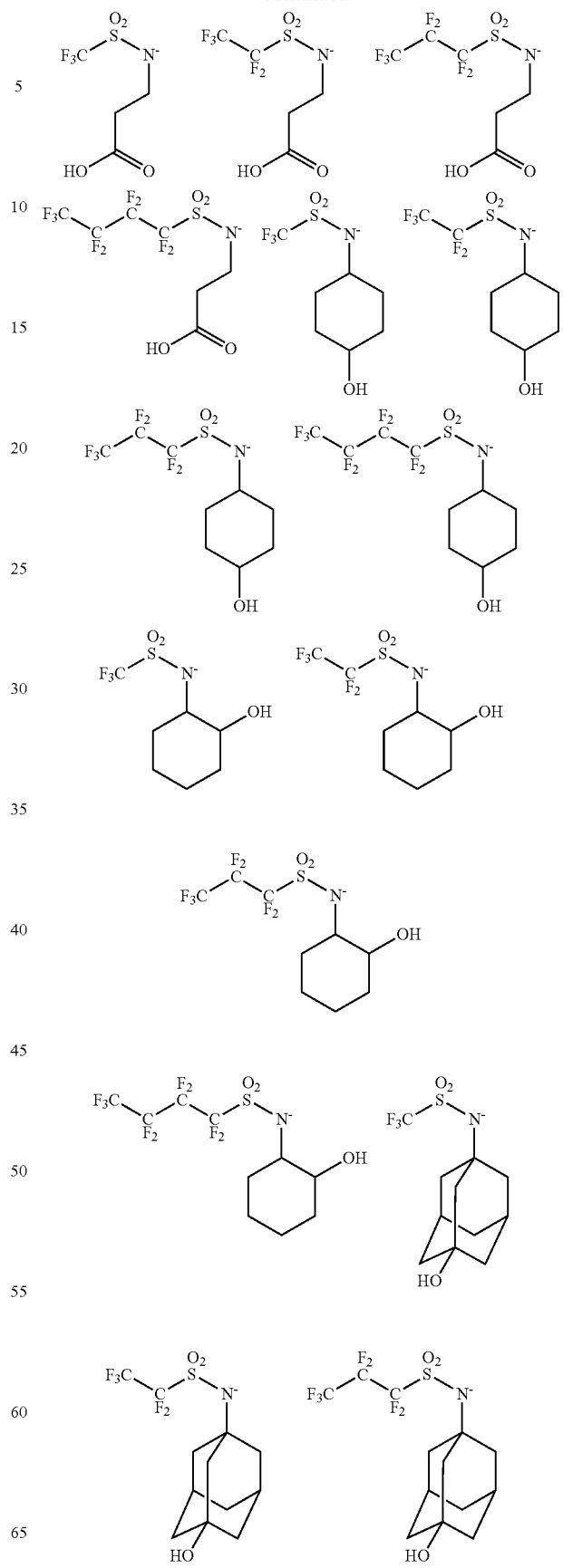

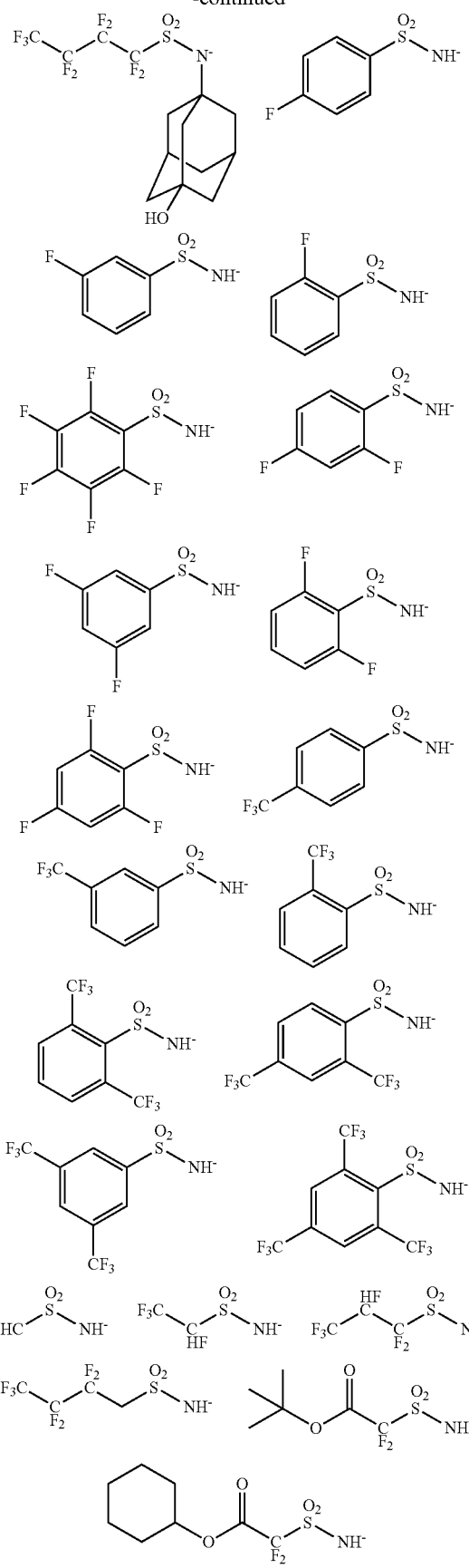
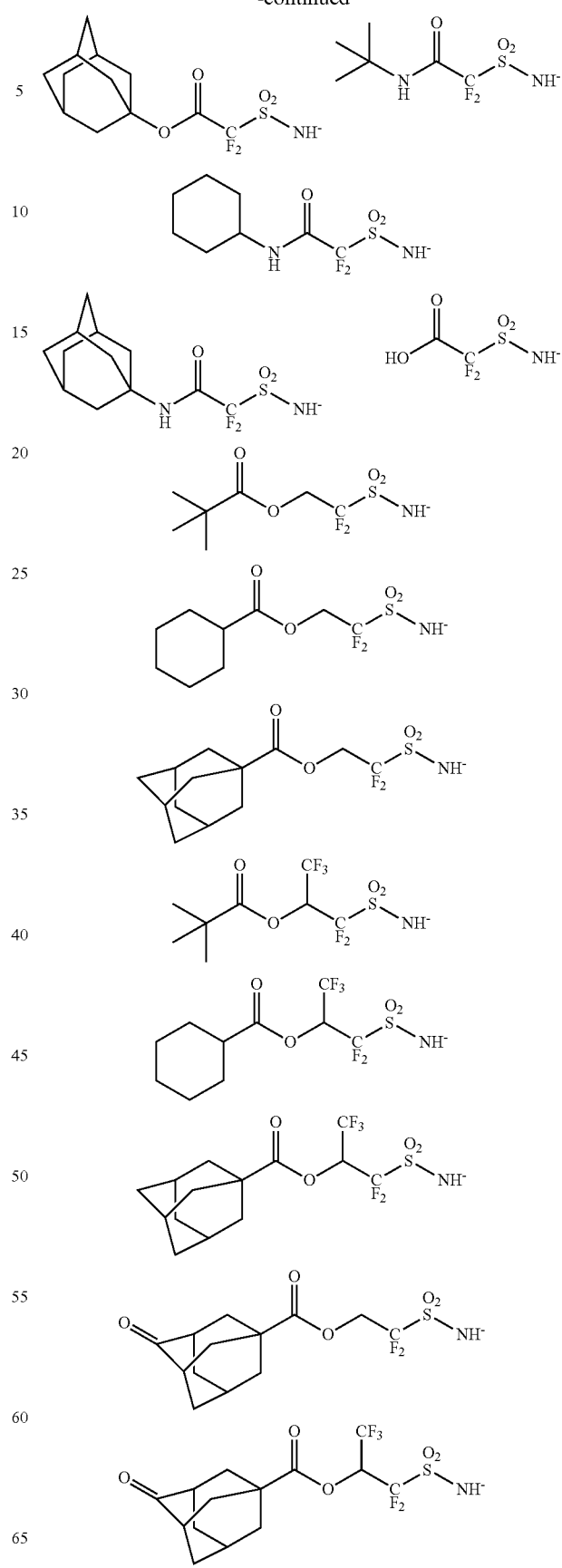

37
-continued
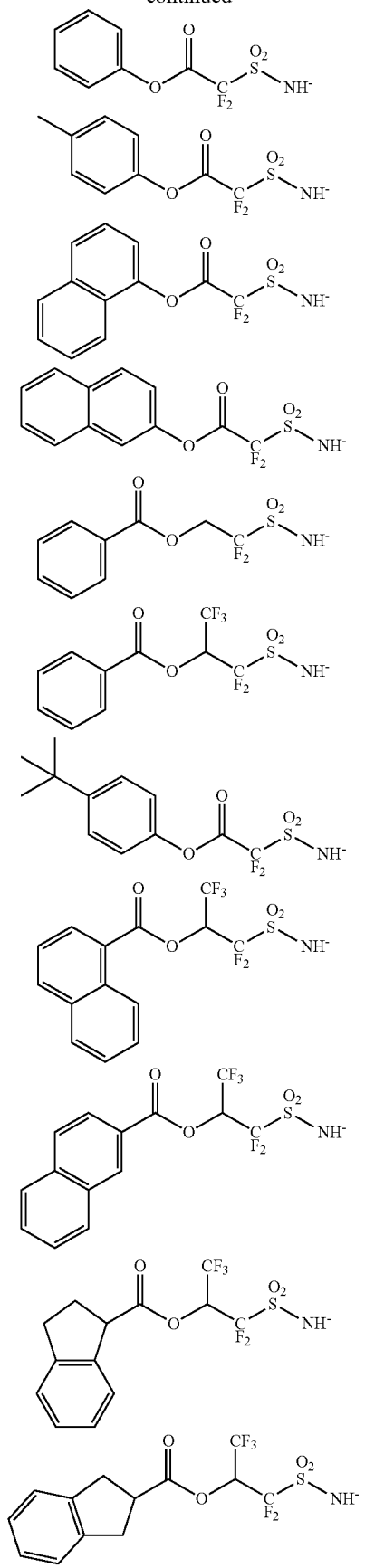
38
-continued
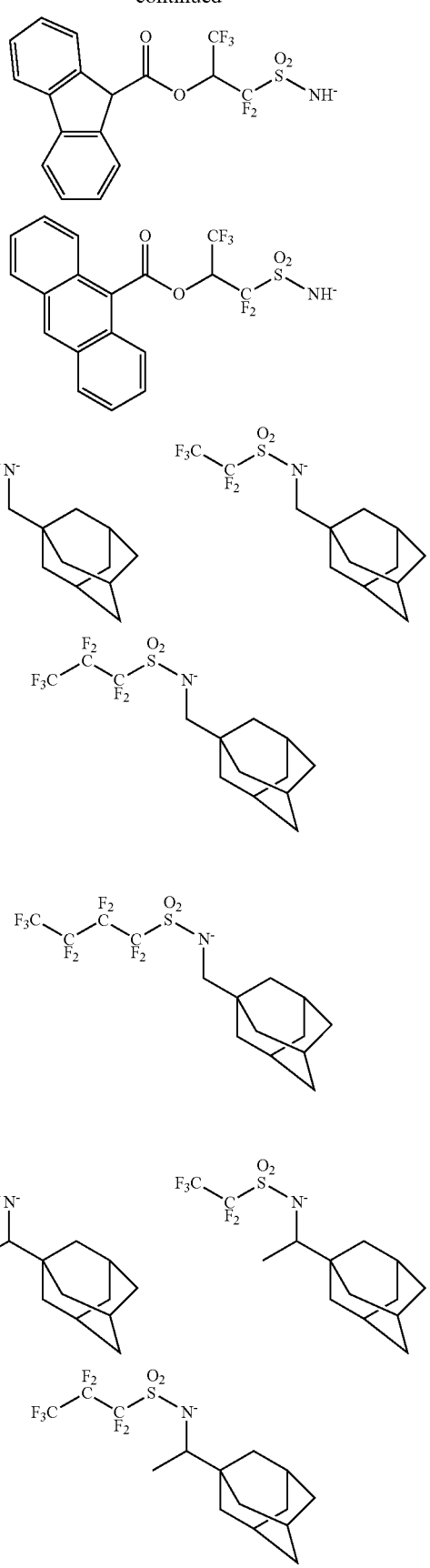

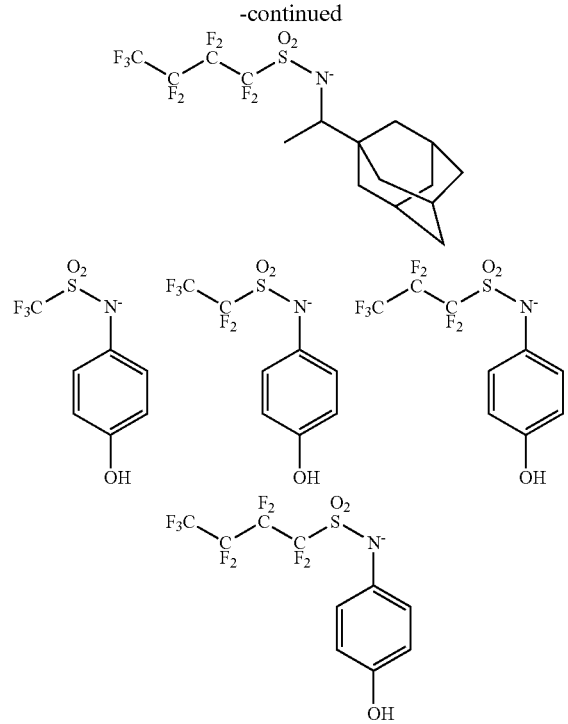
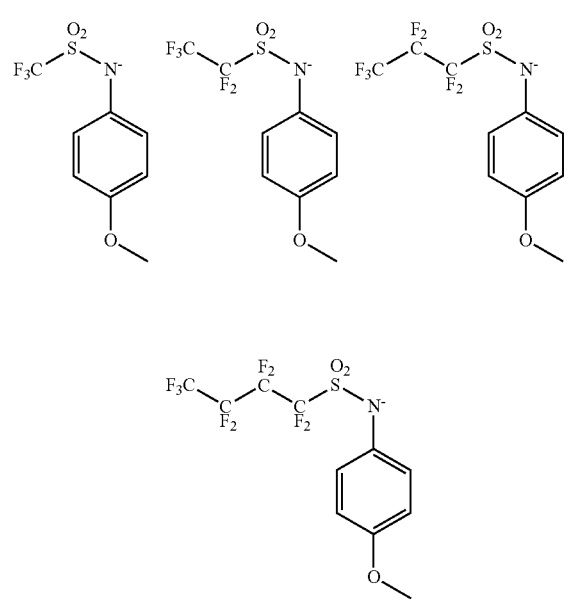
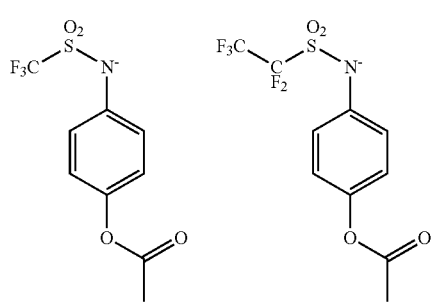
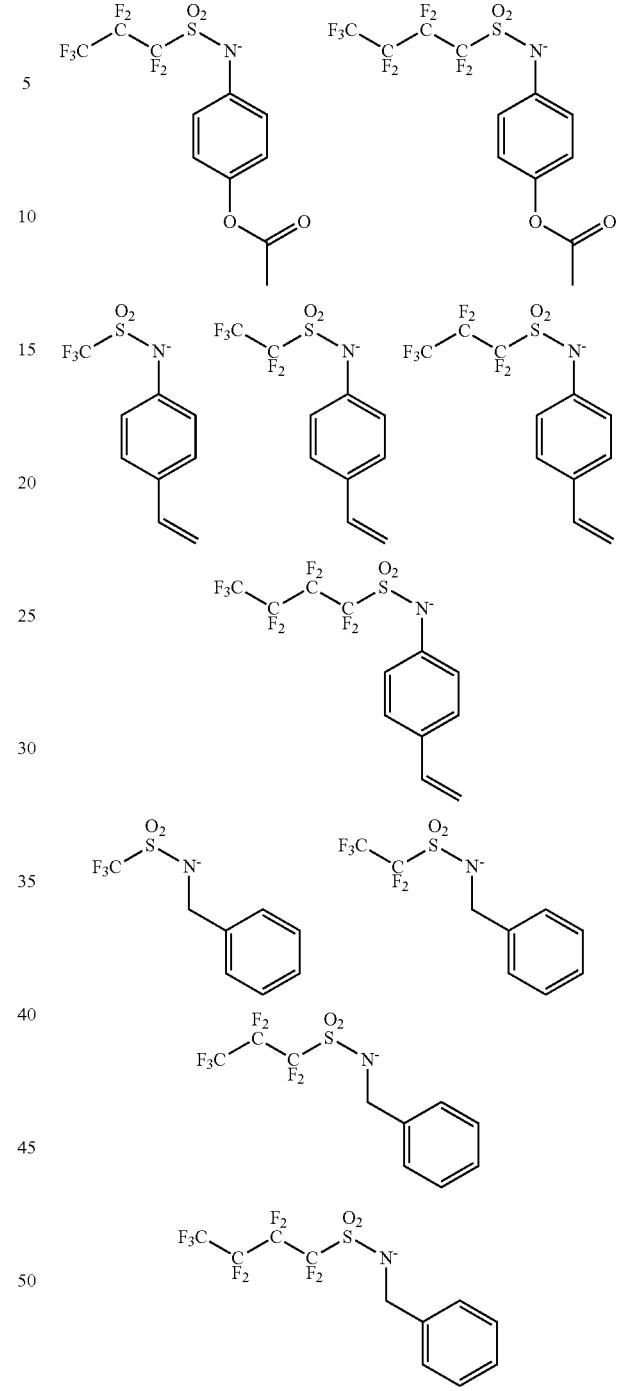
Examples of the cation in the phosphazene salt compound having formula (A) are given below, but not limited thereto.
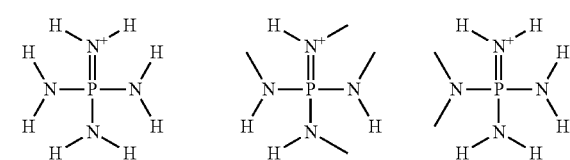

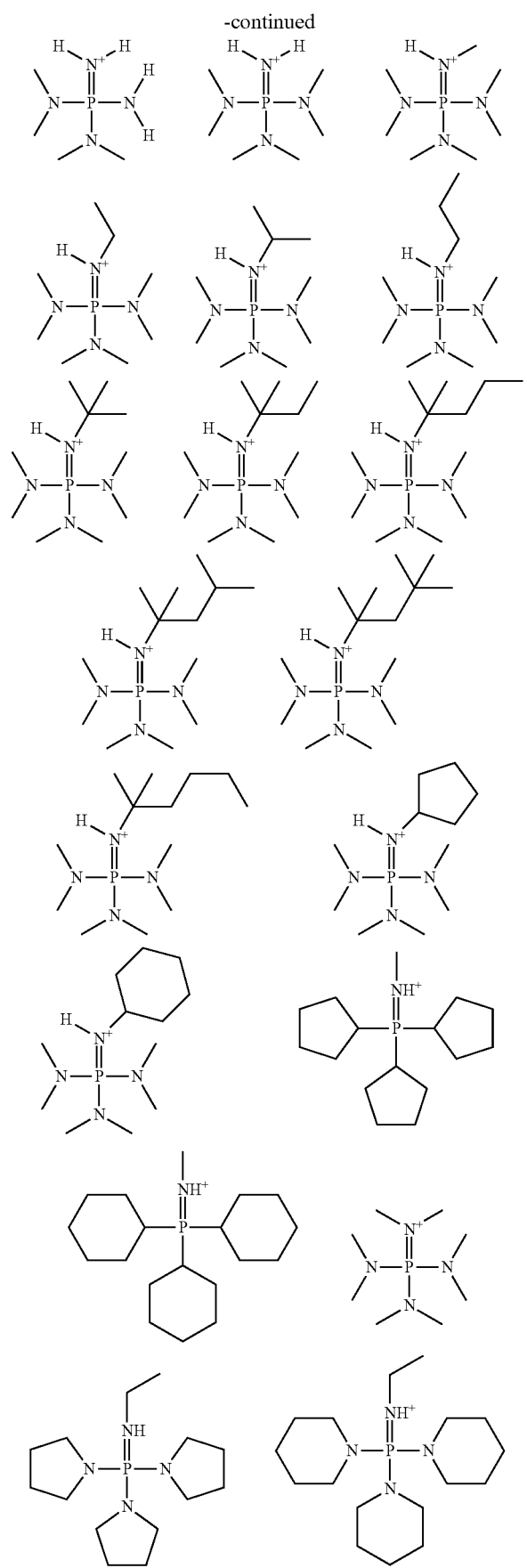
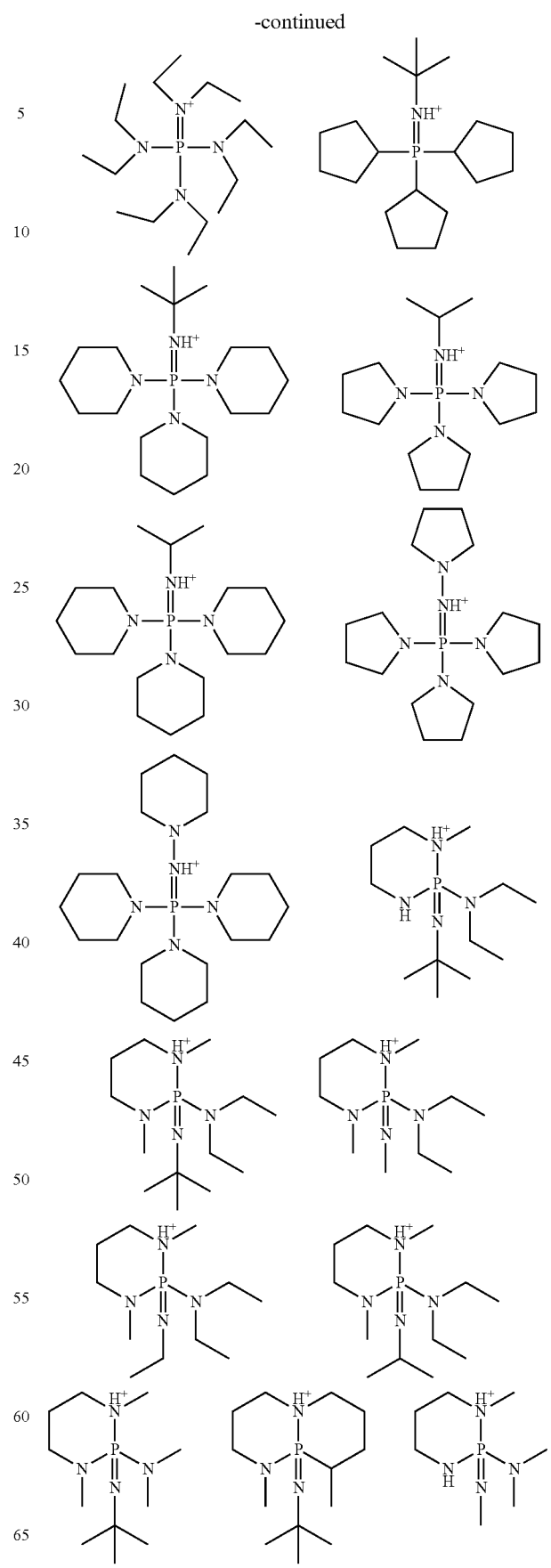

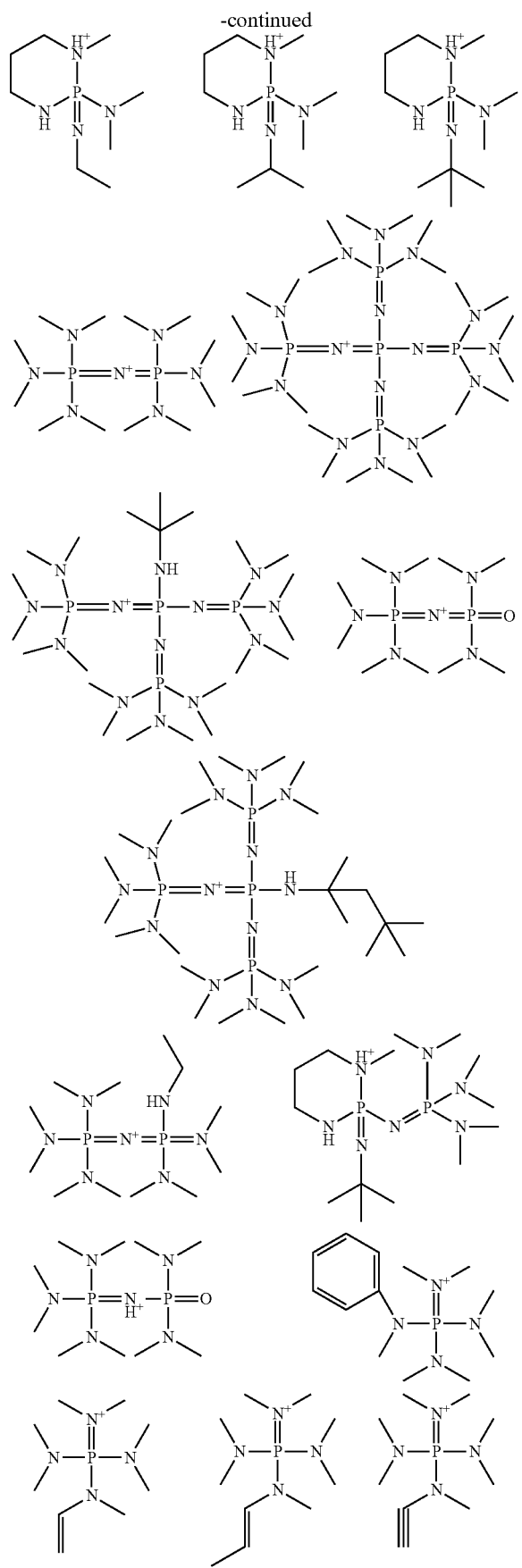
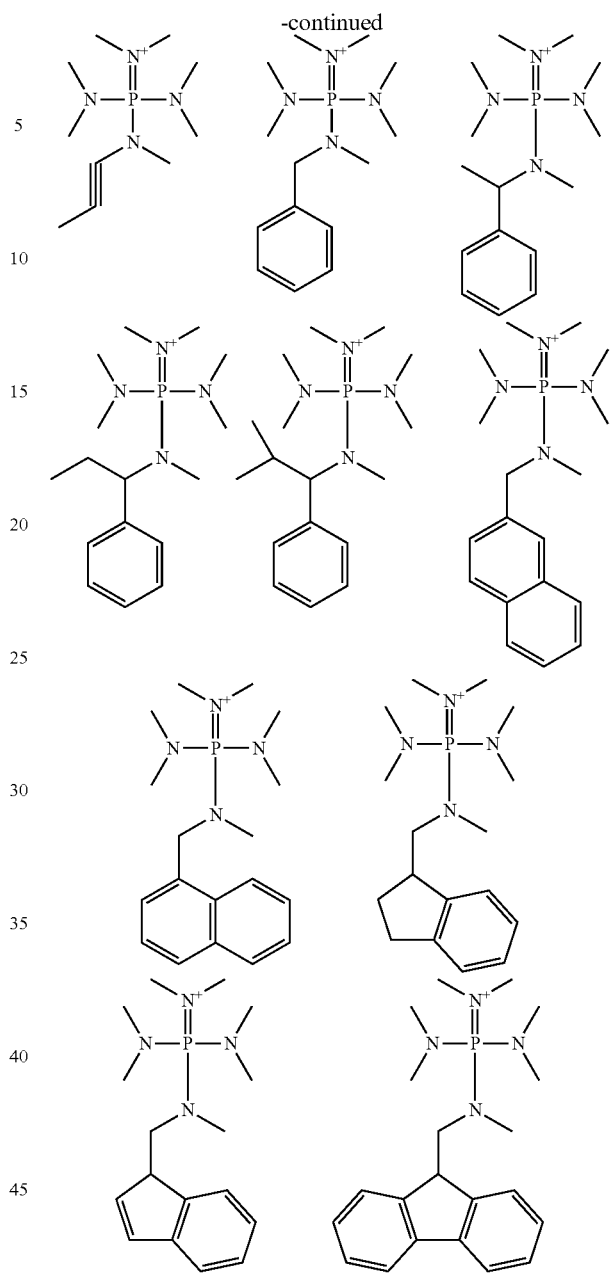

The phosphazene cation has a positive charge which is delocalized on the phosphorus atom and surrounding nitrogen atoms. This means that the site of trapping an anion of sulfonic acid, sulfonimide or sulfonmethide for neutralization is present everywhere so that the anion may be quickly trapped. Therefore, the phosphazene salt compound is a superior quencher having a high trapping ability as well as a high basicity.

The phosphazene salt compound having formula (A) may be synthesized, for example, by mixing a phosphazene compound with a carboxylic acid or sulfonamide.

In the resist composition, the phosphazene salt compound having formula (A) is preferably used in an amount of 0.001 to 50 parts, more preferably 0.01 to 20 parts by weight per 100 parts by weight of the base polymer, as viewed from sensitivity and acid diffusion suppressing effect.

Base Polymer

Where the resist composition is of positive tone, the base polymer comprises recurring units containing an acid labile group, preferably recurring units having the formula (a1) or recurring units having the formula (a2). These units are simply referred to as recurring units (a1) and (a2).

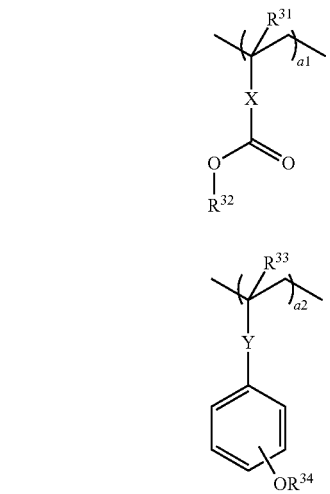

Herein $R^{31}$ and $R^{33}$ are each independently hydrogen or methyl. $R^{32}$ and $R^{34}$ are each independently an acid labile group. X is a single bond, ester group, phenylene group, naphthylene group or a $C_1$-$C_{12}$ linking group containing lactone ring, with a single bond, phenylene or naphthylene being preferred. Y is a single bond or ester group, with a single bond being preferred.

Examples of the recurring units (a1) are shown below, but not limited thereto. $R^{31}$ and $R^{32}$ are as defined above.

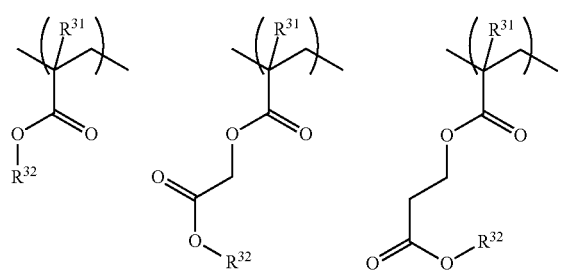

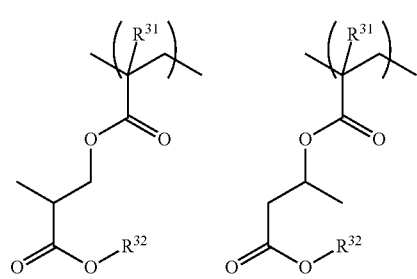

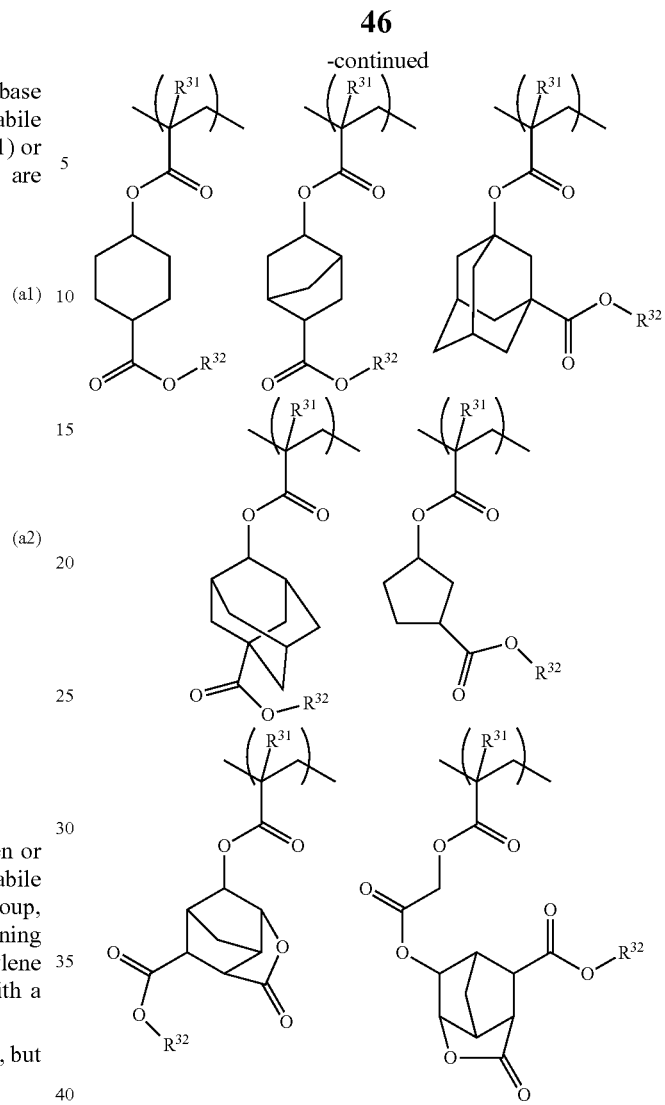

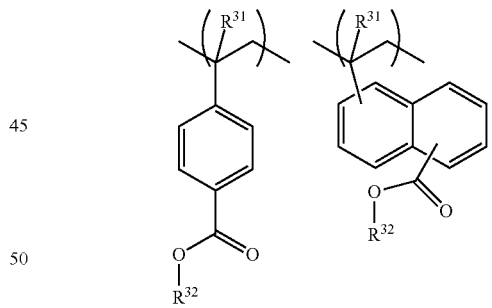

The acid labile groups represented by $R^{32}$ and $R^{34}$ in the recurring units (a1) and (a2) may be selected from a variety of such groups. The acid labile groups may be the same or different and include those groups described in JP-A 2013-080033 (U.S. Pat. No. 8,574,817) and JP-A 2013-083821 (U.S. Pat. No. 8,846,303), for example. The preferred acid labile groups include groups of the following formulae (AL-1) to (AL-3).

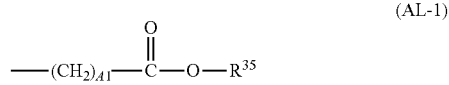

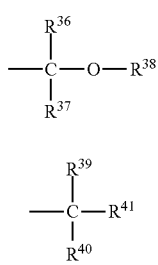

(AL-2)

(AL-3)

In formulae (AL-1) and (AL-2), $R^{35}$ and $R^{38}$ are each independently a $C_1$-$C_{40}$, preferably $C_1$-$C_{20}$ monovalent hydrocarbon group, typically straight, branched or cyclic alkyl, which may contain a heteroatom such as oxygen, sulfur, nitrogen or fluorine. $R^{36}$ and $R^{37}$ are each independently hydrogen or a $C_1$-$C_{20}$ monovalent hydrocarbon group, typically straight, branched or cyclic alkyl, which may contain a heteroatom such as oxygen, sulfur, nitrogen or fluorine. A1 is an integer of 0 to 10, especially 1 to 5. A pair of and $R^{37}$, $R^{36}$ and $R^{98}$, or $R^{37}$ and $R^{38}$ may bond together to form a ring, typically alicyclic, with the carbon atom or carbon and oxygen atoms to which they are attached, the ring containing 3 to 20 carbon atoms, preferably 4 to 16 carbon atoms.

In formula (AL-3), $R^{39}$, $R^{40}$ and $R^{41}$ are each independently a $C_1$-$C_{20}$ monovalent hydrocarbon group, typically straight, branched or cyclic alkyl, which may contain a heteroatom such as oxygen, sulfur, nitrogen or fluorine. A pair of $R^{39}$ and $R^{40}$, $R^{39}$ and $R^{41}$, or $R^{40}$ and $R^{41}$ may bond together to form a ring, typically alicyclic, with the carbon atom to which they are attached, the ring containing 3 to 20 carbon atoms, preferably 4 to 16 carbon atoms.

The base polymer may further comprise recurring units (b) having a phenolic hydroxyl group as an adhesive group. Examples of suitable monomers from which recurring units (b) are derived are given below, but not limited thereto.

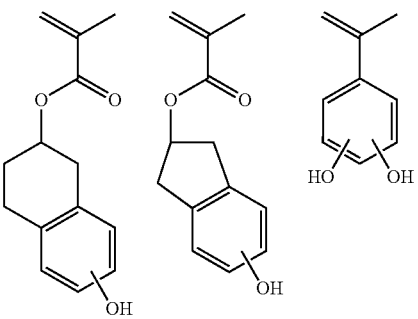

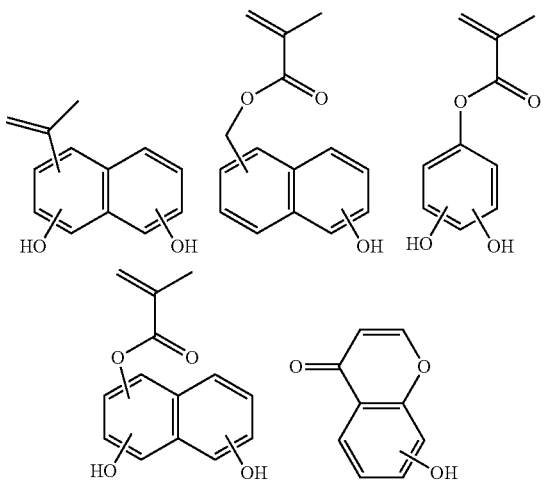

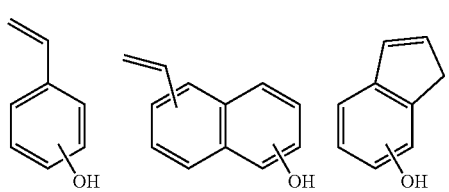

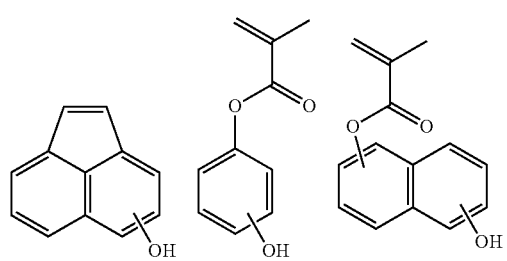

Further, recurring units (c) having another adhesive group selected from hydroxyl (other than phenolic hydroxyl), lactone ring, ether, ester, carbonyl and cyano groups may also be incorporated in the base polymer. Examples of suitable monomers from which recurring units (c) are derived are given below, but not limited thereto.

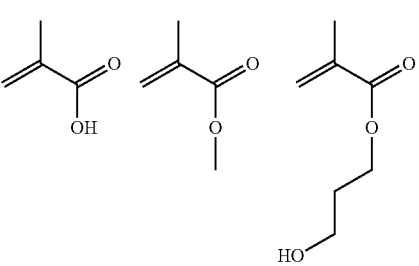

49
-continued
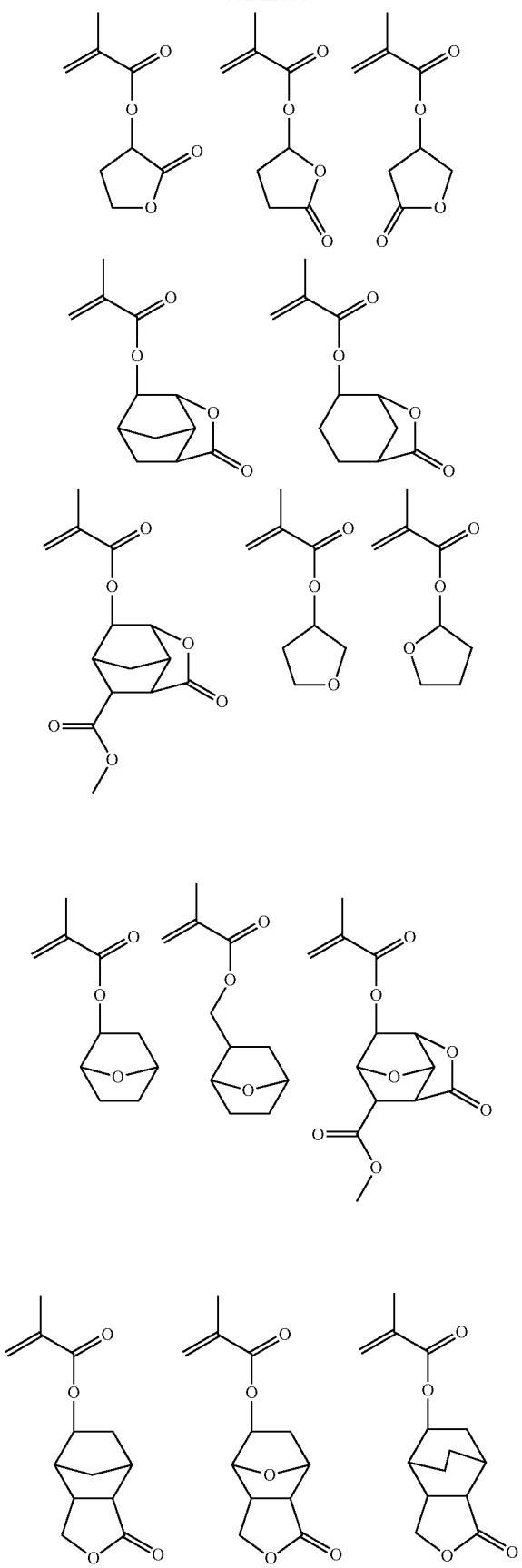
50
-continued
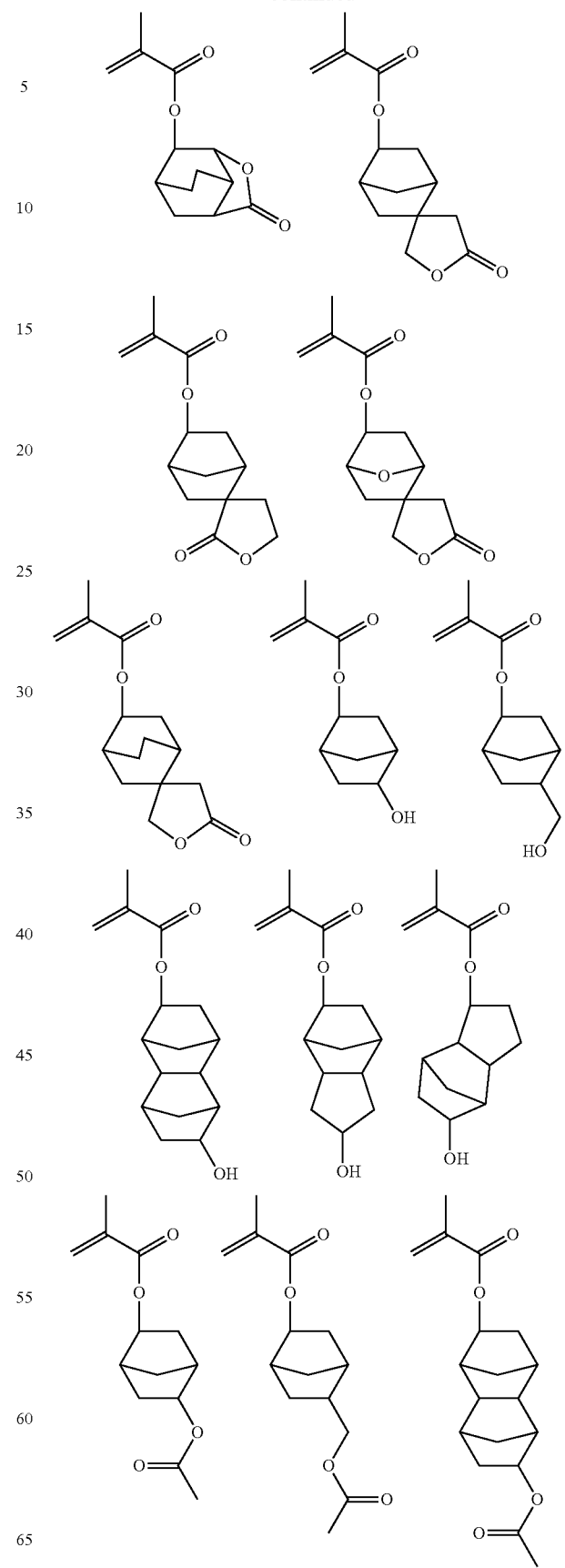

51
-continued
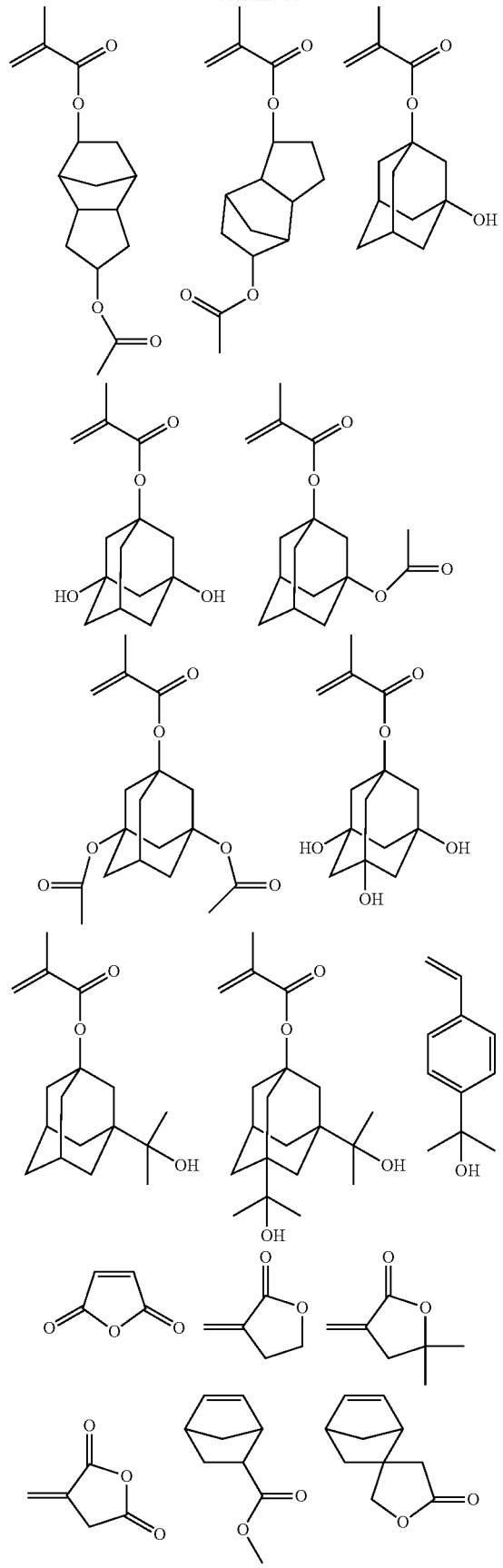
52
-continued
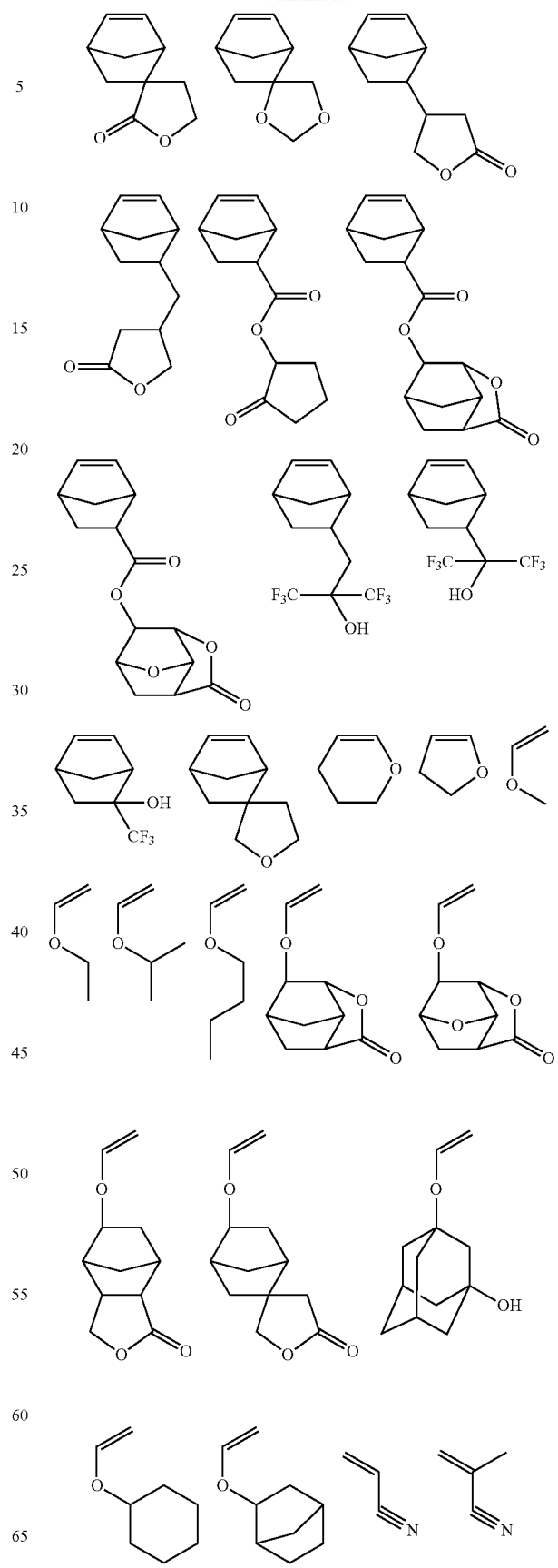

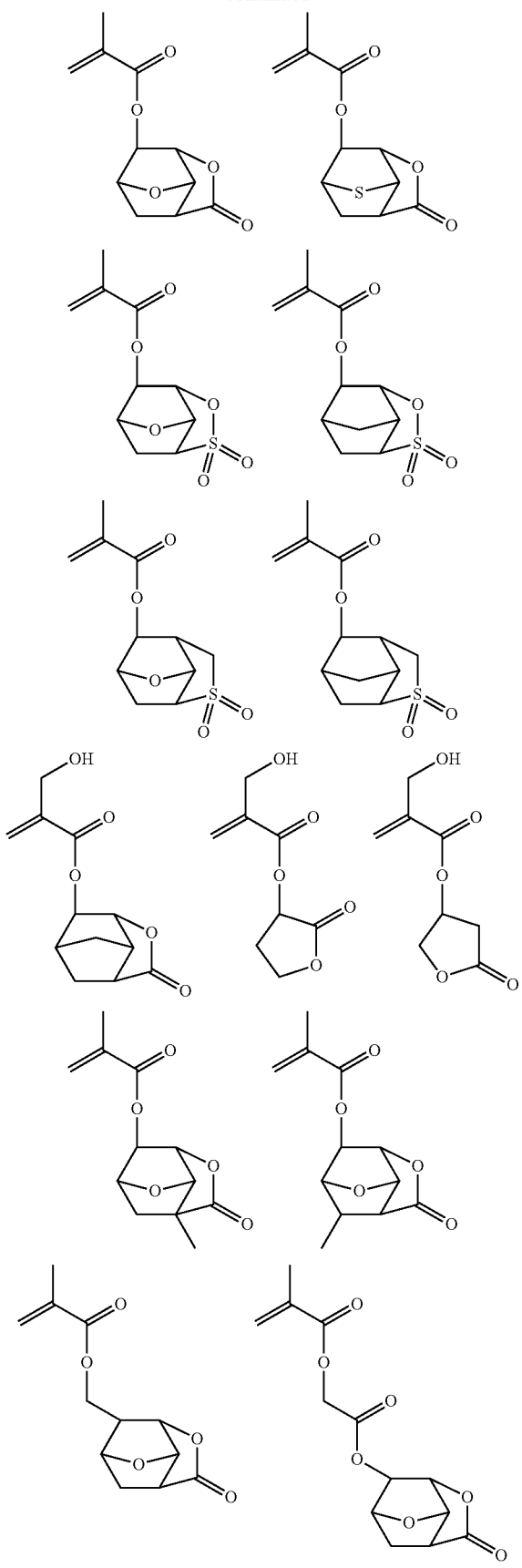
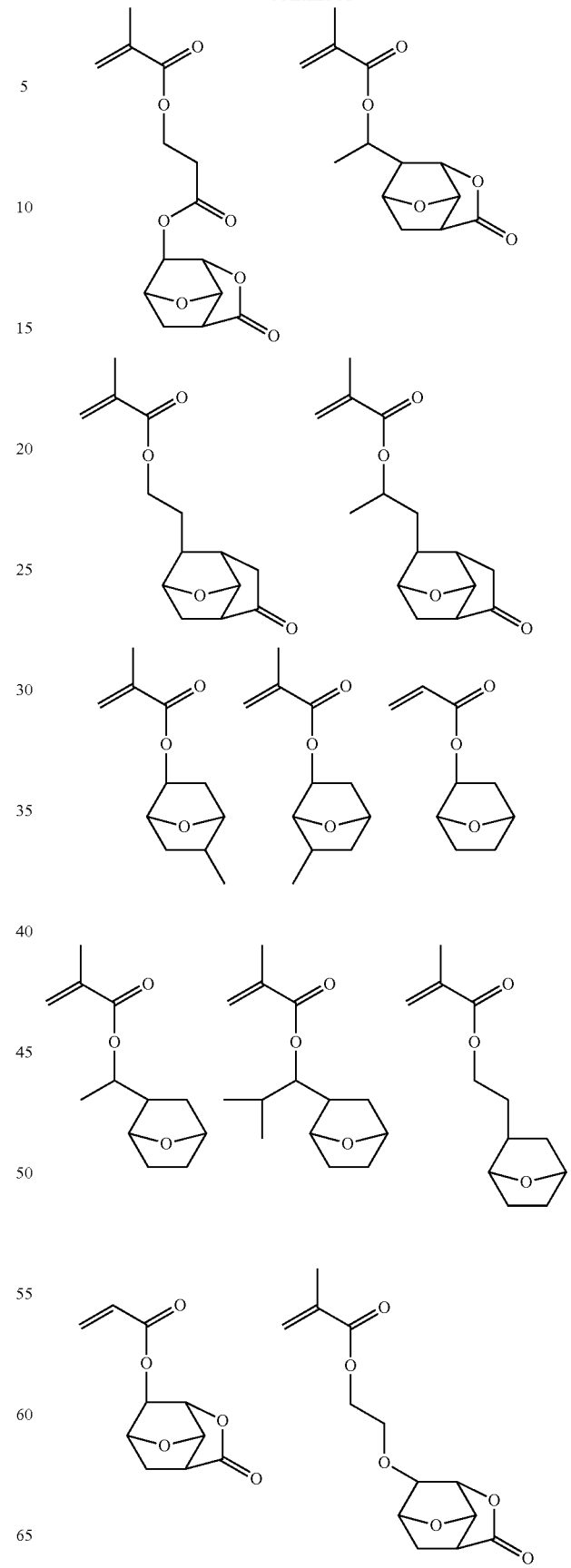

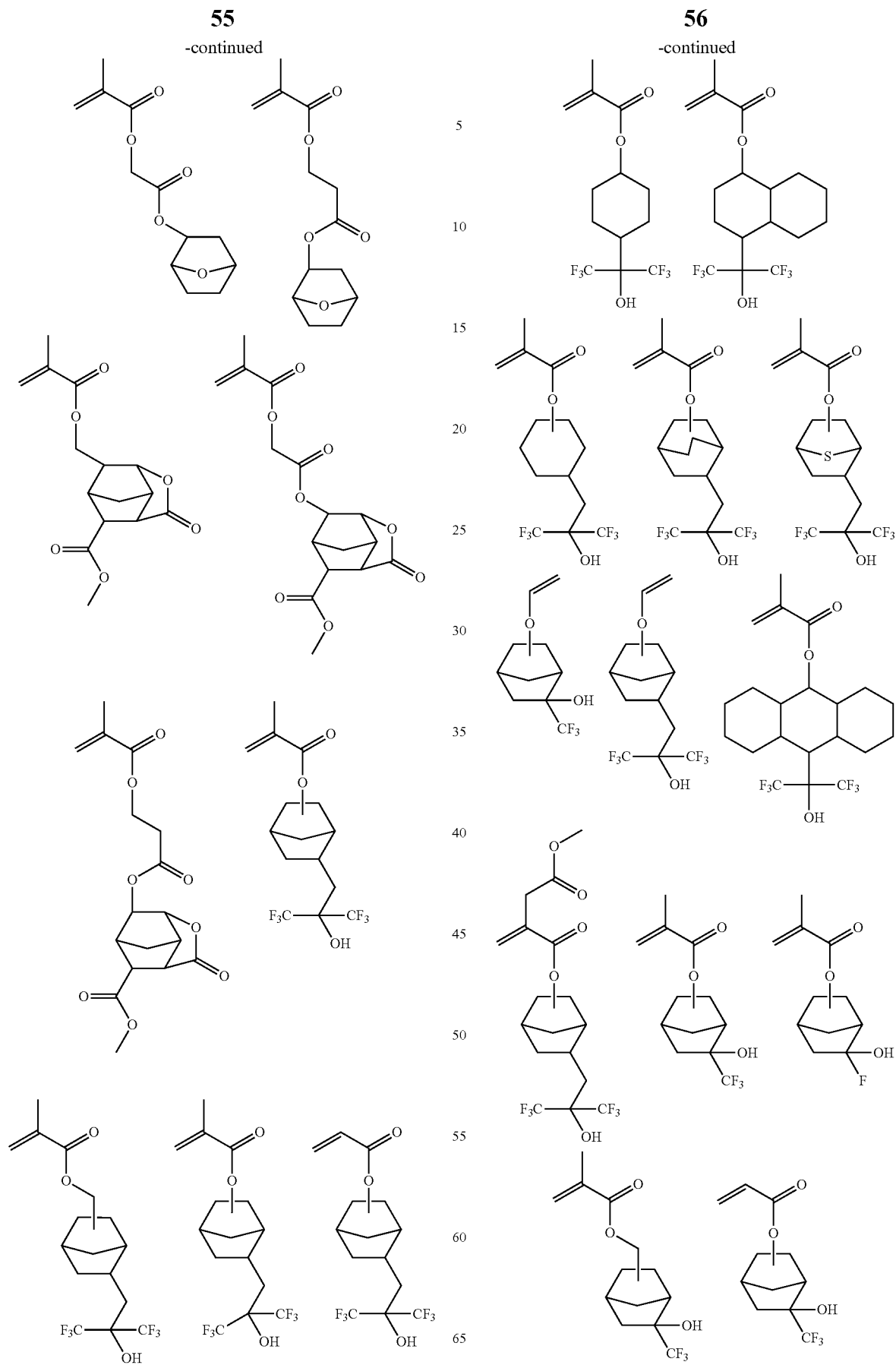

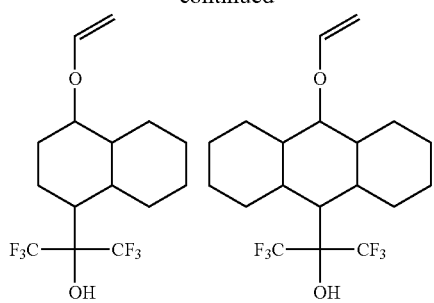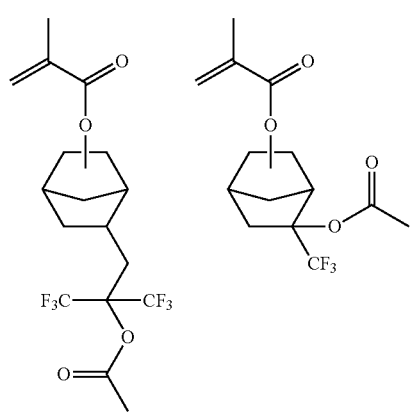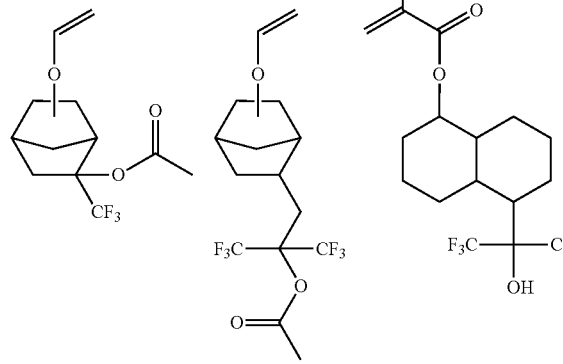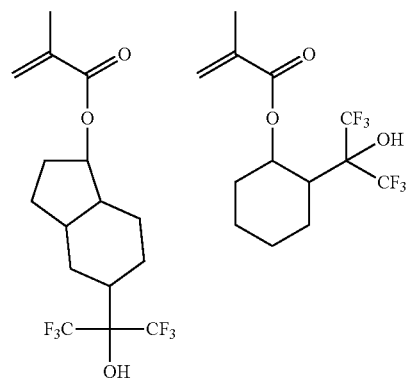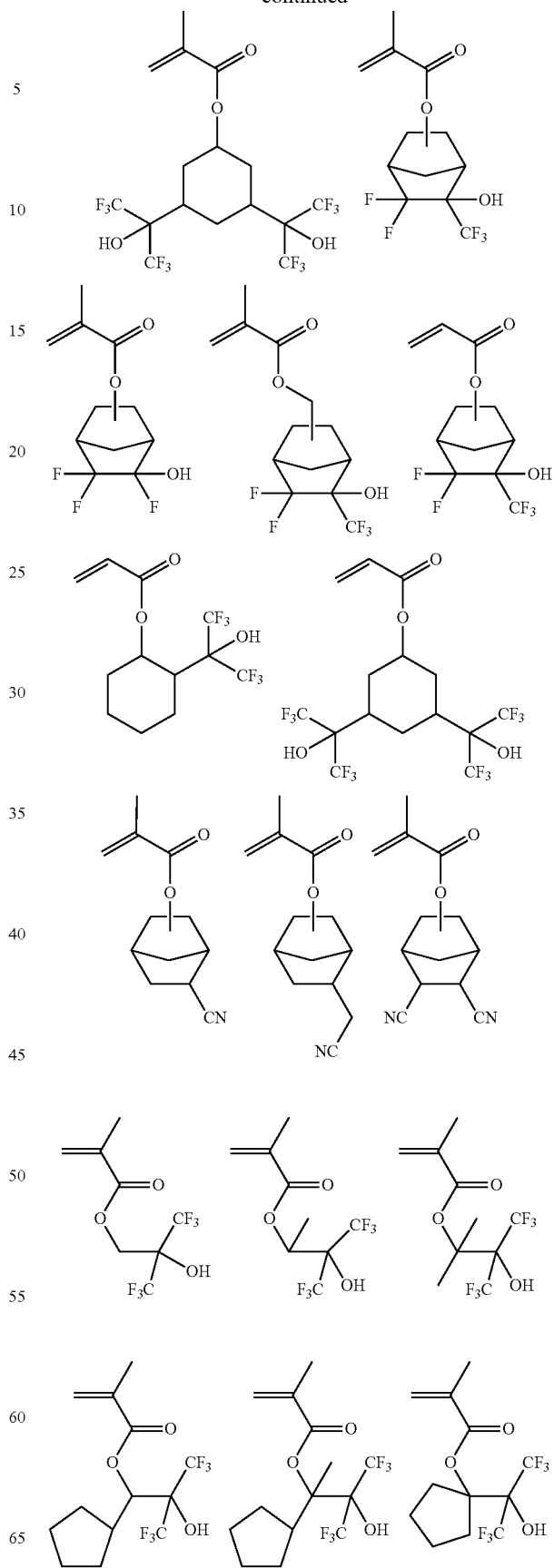

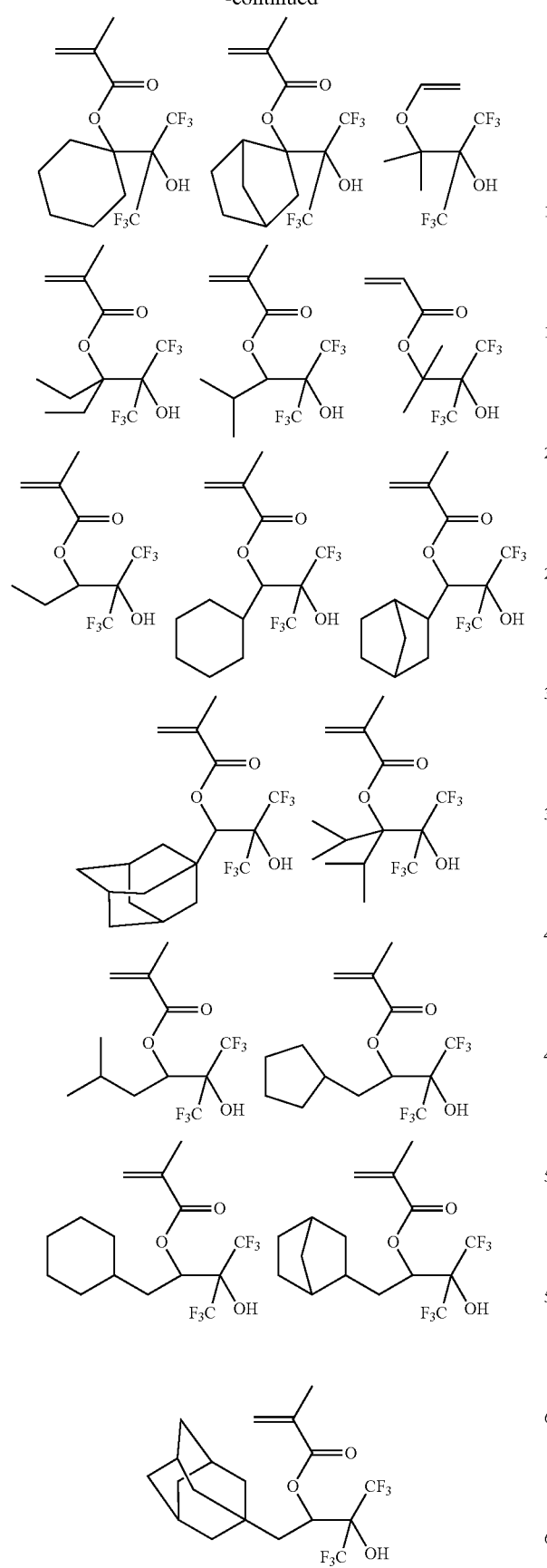
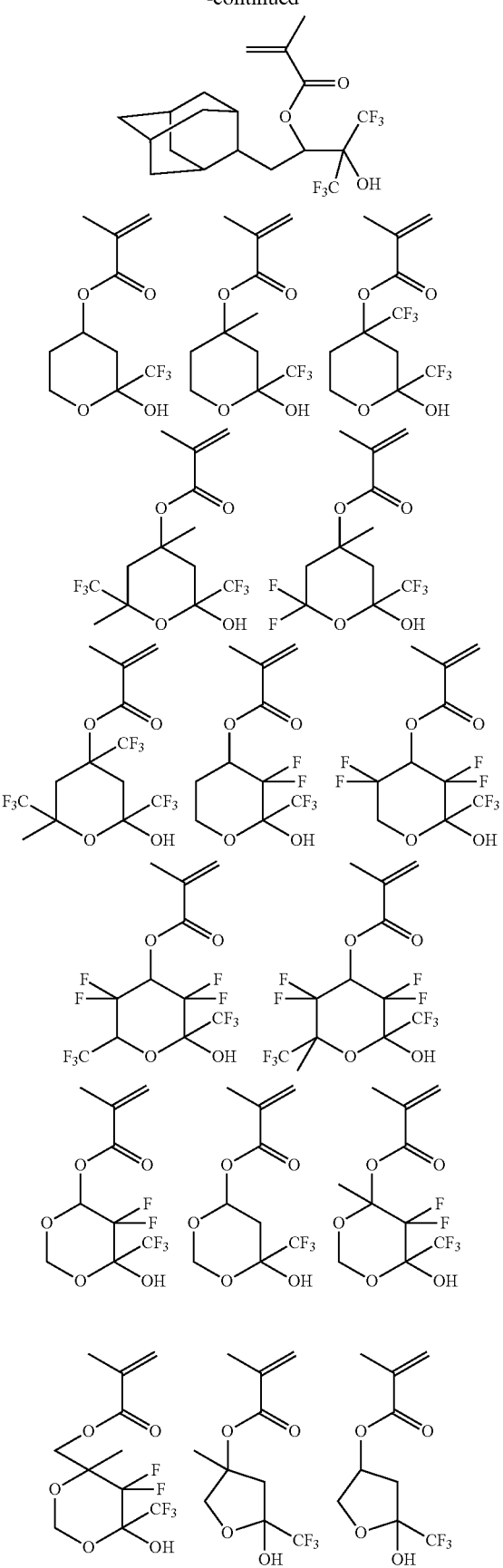

61
-continued
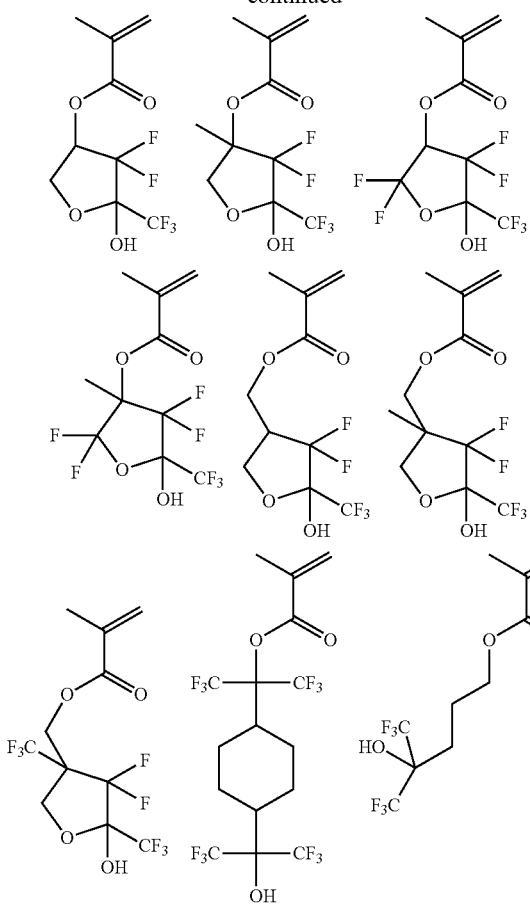
62
-continued
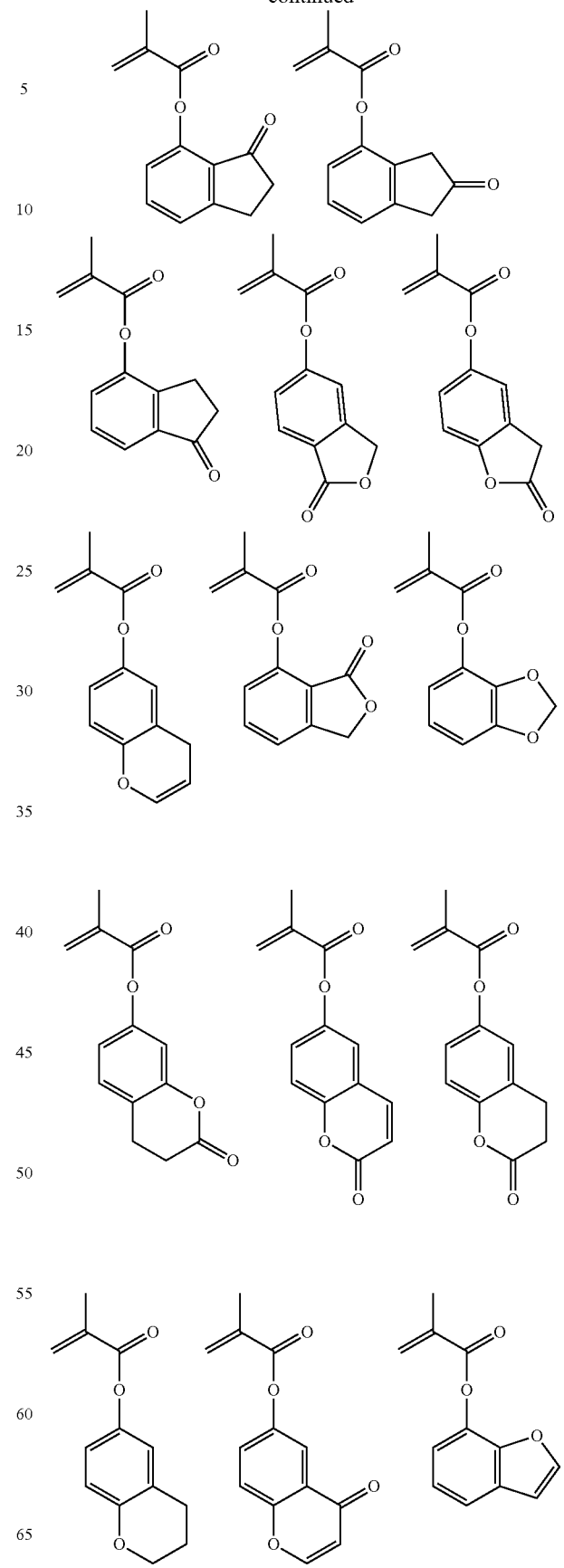

63
-continued
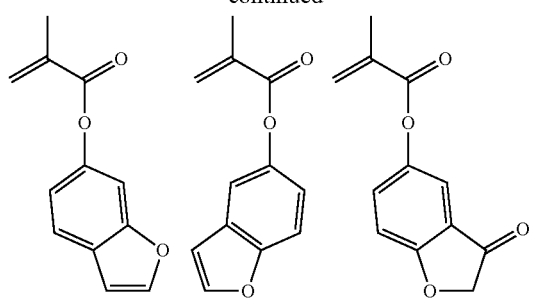
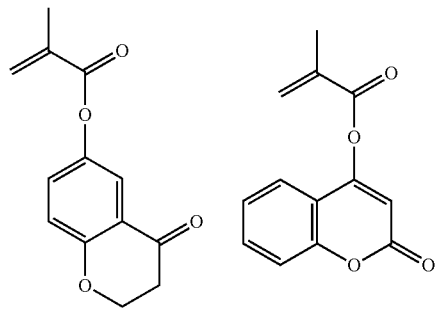
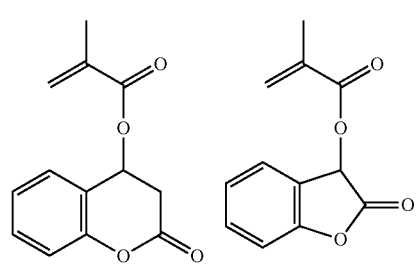
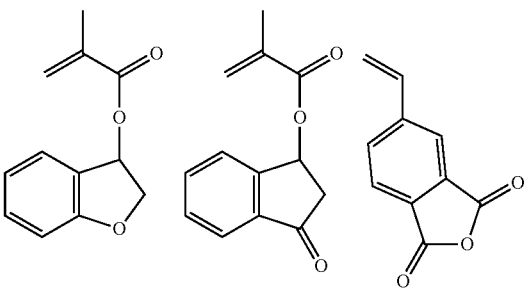
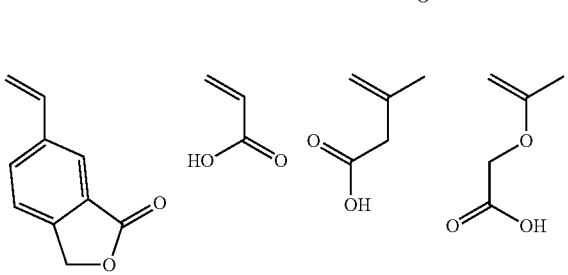
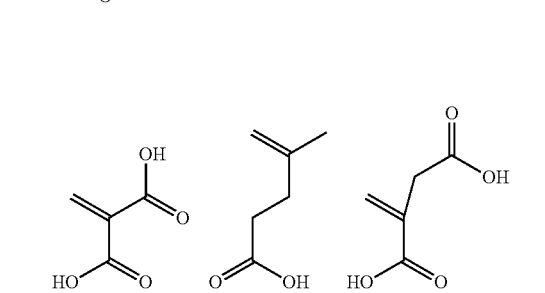
64
-continued
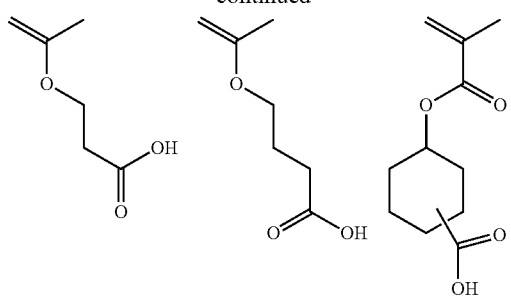
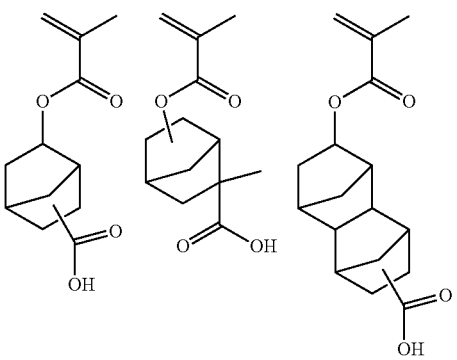
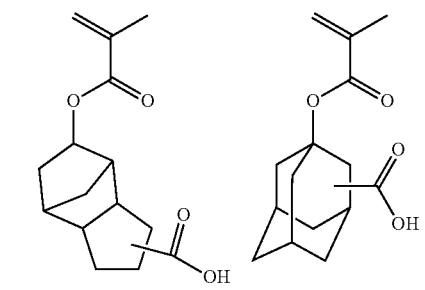
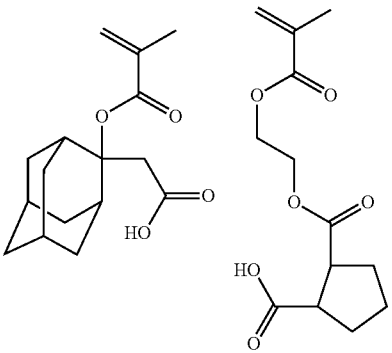
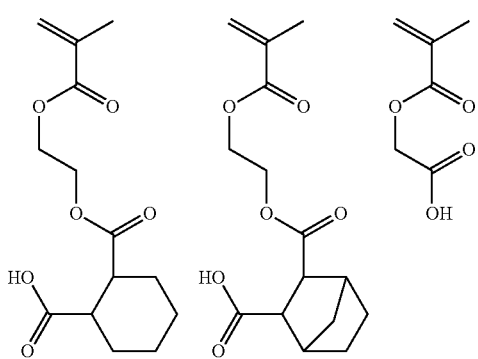

-continued

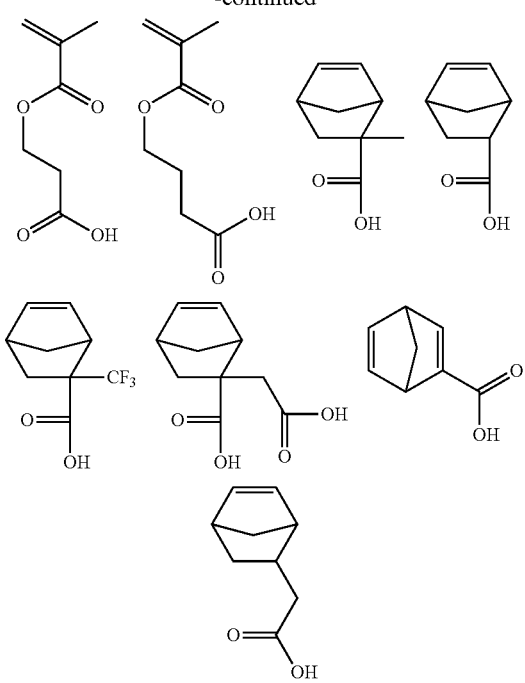

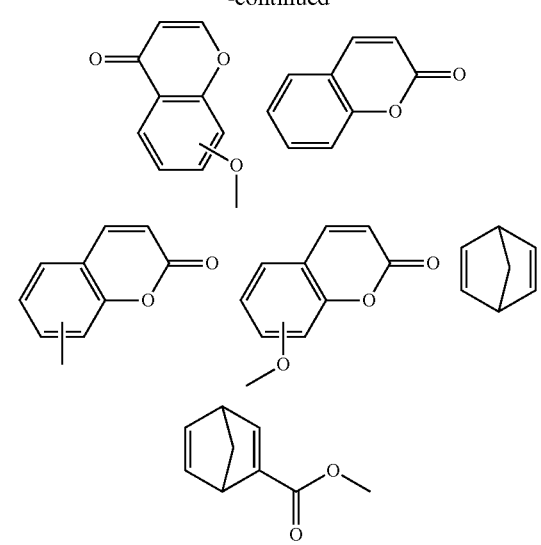

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

In another preferred embodiment, the base polymer may further comprise recurring units (d) selected from units of indene, benzofuran, benzothiophene, acenaphthylene, chromone, coumarin, and norbornadiene, or derivatives thereof. Suitable monomers are exemplified below.

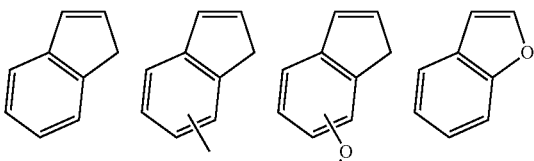

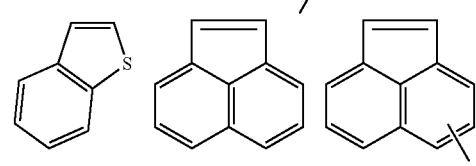

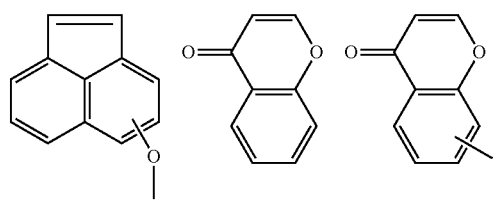

Besides the recurring units described above, further recurring units (e) may be incorporated in the base polymer, examples of which include styrene, vinylnaphthalene, vinylanthracene, vinylpyrene, methyleneindene, vinylpyridine, and vinylcarbazole.

In a further embodiment, recurring units (f) derived from an onium salt having a polymerizable carbon-carbon double bond may be incorporated in the base polymer. JP-A 2005-084365 discloses sulfonium and iodonium salts having a polymerizable carbon-carbon double bond capable of generating a sulfonic acid. JP-A 2006-178317 discloses a sulfonium salt having sulfonic acid directly attached to the main chain.

In a preferred embodiment, the base polymer may further comprise recurring units of at least one type selected from formulae (f1), (f2) and (f3). These units are simply referred to as recurring units (f1), (f2) and (f3), which may be used alone or in combination of two or more types.

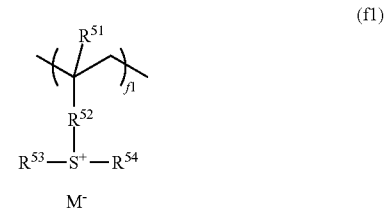

(f1)

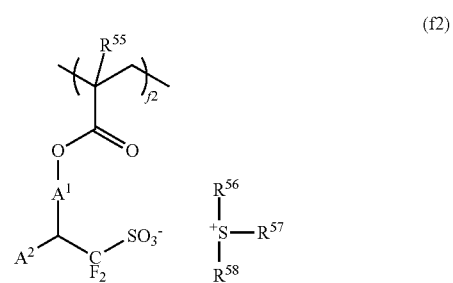

(f2)

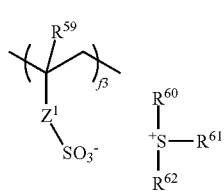
(f3)

Herein $R^{51}$, $R^{55}$ and $R^{59}$ each are hydrogen or methyl. $R^{52}$ is a single bond, phenylene, —O—$R^{63}$—, or —C(=O)—$Y^1$—$R^{63}$—, wherein $Y^1$ is —O— or —NH—, and $R^{63}$ is a $C_1$-$C_6$ straight, branched or cyclic alkylene or alkenylene group which may contain a carbonyl, ester, ether or hydroxyl moiety, or phenylene group. $R^{53}$, $R^{54}$, $R^{56}$, $R^{57}$, $R^{58}$, $R^{60}$, $R^{61}$, and $R^{62}$ are each independently a $C_1$-$C_{12}$ straight, branched or cyclic alkyl group which may contain a carbonyl, ester or ether moiety, or a $C_6$-$C_{12}$ aryl group, $C_7$-$C_{20}$ aralkyl group or mercaptophenyl group. $A^1$ is a single bond, -$A^0$-C(=O)—O—, -$A^0$-O— or -$A^0$-O—C(=O)—, wherein $A^0$ is a $C_1$-$C_{12}$ straight, branched or cyclic alkylene group which may contain a carbonyl, ester or ether moiety. $A^2$ is hydrogen or trifluoromethyl. $Z^1$ is a single bond, methylene, ethylene, phenylene, fluorinated phenylene, —O—$R^{64}$—, or —C(=O)—$Z^2$—$R^{64}$—, wherein $Z^2$ is —O— or —NH—, and $R^{64}$ is a $C_1$-$C_6$ straight, branched or cyclic alkylene or alkenylene group which may contain a carbonyl, ester, ether or hydroxyl moiety, or phenylene, fluorinated phenylene or trifluoromethyl-substituted phenylene group. $M^-$ is a non-nucleophilic counter ion, and f1, f2 and f3 are numbers in the range: 0≤f1≤0.5, 0≤f2≤0.5, 0≤f3≤0.5, and 0<f1+f2+f3≤0.5.

Examples of the monomer from which recurring unit (f1) is derived are shown below, but not limited thereto. $M^-$ is as defined above.

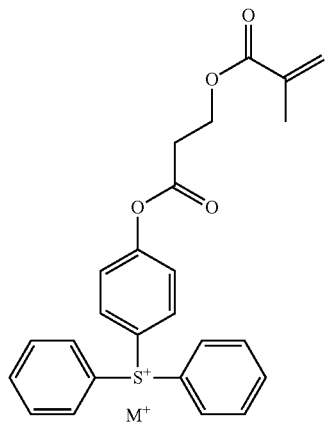

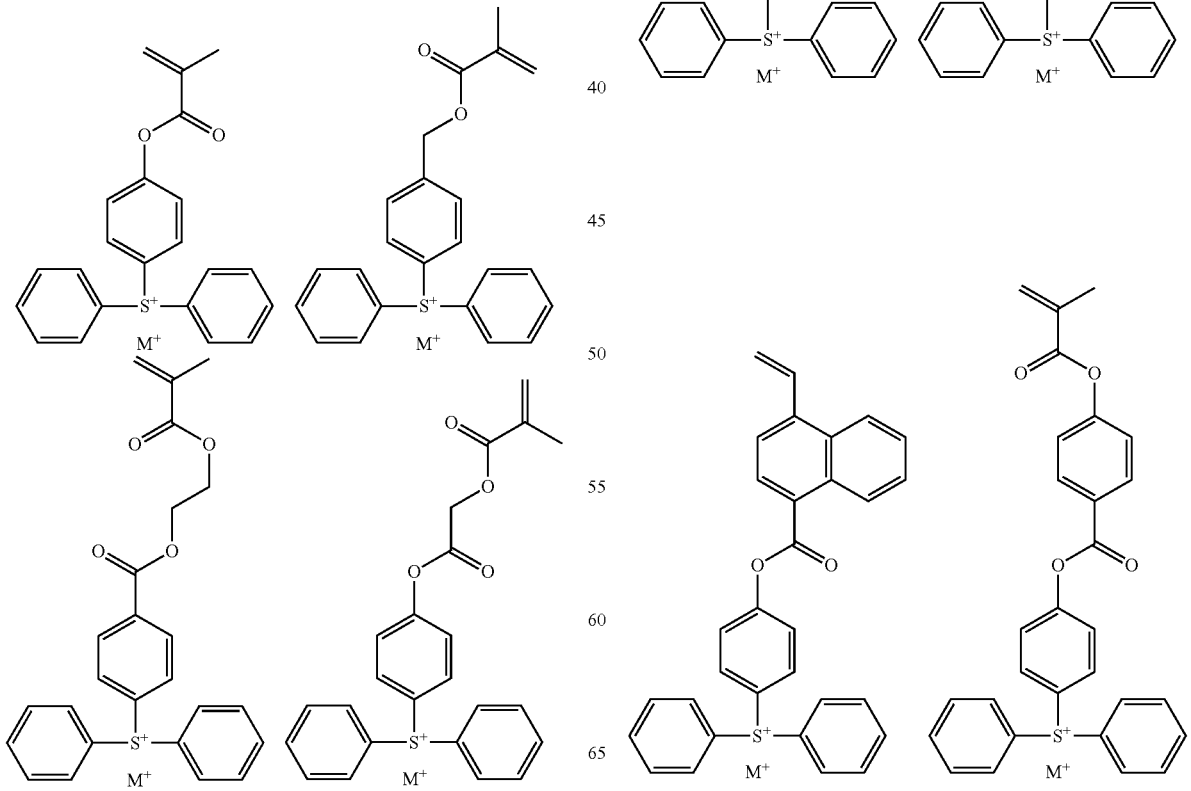

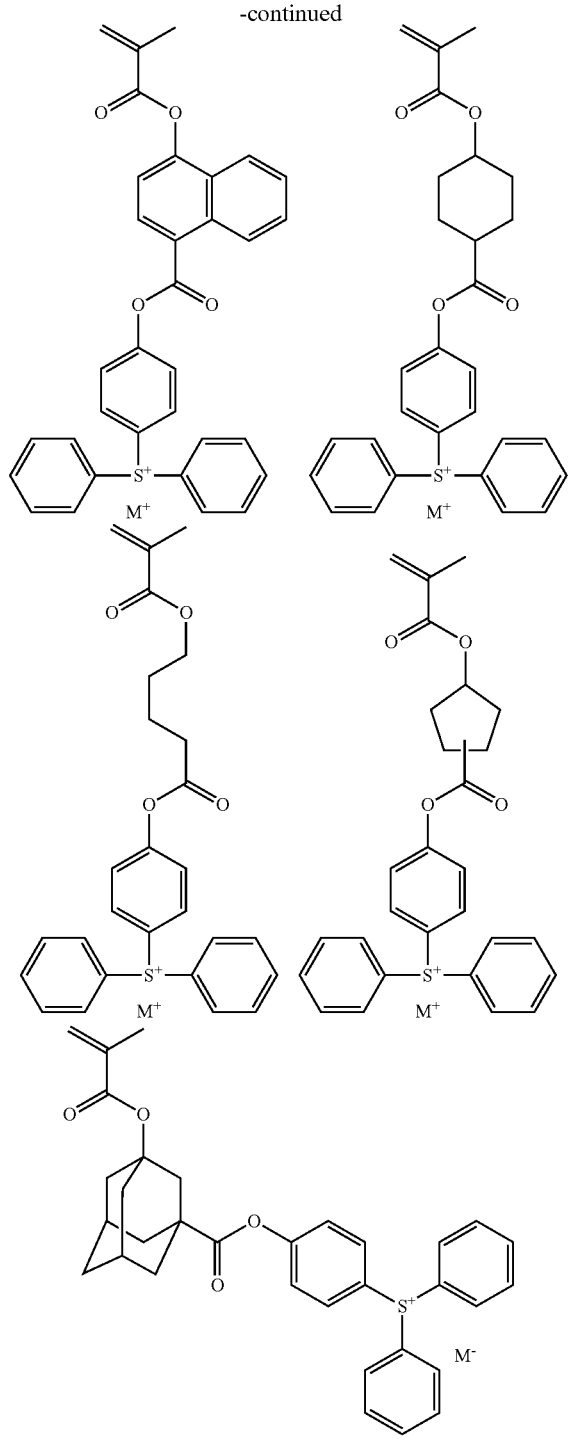

Also included are sulfonate ions having fluorine substituted at α-position as represented by the formula (K-1) and sulfonate ions having fluorine substituted at α- and β-positions as represented by the formula (K-2).

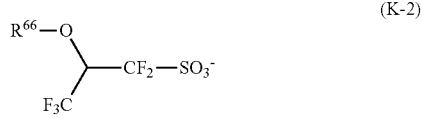

In formula (K-1), $R^{65}$ is hydrogen, or a $C_1$-$C_{20}$ straight, branched or cyclic alkyl group, $C_2$-$C_{20}$ straight, branched or cyclic alkenyl group, or $C_6$-$C_{20}$ aryl group, which may have an ether, ester, carbonyl moiety, lactone ring, or fluorine atom. In formula (K-2), $R^{66}$ is hydrogen, or a $C_1$-$C_{30}$ straight, branched or cyclic alkyl or acyl group, $C_2$-$C_{20}$ straight, branched or cyclic alkenyl group, or $C_6$-$C_{20}$ aryl or aryloxy group, which may have an ether, ester, carbonyl moiety or lactone ring.

Examples of the monomer from which recurring unit (f2) is derived are shown below, but not limited thereto.

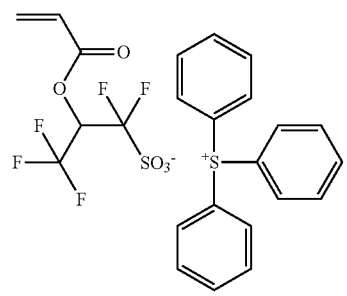
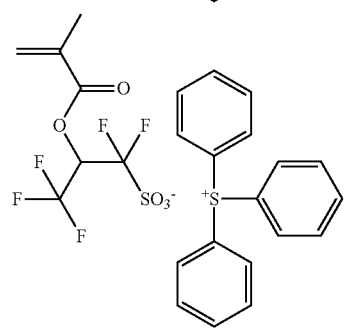
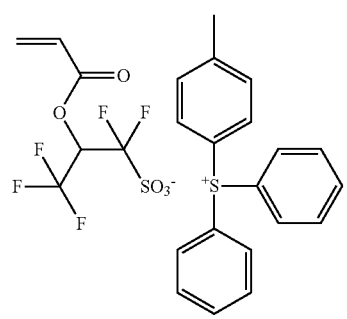

Examples of the non-nucleophilic counter ion M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; sulfonimides such as bis(trifluoromethylsulfonyl)imide, bis(perfluoroethylsulfonyl)imide and bis(perfluorobutylsulfonyl)imide; sulfonmethides such as tris(trifluoromethylsulfonyl)methide and tris(perfluoroethylsulfonyl)methide.

71
-continued
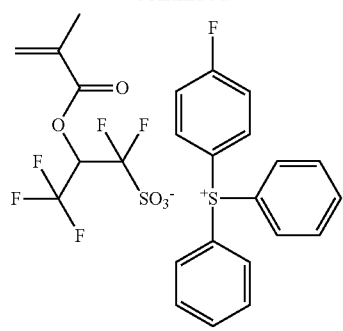
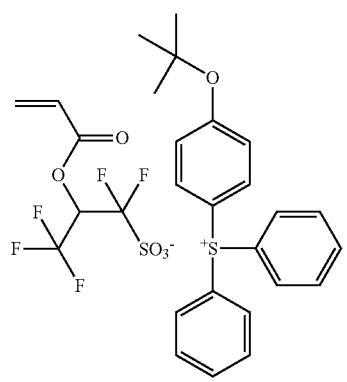
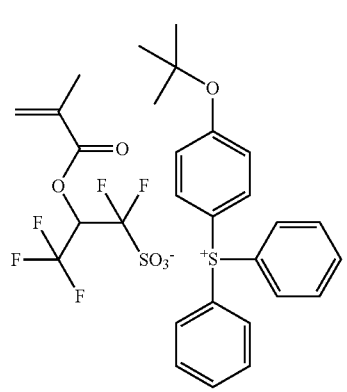
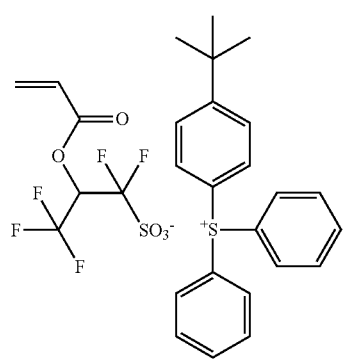
72
-continued
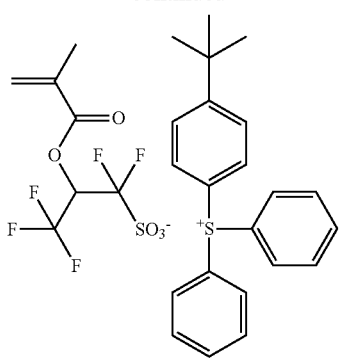
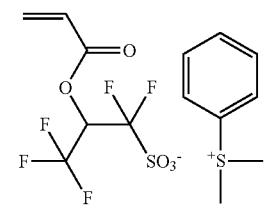
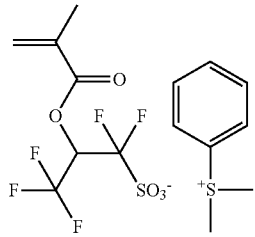
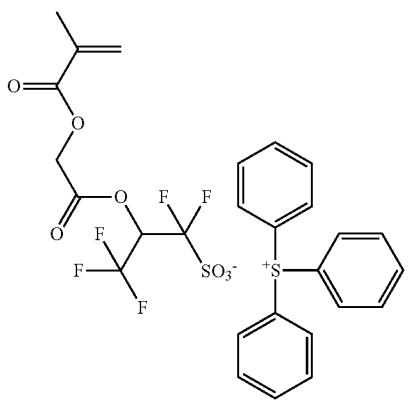
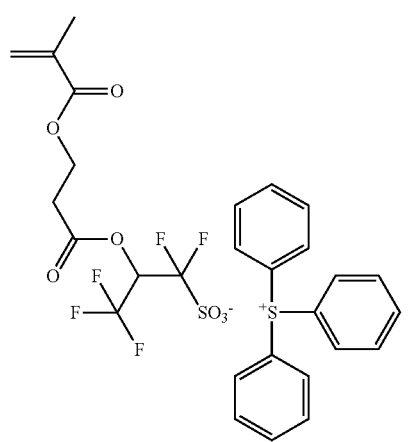

73
-continued
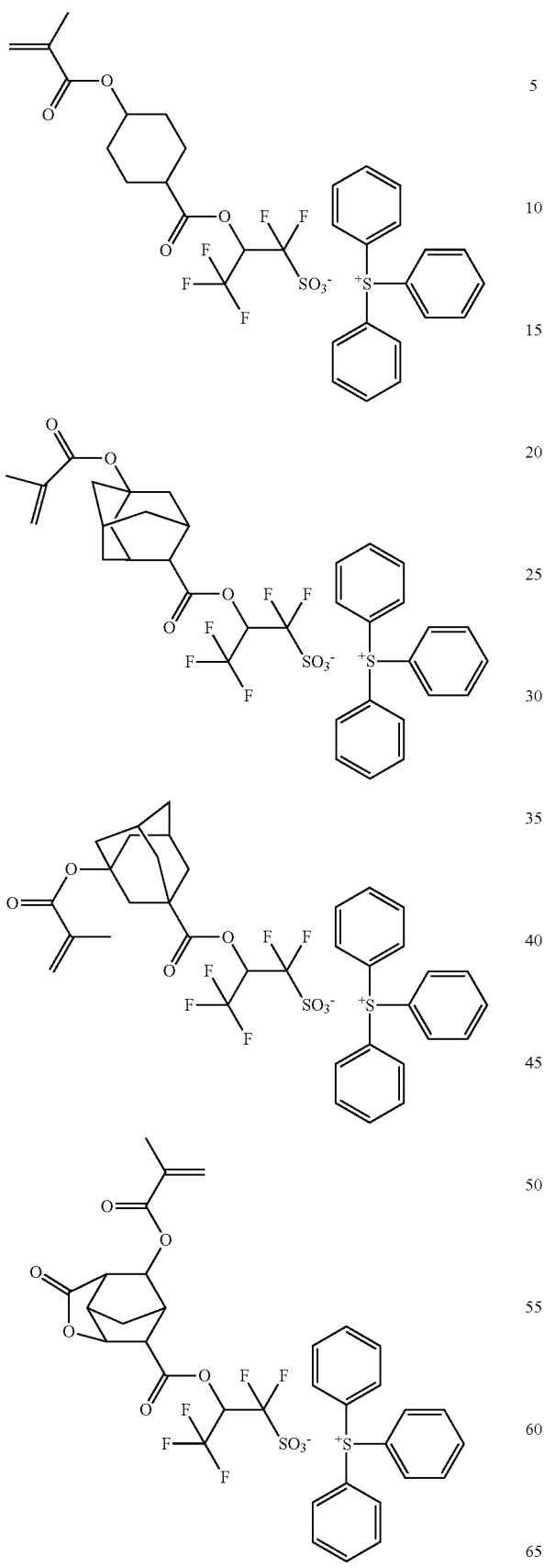
74
-continued
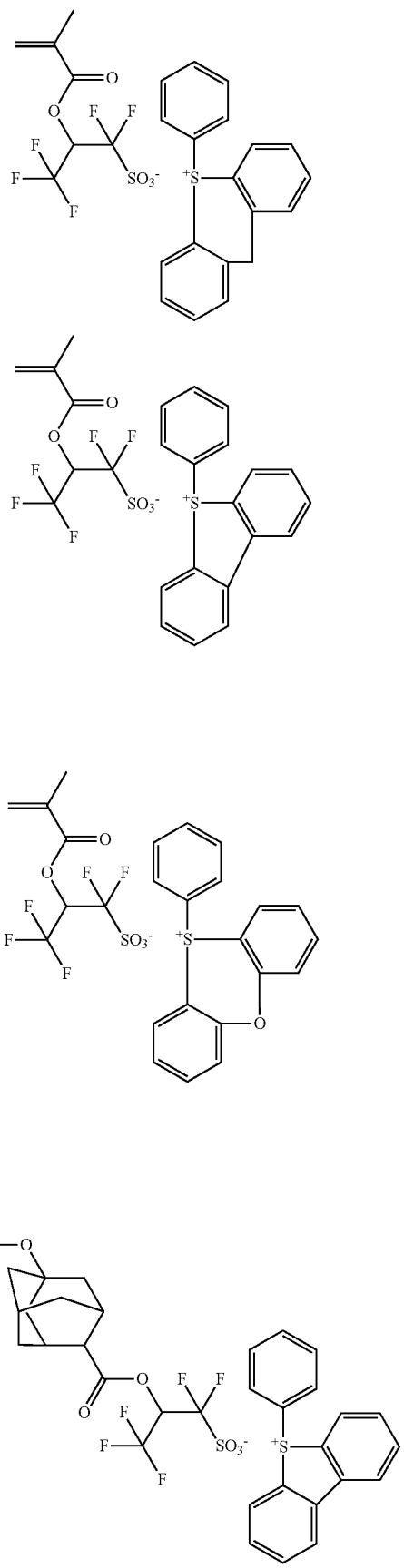

75
-continued
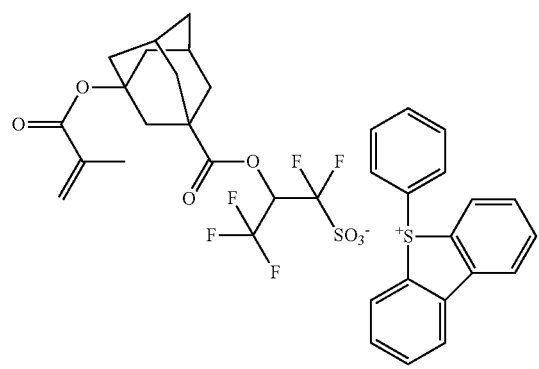
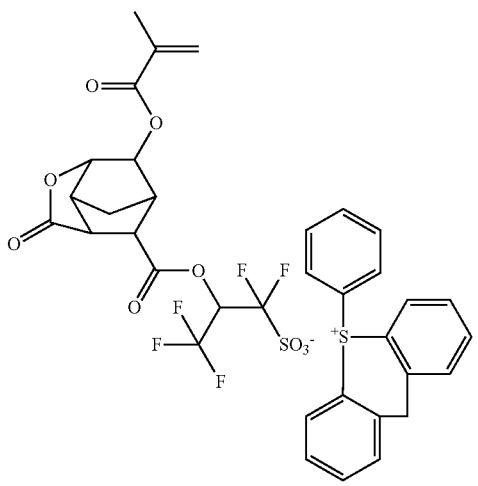
76
-continued
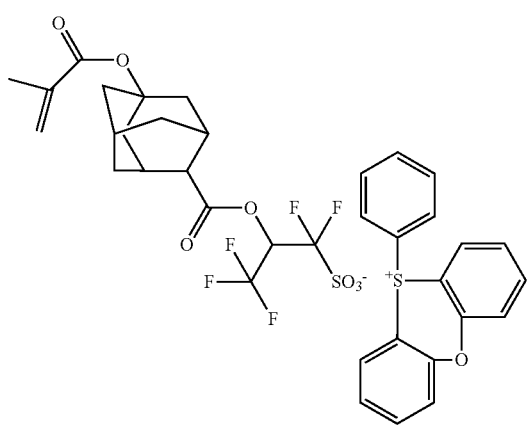
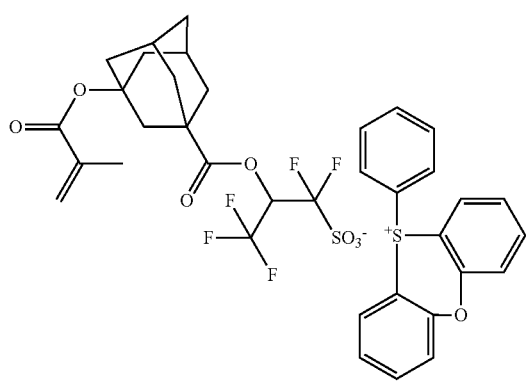

77
-continued
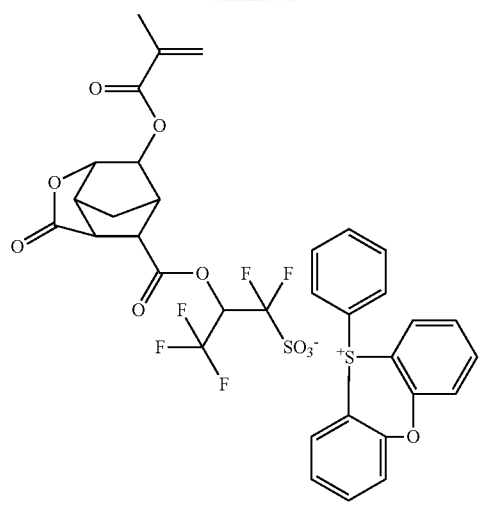
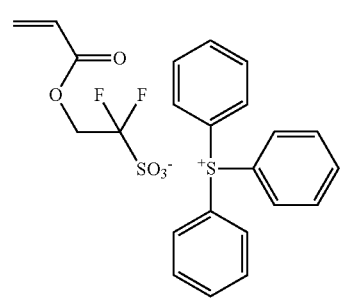
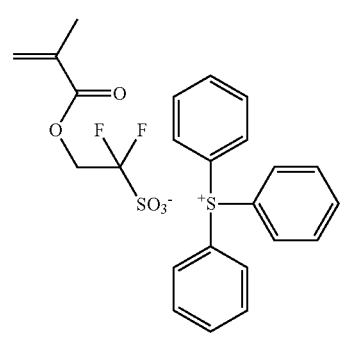
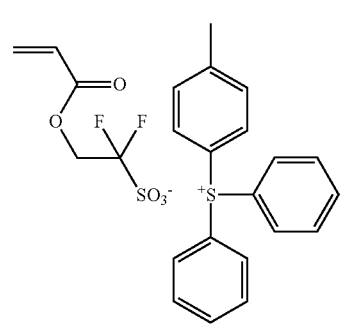
78
-continued
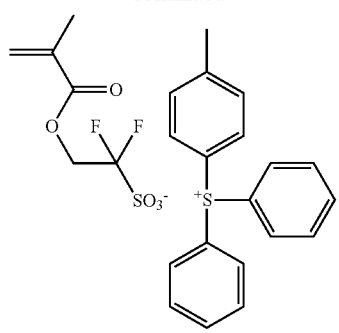
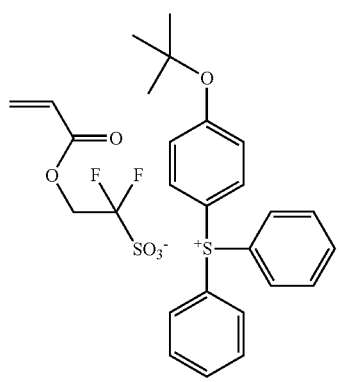
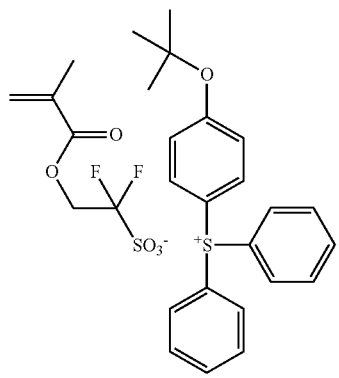
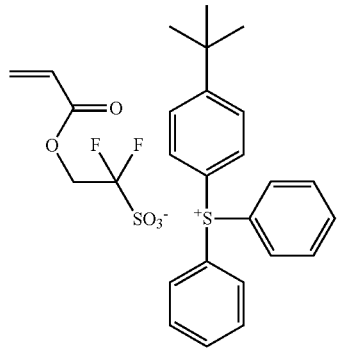

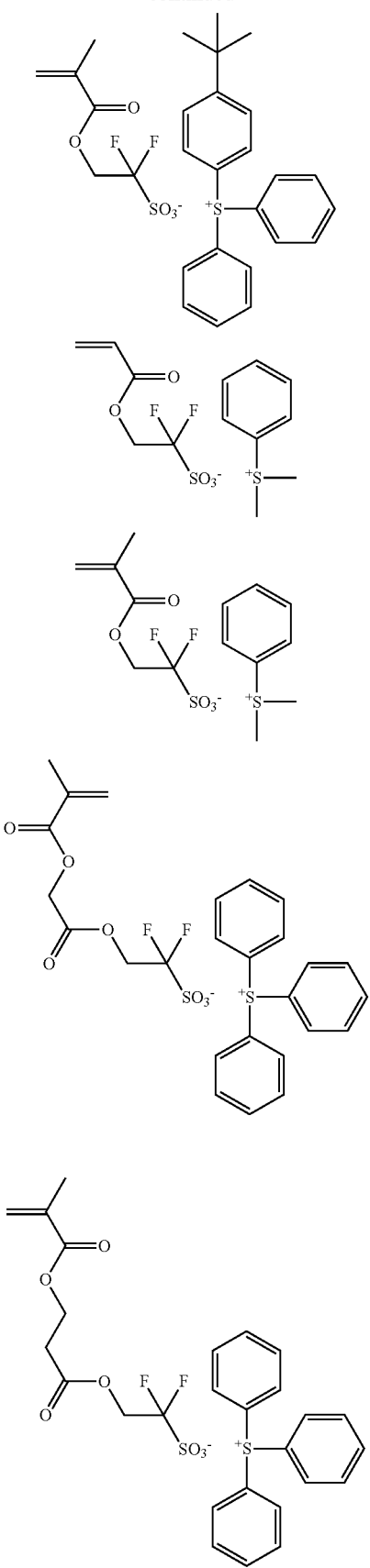
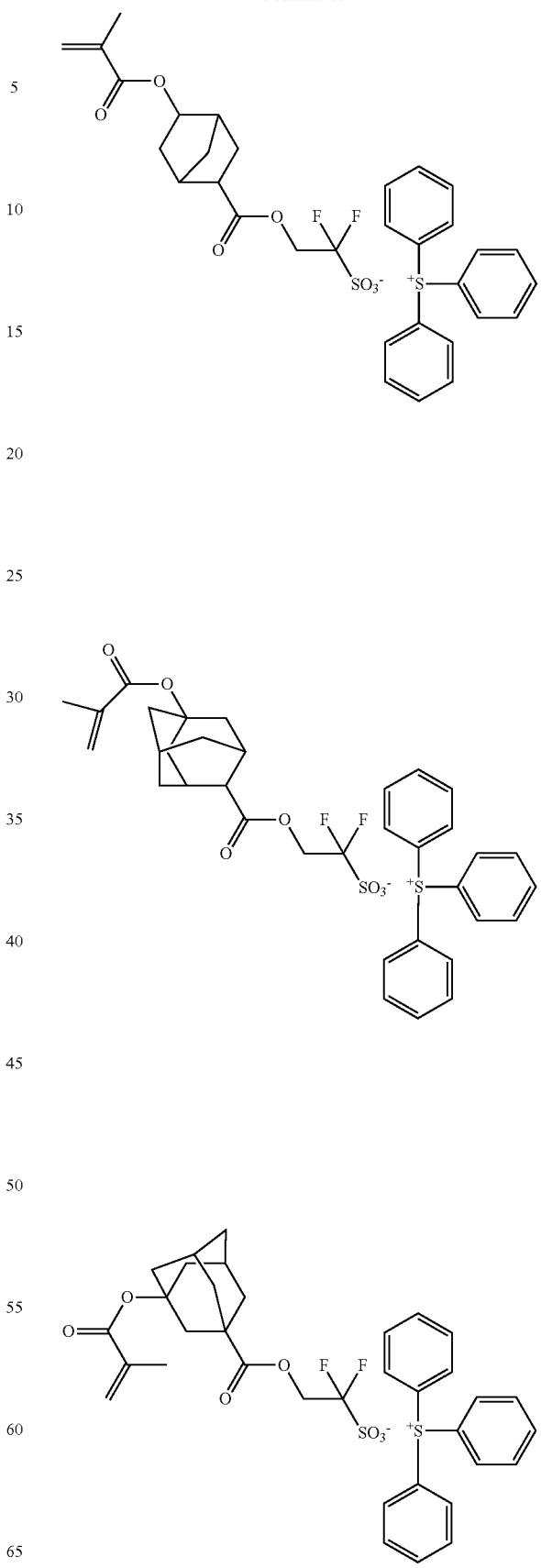

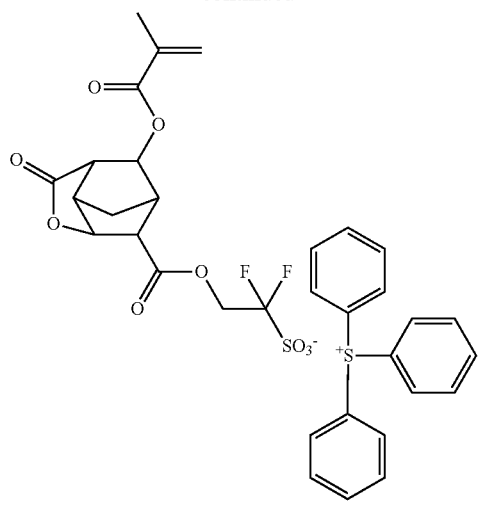
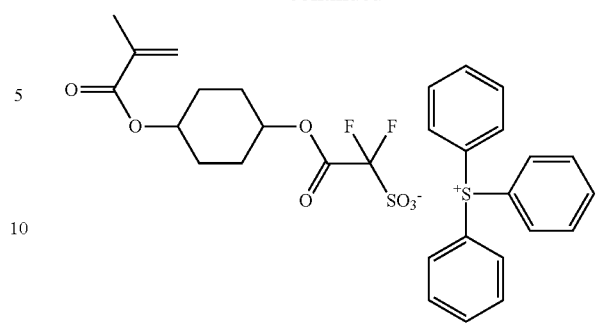
Examples of the monomer from which recurring unit (f3) is derived are shown below, but not limited thereto.
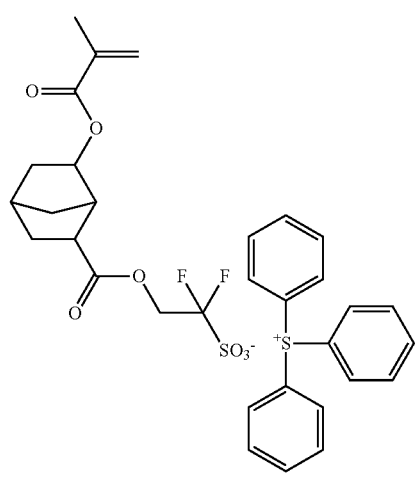
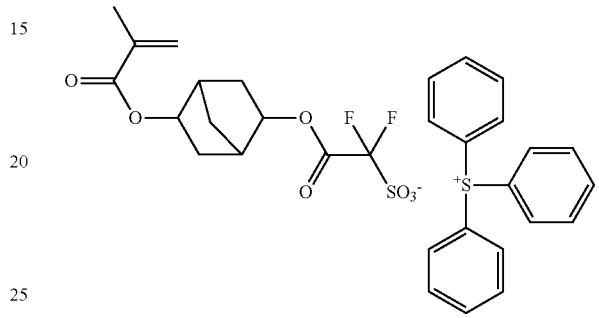
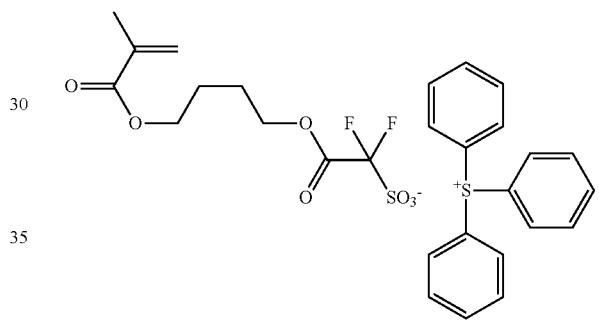
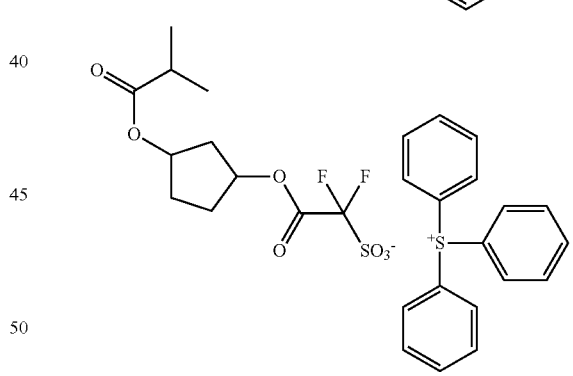
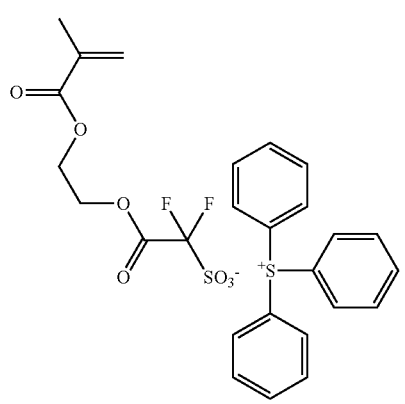
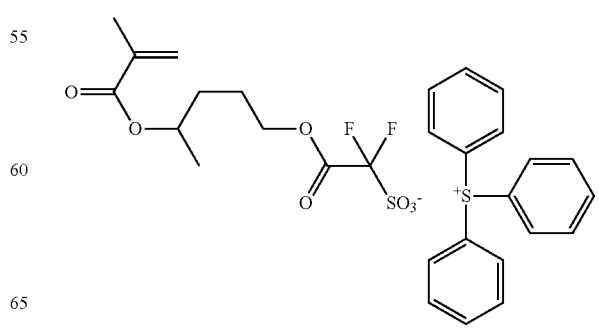

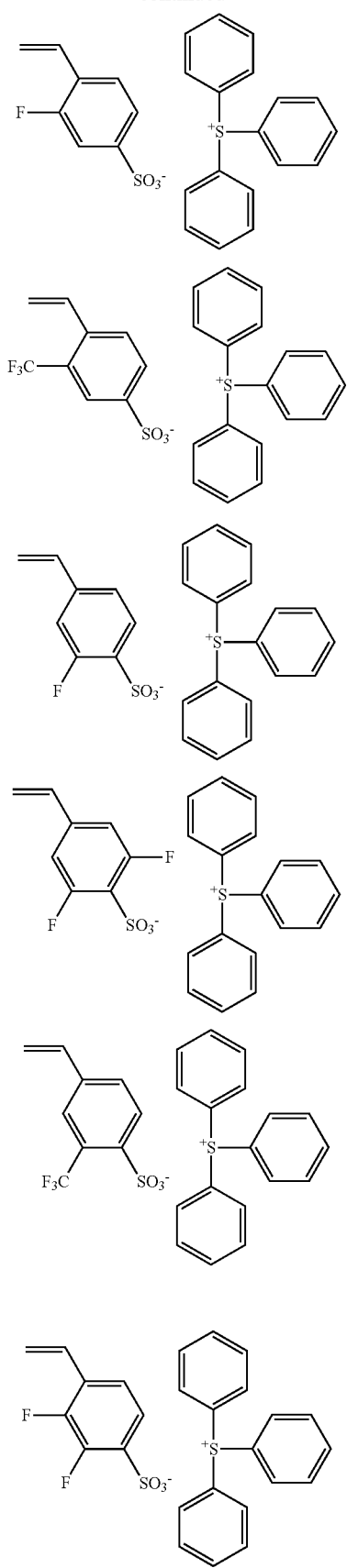
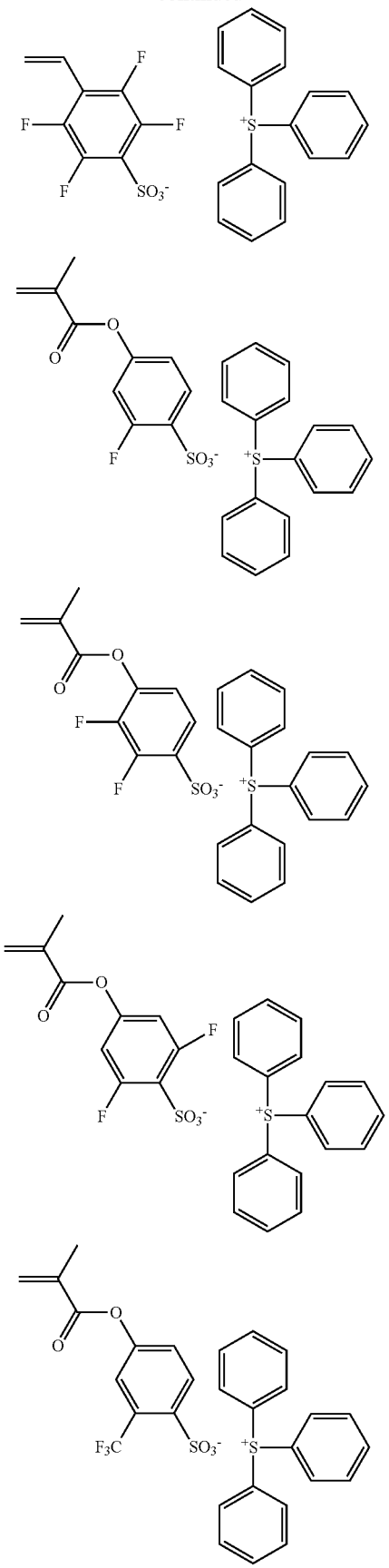

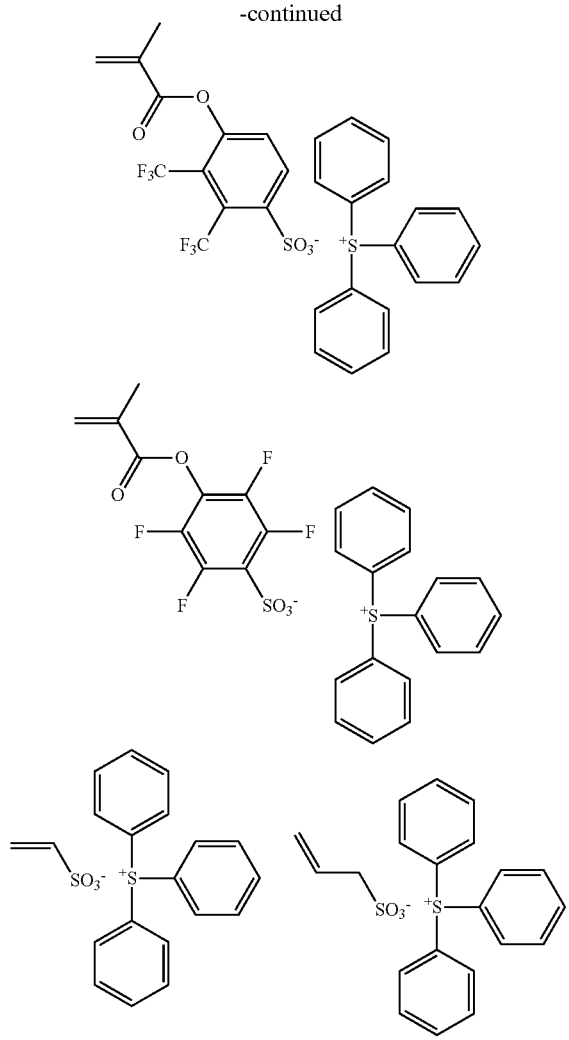

The attachment of an acid generator to the polymer main chain is effective in restraining acid diffusion, thereby preventing a reduction of resolution due to blur by acid diffusion. Also roughness (LWR) is improved since the acid generator is uniformly distributed. Where a base polymer containing recurring units of at least one type selected from recurring units (f1) to (f3) is used, the addition of a separate PAG may be omitted.

The base polymer for formulating the positive resist composition comprises recurring units (a1) or (a2) having an acid labile group as essential component and additional recurring units (b), (c), (d), (e), (f1), (f2) and (f3) as optional components. A fraction of units (a1), (a2), (b), (c), (d), (e), (f1), (f2) and (f3) is: preferably $0 \leq a1 < 1.0$, $0 \leq a2 < 1.0$, $0 < a1+a2 < 1.0$, $0 \leq b \leq 0.9$, $0 \leq c \leq 0.9$, $0 \leq d \leq 0.8$, $0 \leq e \leq 0.8$, $0 \leq f1 \leq 0.5$, $0 \leq f2 \leq 0.5$, and $0 \leq f3 \leq 0.5$; more preferably $0 \leq a1 \leq 0.9$, $0 \leq a2 \leq 0.9$, $0.1 \leq a1+a2 \leq 0.9$, $0 \leq b \leq 0.8$, $0 \leq c \leq 0.8$, $0 \leq d \leq 0.7$, $0 \leq e \leq 0.7$, $0 \leq f1 \leq 0.4$, $0 \leq f2 \leq 0.4$, and $0 \leq f3 \leq 0.4$; and even more preferably $0 \leq a1 \leq 0.8$, $0 \leq a2 \leq 0.8$, $0.1 \leq a1+a2 \leq 0.8$, $0 \leq b \leq 0.75$, $0 \leq c \leq 0.75$, $0 \leq d \leq 0.6$, $0 \leq e \leq 0.6$, $0 \leq f1 \leq 0.3$, $0 \leq f2 \leq 0.3$, and $0 \leq f3 \leq 0.3$. Note $a1+a2+b+c+d+e+f1+f2+f3=1.0$.

For the base polymer for formulating the negative resist composition, an acid labile group is not necessarily essential. The base polymer comprises recurring units (b), and optionally recurring units (c), (d), (e), (f1), (f2) and/or (f3). A fraction of these units is: $0<b \leq 1.0$, $0 \leq c \leq 0.9$, $0 \leq d \leq 0.8$, $0 \leq e \leq 0.8$, $0 \leq f1 \leq 0.5$, $0 \leq f2 \leq 0.5$, and $0 \leq f3 \leq 0.5$; preferably $0.2 \leq b \leq 1.0$, $0 \leq c \leq 0.8$, $0 \leq d \leq 0.7$, $0 \leq e \leq 0.7$, $0 \leq f1 \leq 0.4$, $0 \leq f2 \leq 0.4$, and $0 \leq f3 \leq 0.4$; and more preferably $0.3 \leq b \leq 1.0$, $0 \leq c \leq 0.75$, $0 \leq d \leq 0.6$, $0 \leq e \leq 0.6$, $0 \leq f1 \leq 0.3$, $0 \leq f2 \leq 0.3$, and $0 \leq f3 \leq 0.3$. Note $b+c+d+e+f1+f2+f3=1.0$.

The base polymer may be synthesized by any desired methods, for example, by dissolving one or more monomers selected from the monomers corresponding to the foregoing recurring units in an organic solvent, adding a radical polymerization initiator thereto, and effecting heat polymerization. Examples of the organic solvent which can be used for polymerization include toluene, benzene, tetrahydrofuran, diethyl ether and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis as mentioned above, for thereby converting the polymer product to hydroxystyrene or hydroxyvinylnaphthalene. For alkaline hydrolysis, a base such as aqueous ammonia or triethylamine may be used. The reaction temperature is −20° C. to 100° C., preferably 0° C. to 60° C., and the reaction time is 0.2 to 100 hours, preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran as a solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and dispersity become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Acid Generator

To the resist composition comprising the base polymer and the phosphazene salt compound having formula (A), an acid generator may be added so that the composition may function as a chemically amplified positive resist composition or chemically amplified negative resist composition. The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, sulfonimide or sulfonmethide are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, those having the formulae (1) and (2) are preferred.

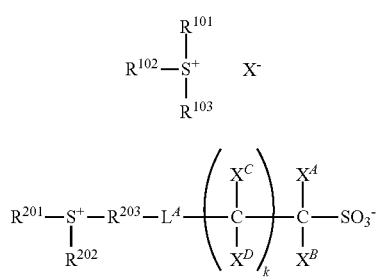

In formula (1), $R^{101}$, $R^{102}$ and $R^{103}$ are each independently a $C_1$-$C_{20}$ straight, branched or cyclic monovalent hydrocarbon group which may contain a heteroatom. Any two of $R^{101}$, $R^{102}$ and $R^{103}$ may bond together to form a ring with the sulfur atom to which they are attached.

In formula (1), $X^-$ is an anion of the following formula (1A), (1B), (1C) or (1D).

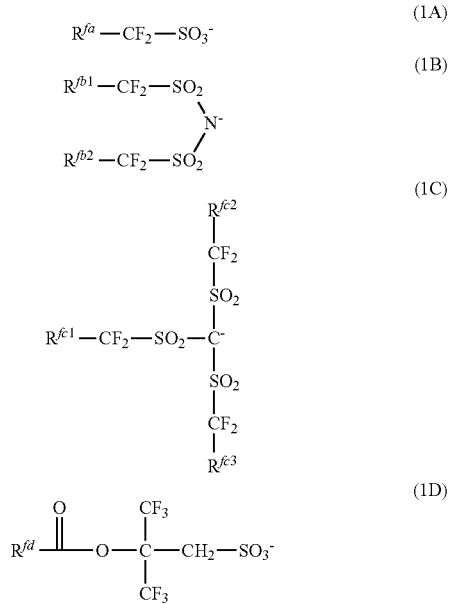

In formula (1A), $R^{fa}$ is fluorine or a $C_1$-$C_{40}$ straight, branched or cyclic monovalent hydrocarbon group which may contain a heteroatom.

Of the anions of formula (1A), an anion having the formula (1A') is preferred.

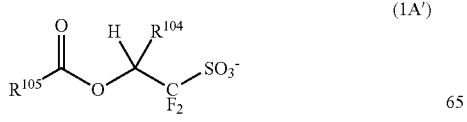

In formula (1A'), $R^{104}$ is hydrogen or trifluoromethyl, preferably trifluoromethyl. $R^{105}$ is a $C_1$-$C_{38}$ straight, branched or cyclic monovalent hydrocarbon group which may contain a heteroatom. As the heteroatom, oxygen, nitrogen, sulfur and halogen atoms are preferred, with oxygen being most preferred. Of the monovalent hydrocarbon groups represented by $R^{105}$, those groups of 6 to 30 carbon atoms are preferred from the aspect of achieving a high resolution in forming patterns of fine feature size. Suitable monovalent hydrocarbon groups include, but are not limited to, methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetamidomethyl, trifluoromethyl, (2-methoxyethoxy)methyl, acetoxymethyl, 2-carboxy-1-cyclohexyl, 2-oxopropyl, 4-oxo-1-adamantyl, and 3-oxocyclohexyl. In these groups, one or more hydrogen atoms may be substituted by a moiety containing a heteroatom such as oxygen, sulfur, nitrogen or halogen, or a moiety containing a heteroatom such as oxygen, sulfur or nitrogen may intervene between carbon atoms, so that the group may contain a hydroxyl, cyano, carbonyl, ether, ester, sulfonic acid ester, carbonate, lactone ring, sulfone ring, carboxylic anhydride or haloalkyl moiety.

With respect to the synthesis of the sulfonium salt having an anion of formula (1A'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the sulfonium salt having an anion of formula (1A) are shown below, but not limited thereto.

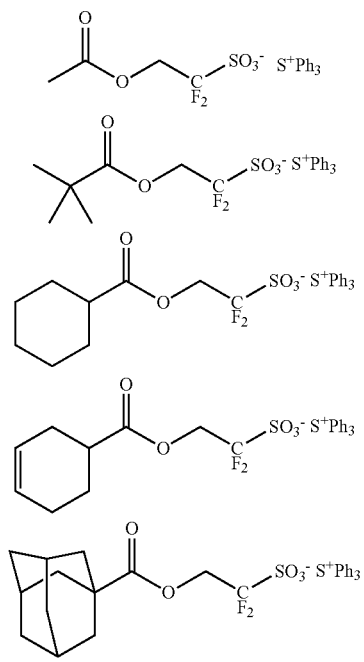

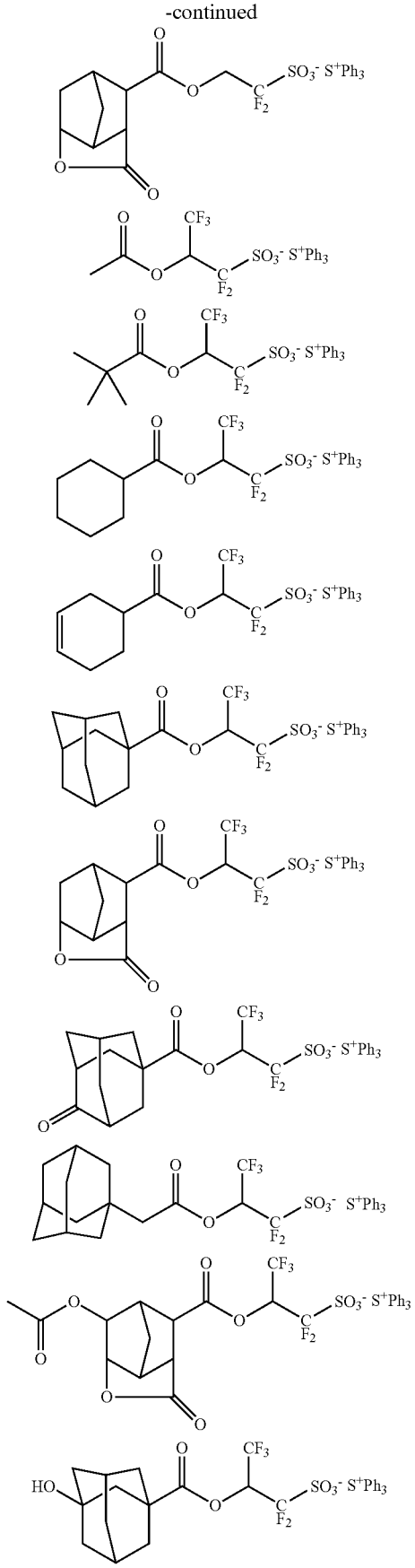
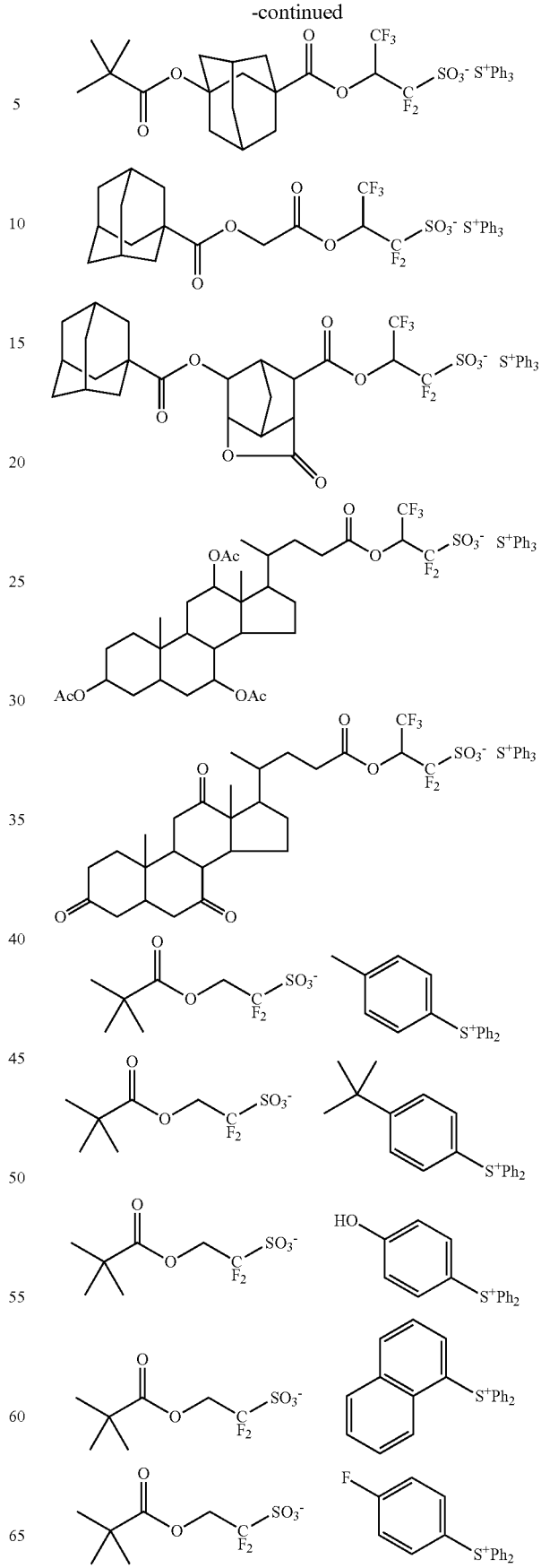

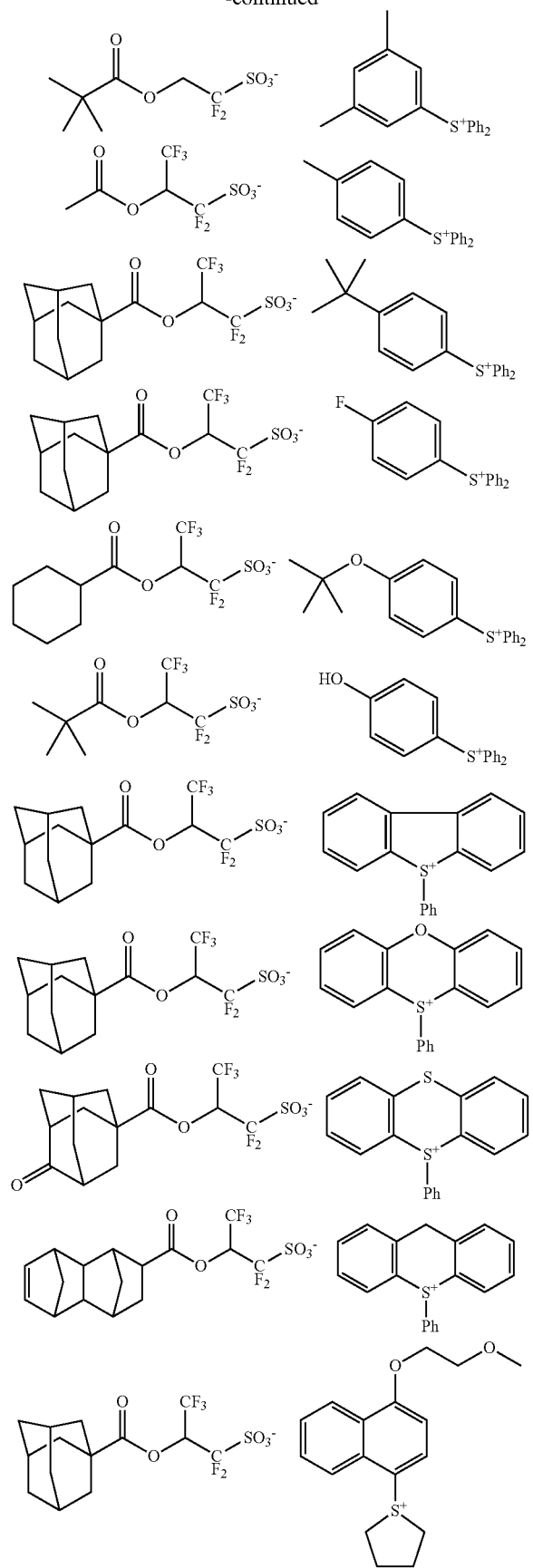
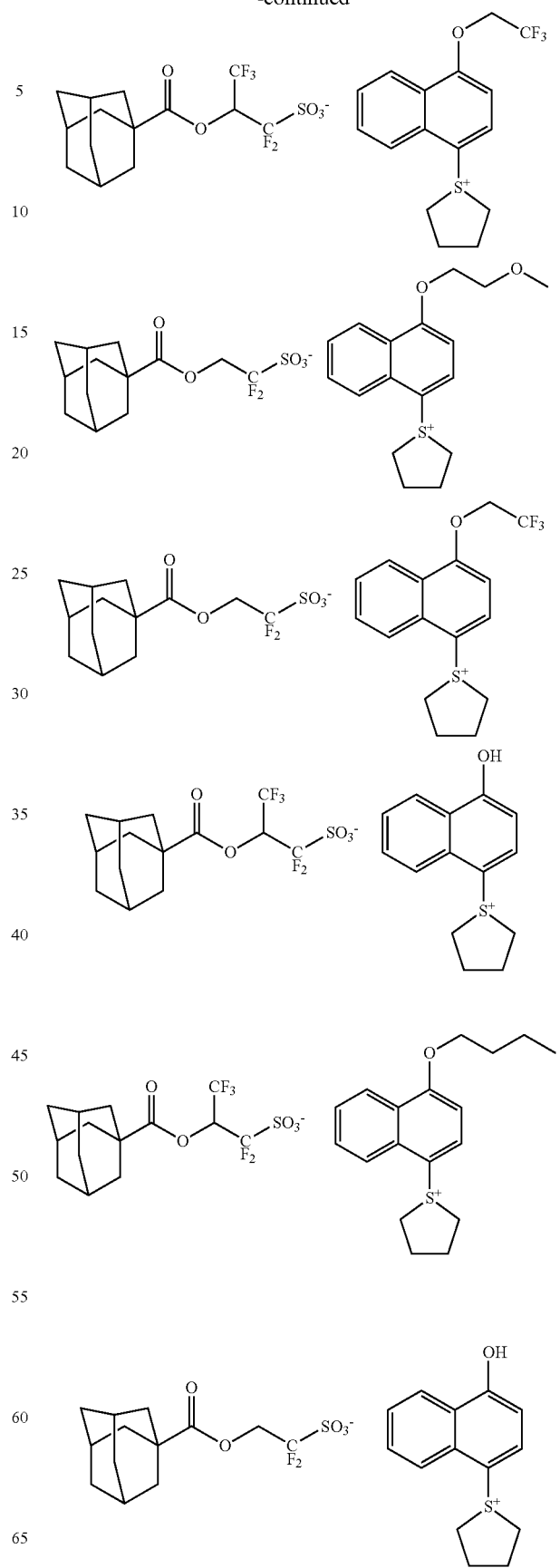

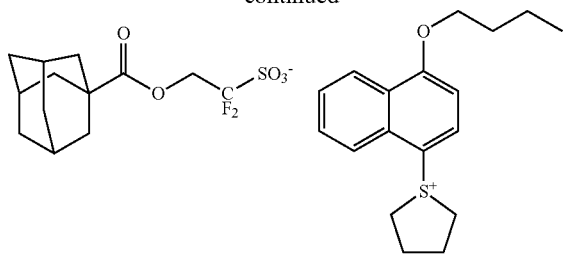

In formula (1B), $R^{fb1}$ and $R^{fb2}$ are each independently fluorine or a $C_1$-$C_{40}$ straight, branched or cyclic monovalent hydrocarbon group which may contain a heteroatom. Illustrative examples of the monovalent hydrocarbon group are as exemplified for $R^{105}$. Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: —$CF_2$—$SO_2$—$N^-$—$SO_2$—$CF_2$— to which they are attached. It is preferred to form a ring structure via a fluorinated ethylene or fluorinated propylene group.

In formula (1C), $R^{fc1}$, $R^{fc2}$ and $R^{fc3}$ are each independently fluorine or a $C_1$-$C_{40}$ straight, branched or cyclic monovalent hydrocarbon group which may contain a heteroatom. Illustrative examples of the monovalent hydrocarbon group are as exemplified for $R^{105}$. Preferably $R^{fc1}$, $R^{fc2}$ and $R^{fc3}$ are fluorine or $C_1$-$C_4$ straight fluorinated alkyl groups. Also, $R^{fc1}$ and $R^{fc2}$ may bond together to form a ring with the linkage: —$CF_2$—$SO_2$—$C^-$—$SO_2$—$CF_2$— to which they are attached. It is preferred to form a ring structure via a fluorinated ethylene or fluorinated propylene group.

In formula (1D), $R^{fd}$ is a $C_1$-$C_{40}$ straight, branched or cyclic monovalent hydrocarbon group which may contain a heteroatom. Illustrative examples of the monovalent hydrocarbon group are as exemplified for $R^{105}$.

With respect to the synthesis of the sulfonium salt having an anion of formula (1D), reference may be made to JP-A 2010-215608 and JP-A 2014-133723.

Examples of the sulfonium salt having an anion of formula (1D) are shown below, but not limited thereto.

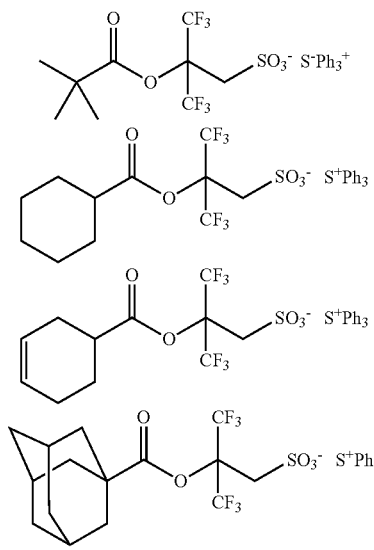
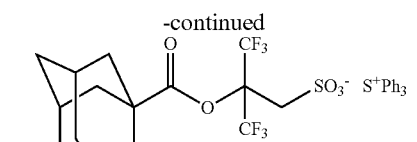
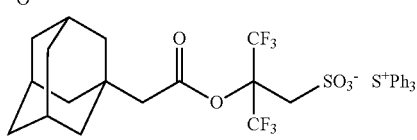
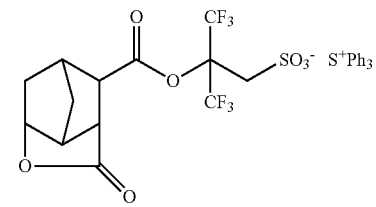
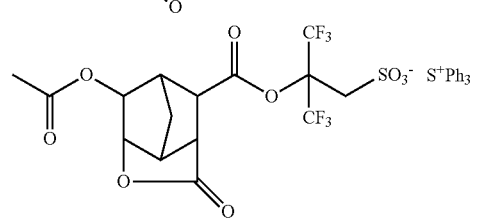
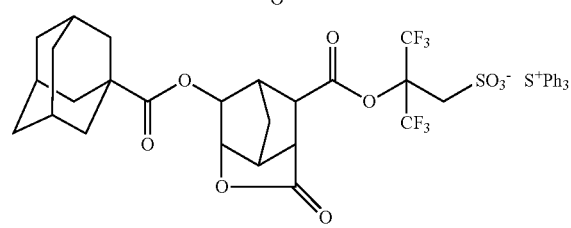
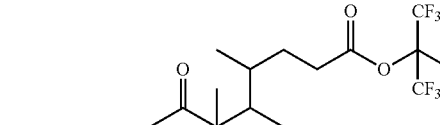
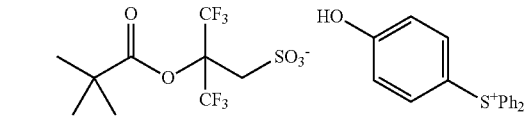
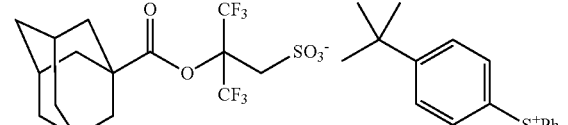
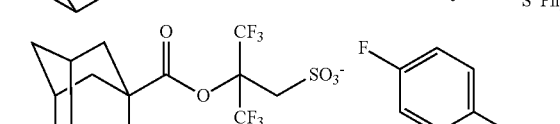
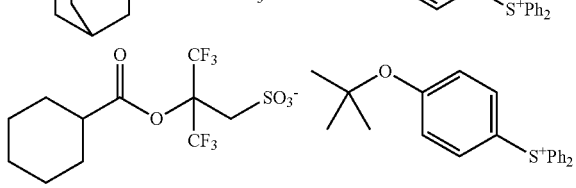

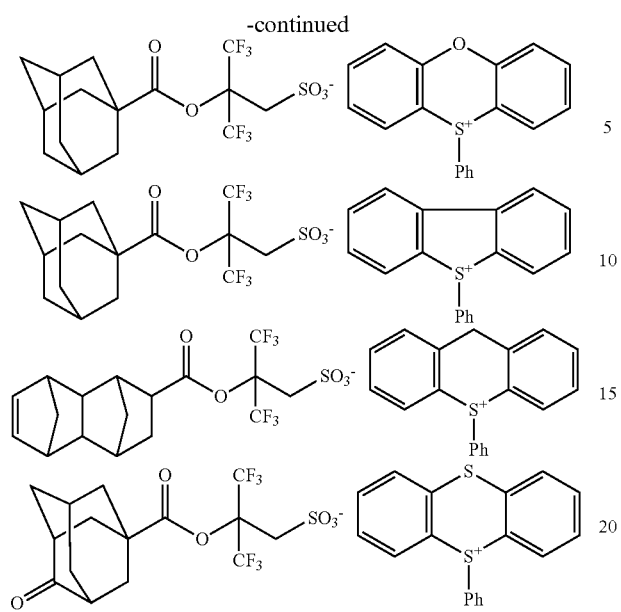

Notably, the compound having the anion of formula (1D) does not have fluorine at the α-position relative to the sulfo group, but two trifluoromethyl groups at the β-position. For this reason, it has a sufficient acidity to sever the acid labile groups in the resist polymer. Thus the compound is an effective PAG.

In formula (2), $R^{201}$ and $R^{202}$ are each independently a $C_1$-$C_{30}$ straight, branched or cyclic monovalent hydrocarbon group which may contain a heteroatom. $R^{203}$ is a $C_1$-$C_{30}$ straight, branched or cyclic divalent hydrocarbon group which may contain a heteroatom. Any two of $R^{201}$, $R^{202}$ and $R^{203}$ may bond together to form a ring with the sulfur atom to which they are attached. $L^A$ is a single bond, ether group or a $C_1$-$C_{20}$ straight, branched or cyclic divalent hydrocarbon group which may contain a heteroatom. $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl, and k is an integer of 0 to 3.

Examples of the monovalent hydrocarbon group include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl and anthracenyl. In these groups, one or more hydrogen atoms may be substituted by a moiety containing a heteroatom such as oxygen, sulfur, nitrogen or halogen, or one or more carbon atoms may be substituted by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sulfone ring, carboxylic anhydride or haloalkyl moiety.

Suitable divalent hydrocarbon groups include straight alkane-diyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; saturated cyclic divalent hydrocarbon groups such as cyclopentanediyl, cyclohexanediyl, norbornanediyl and adamantanediyl; and unsaturated cyclic divalent hydrocarbon groups such as phenylene and naphthylene. In these groups, one or more hydrogen atom may be replaced by an alkyl moiety such as methyl, ethyl, propyl, n-butyl or t-butyl; one or more hydrogen atom may be replaced by a moiety containing a heteroatom such as oxygen, sulfur, nitrogen or halogen; or a moiety containing a heteroatom such as oxygen, sulfur or nitrogen may intervene between carbon atoms, so that the group may contain a hydroxyl, cyano, carbonyl, ether, ester, sulfonic acid ester, carbonate, lactone ring, sulfone ring, carboxylic anhydride or haloalkyl moiety. Of the heteroatoms, oxygen is preferred.

Of the PAGs having formula (2), those having formula (2') are preferred.

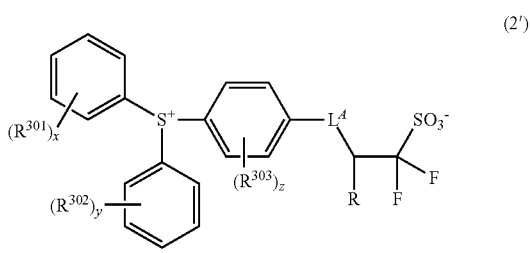

(2')

In formula (2'), $L^A$ is as defined above. R is hydrogen or trifluoromethyl, preferably trifluoromethyl. $R^{301}$, $R^{302}$ and $R^{303}$ are each independently hydrogen or a $C_1$-$C_{20}$ straight, branched or cyclic monovalent hydrocarbon group which may contain a heteroatom. Suitable monovalent, hydrocarbon groups are as described above for $R^{105}$. The subscripts x and y are each independently an integer of 0 to 5, and z is an integer of 0 to 4.

Examples of the PAG having formula (2) are shown below, but not limited thereto. Notably, R is as defined above.

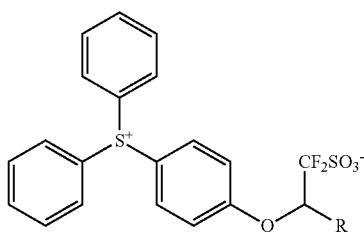

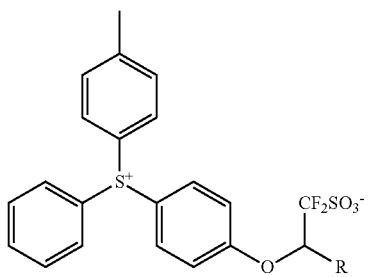

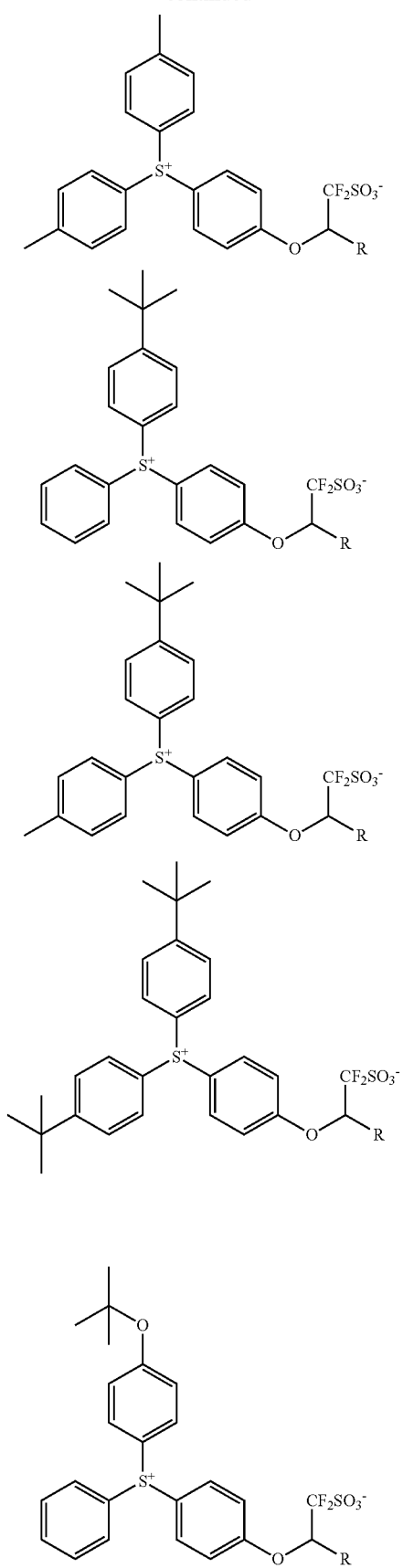
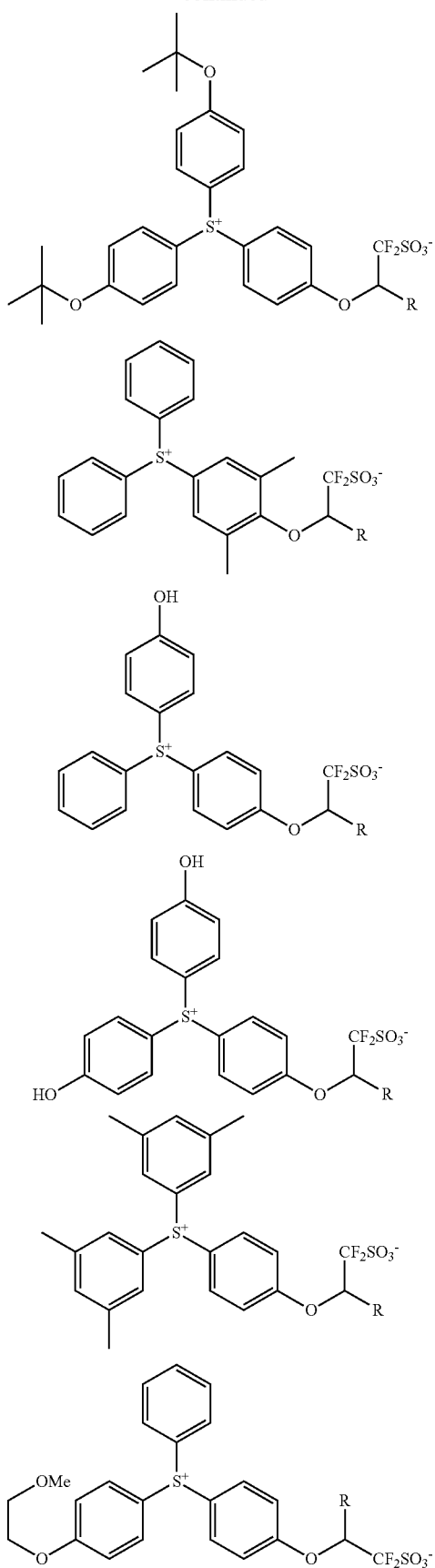

99
-continued
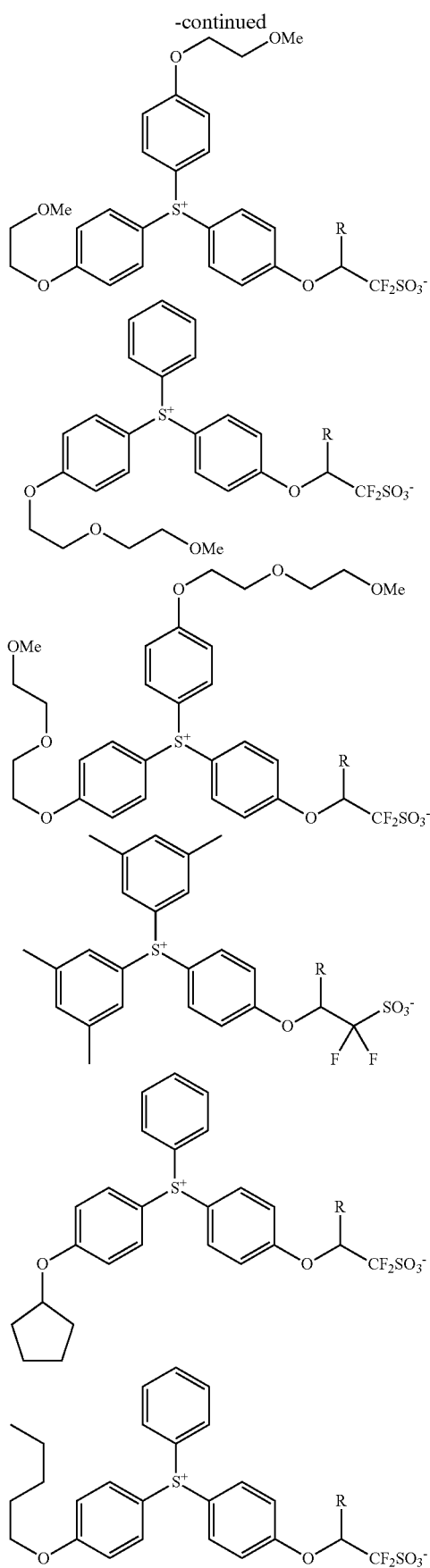
100
-continued
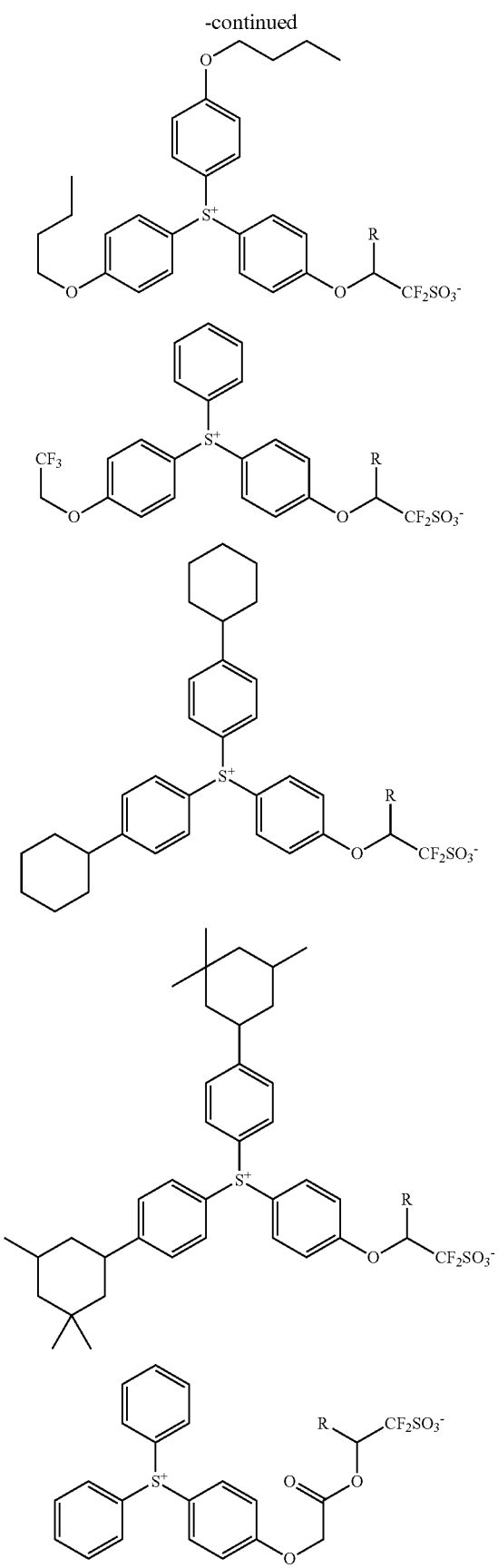

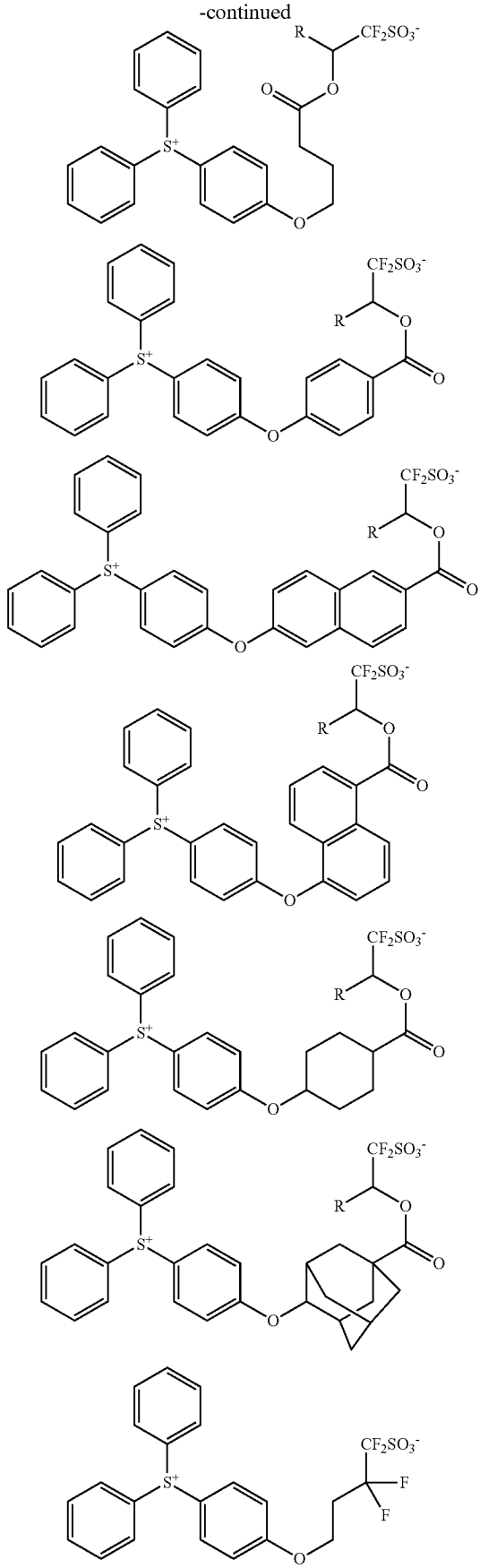
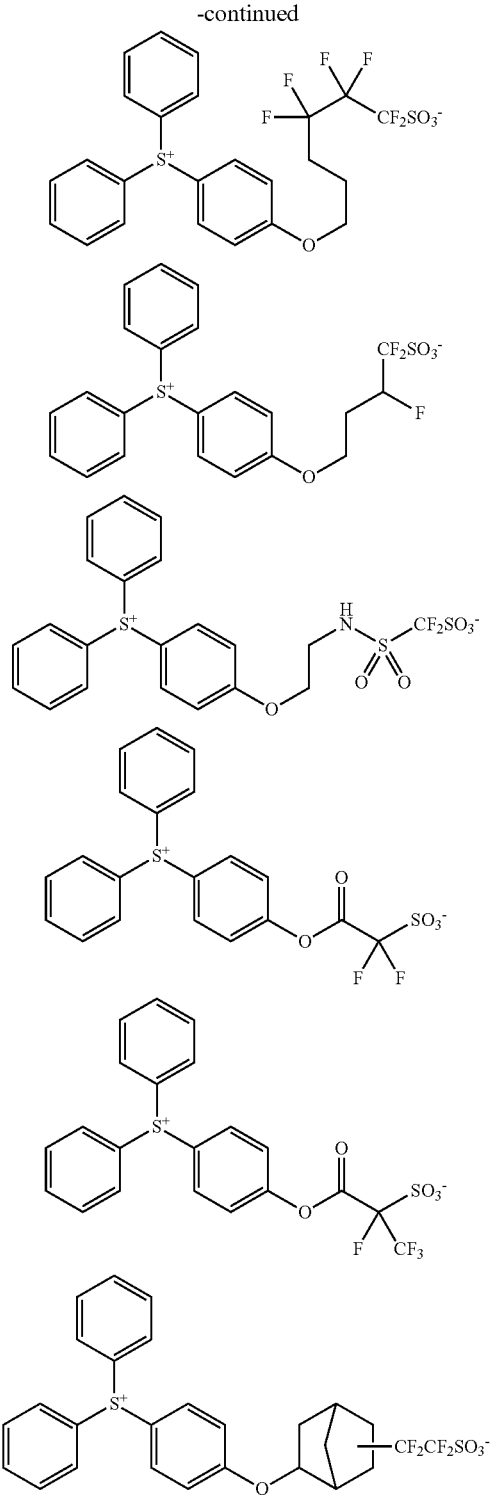

Of the foregoing PAGs, those having an anion of formula (1A') or (1D) are especially preferred because of reduced acid diffusion and high solubility in the resist solvent. Also those having an anion of formula (2') are especially preferred because of extremely reduced acid diffusion.

The PAG is preferably added in an amount of 0.1 to 50 parts, and more preferably 1 to 40 parts by weight per 100 parts by weight of the base polymer.

Other Components

With the phosphazene salt compound having formula (A), the base polymer, and the acid generator, all defined above, other components such as an organic solvent, surfactant, dissolution inhibitor, and crosslinker may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs. Particularly when an acid generator is incorporated to formulate a chemically amplified positive resist composition capable of utilizing acid catalyzed reaction, the composition has a higher sensitivity and is further improved in the properties described above.

In the case of positive resist compositions, inclusion of a dissolution inhibitor may lead to an increased difference in dissolution rate between exposed and unexposed regions and a further improvement in resolution. In the case of negative resist compositions, a negative pattern may be formed by adding a crosslinker to reduce the dissolution rate of the exposed region.

Examples of the organic solvent used herein are described in JP-A 2008-111103, paragraphs [0144]-[0145] (U.S. Pat. No. 7,537,880). Exemplary solvents include ketones such as cyclohexanone, cyclopentanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Exemplary surfactants are described in JP-A 2008-111103, paragraphs [0165]-[0166]. Inclusion of a surfactant may improve or control the coating characteristics of the resist composition. The surfactant is preferably added in an amount of 0.0001 to 10 parts by weight per 100 parts by weight of the base polymer.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer.

Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyl ether group. These compounds may be used as an additive or introduced into a polymer side chain as a pendant. Hydroxy-containing compounds may also be used as the crosslinker.

Of the foregoing crosslinkers, examples of suitable epoxy compounds include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

In the resist composition of the invention, a quencher other than the phosphazene salt compound having formula (A) may be blended. The other quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl, ether, ester, lactone ring, cyano, or sulfonic acid ester group as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in US 2008153030 (JP-A 2008-158339) and similar onium salts of carboxylic acid may also be used as the other quencher. While an α-fluorinated sulfonic acid, sulfonimide, and sulfonmethide are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer.

To the resist composition, a polymeric additive (or water repellency improver) may also be added for improving the water repellency on surface of a resist film as spin coated. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. An appropriate amount of the water repellency improver is 0 to 20 parts, preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Process

The resist composition is used in the fabrication of various integrated circuits. Pattern formation using the resist composition may be performed by well-known lithography processes. The process generally involves coating, prebaking, exposure, post-exposure baking (PEB), and development. If necessary, any additional steps may be added.

For example, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, or $MoSi_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably 80 to 120° C. for 30 seconds to 20 minutes. The resulting resist film is generally 0.1 to 2.0 μm thick.

The resist film is then exposed to a desired pattern of high-energy radiation such as UV, deep-UV, EB, EUV, x-ray, soft x-ray, excimer laser light, γ-ray or synchrotron radiation, directly or through a mask. The exposure dose is preferably about 1 to 200 $mJ/cm^2$, more preferably about 10 to 100 $mJ/cm^2$, or about 0.1 to 100 $\mu C/cm^2$, more preferably about 0.5 to 50 $\mu C/cm^2$. The resist film is further baked (PEB) on a hot plate at 60 to 150° C. for 10 seconds to 30 minutes, preferably 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed region is dissolved in the developer whereas the resist film in the unexposed region is not dissolved. In this way, the desired positive pattern is formed on the substrate. Inversely in the case of negative resist, the exposed region of resist film is insolubilized and the unexposed region is dissolved in the developer. It is appreciated that the resist composition of the invention is best suited for micro-patterning using such high-energy radiation as KrF and ArF excimer laser, EB, EUV, x-ray, soft x-ray, γ-ray and synchrotron radiation.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. The solvents may be used alone or in admixture. Besides the foregoing solvents, aromatic solvents may be used, for example, toluene, xylene, ethylbenzene, isopropylbenzene, t-butylbenzene and mesitylene.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLE

Examples of the invention are given below by way of illustration and not by way of limitation. The abbreviation "pbw" is parts by weight. For all polymers, Mw and Mn are determined by GPC versus polystyrene standards using tetrahydrofuran solvent, and dispersity Mw/Mn is computed therefrom.

Quenchers 1 to 13 in the form of phosphazene salt compounds used herein have the following structure. Quenchers 1 to 13 were synthesized by mixing a phosphazene compound to provide the illustrated cation with a carboxylic acid, sulfonimide, nitric acid, hydrochloric acid or hydroiodic acid to provide the illustrated anion.

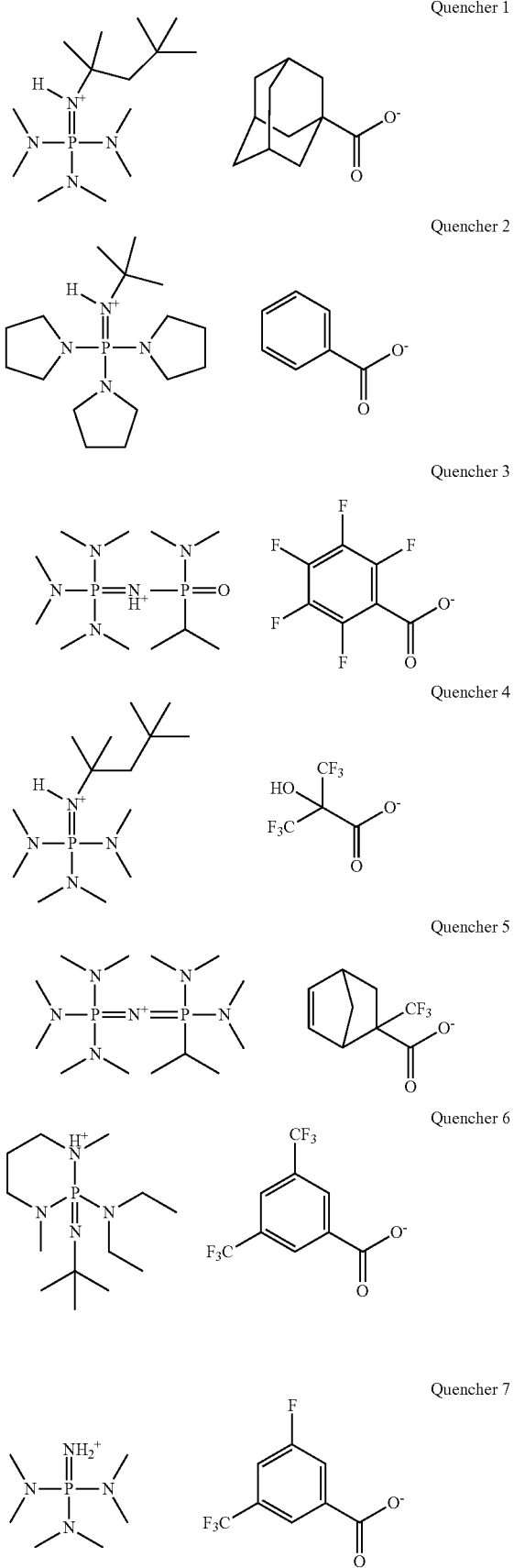

Quencher 8

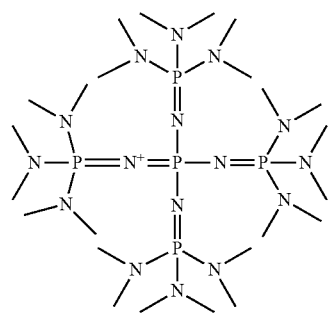

Quencher 9

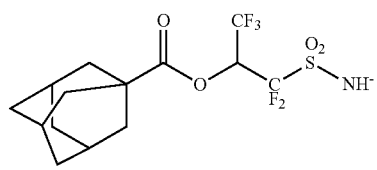

Quencher 10

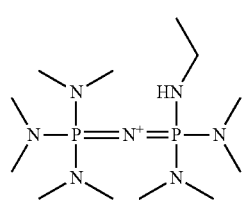

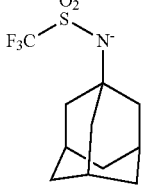

Quencher 11

Quencher 12

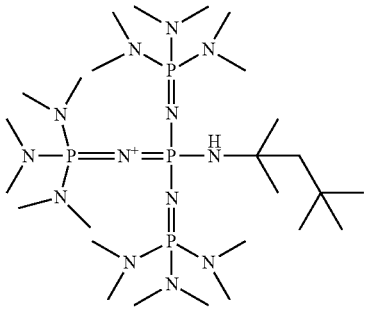

Cl⁻

Quencher 13

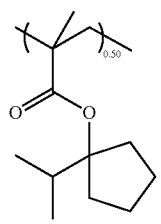

I⁻

Synthesis Example

Synthesis of Polymers 1 to 6

Base, polymers were prepared by combining suitable monomers, effecting copolymerization reaction, thereof in tetrahydrofuran solvent, pouring the reaction solution into methanol for crystallization, repeatedly washing with hexane, isolation, and drying. The resulting polymers, designated Polymers 1 to 6, were analyzed for composition by $^1$H-NMR, and for Mw and Mw/Mn by GPC.

Polymer 1
Mw = 8,500
Mw/Mn = 1.78

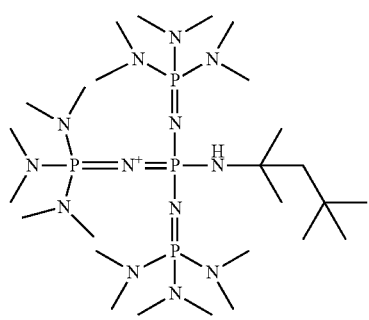

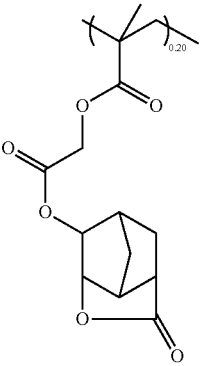

NO₃⁻

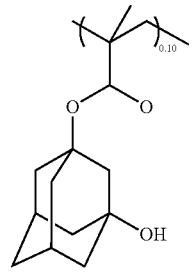

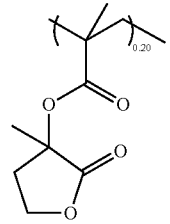

-continued
Polymer 2
Mw = 8,700
Mw/Mn = 1.89
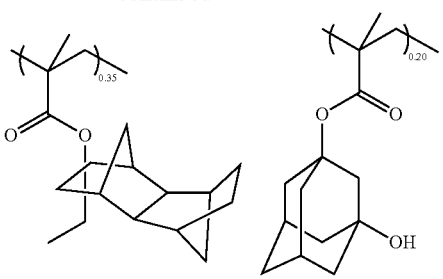
Polymer 4
Mw = 7,600
Mw/Mn = 1.73
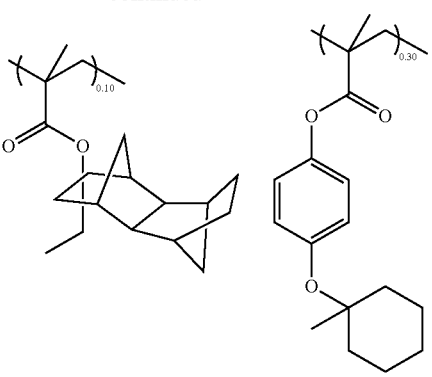
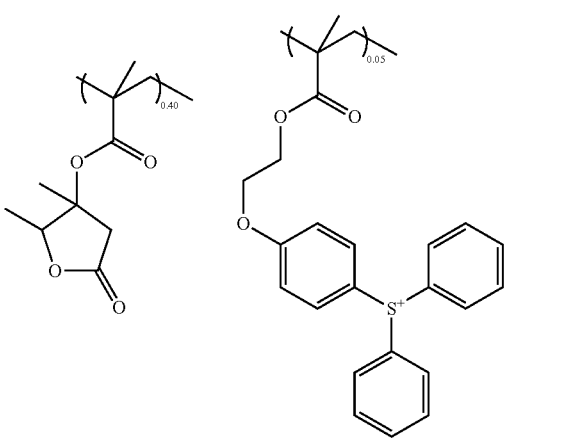
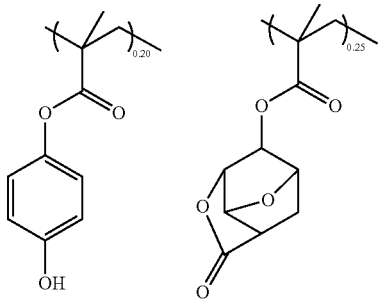
Polymer 3
Mw = 8,600
Mw/Mn = 1.61
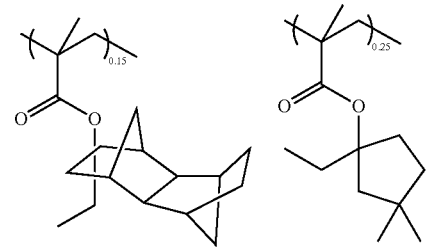
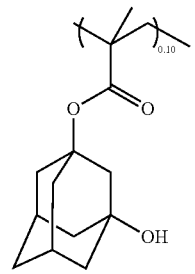
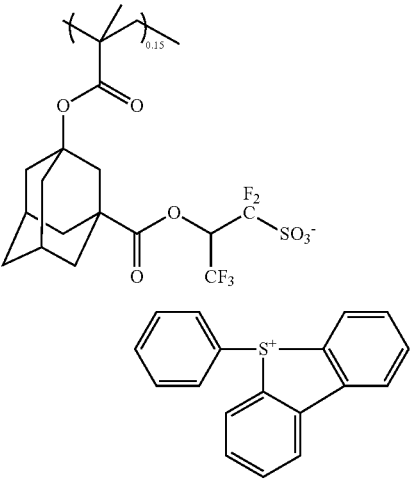

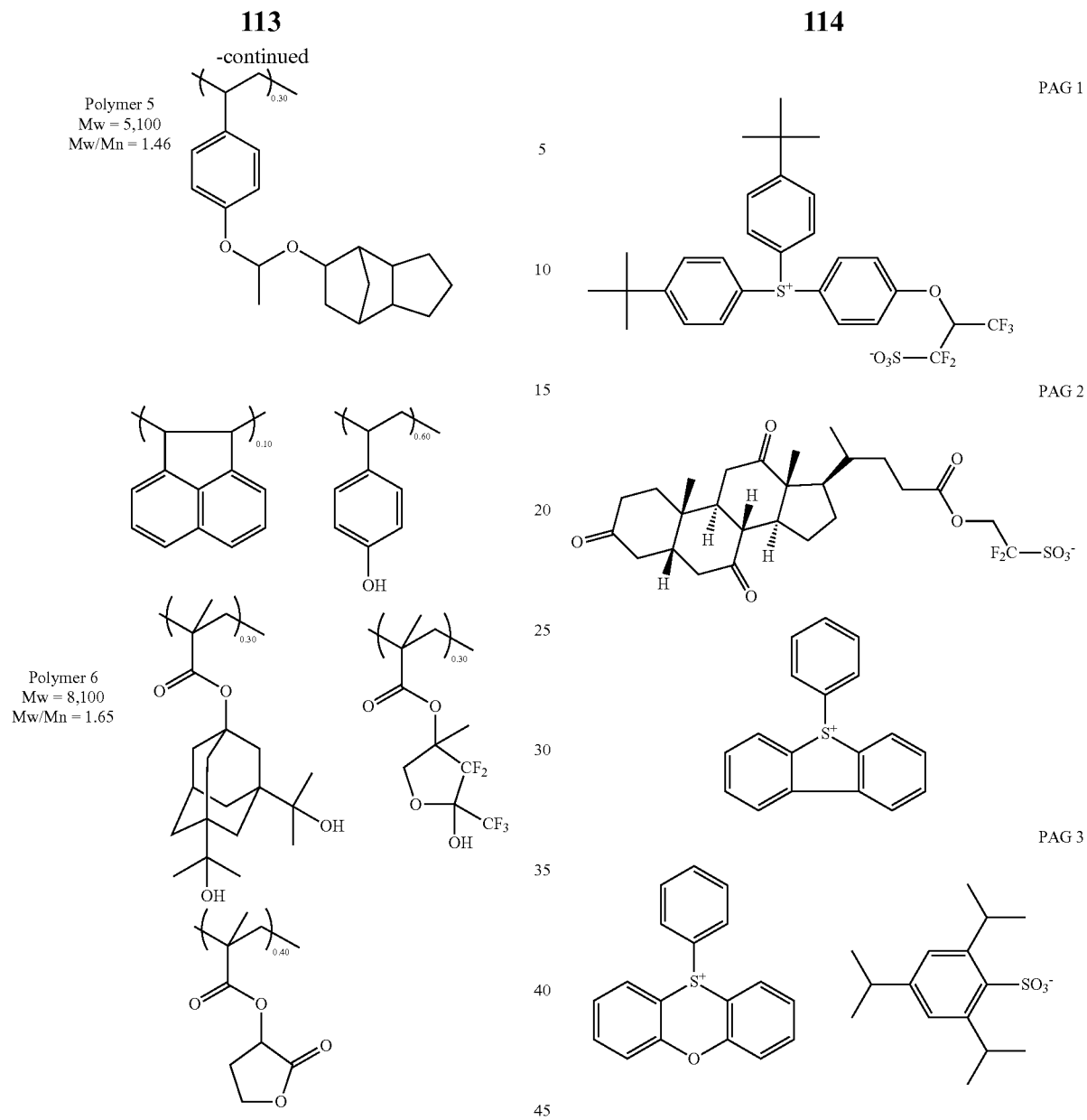

Quenchers: Quenchers 1 to 13 as Identified Above, Comparative Quenchers 1 to 5

Examples and Comparative Examples

Positive or negative resist compositions were prepared by dissolving each of the polymers synthesized above and selected components in a solvent in accordance with the recipe shown in Tables 1 and 2, and filtering through a filter having a pore size of 0.2 µm. The solvent contained 100 ppm of a surfactant FC-4430 (3M-Sumitomo Co., Ltd.). The components in Tables 1 and 2 are as identified below.

Polymers: Polymers 1 to 6 as Identified Above

Organic Solvents:
- propylene glycol monomethyl ether acetate (PGMEA)
- propylene glycol monomethyl ether (PGME)
- γ-butyrolactone (GBL)
- cyclohexanone (CyH)
- cyclopentanone (CyP)

Acid Generators: PAG1 to PAG3

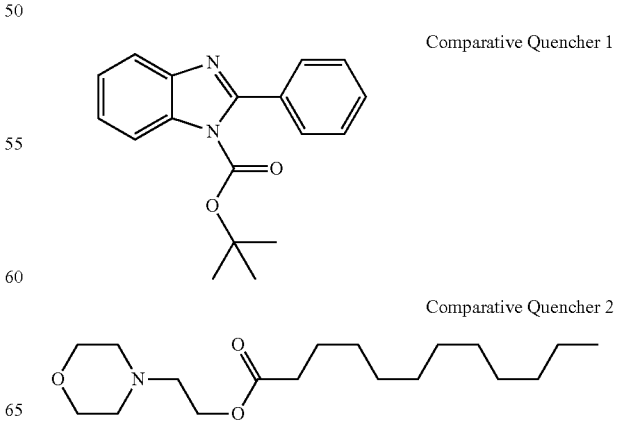

Comparative Quencher 3

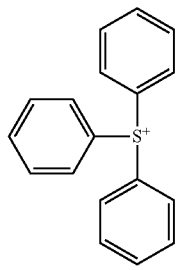

Comparative Quencher 4

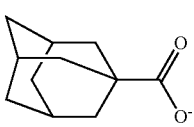

Comparative Quencher 5

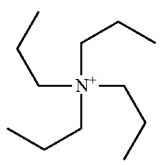

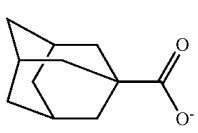

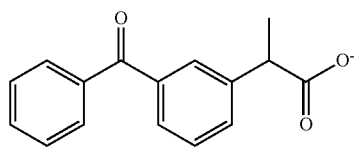

Water-Repellent Polymer:

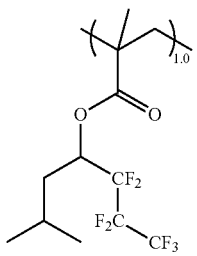

Water-repellent polymer 1
Mw = 8,900
Mw/Mn = 1.96

ArF Immersion Lithography Patterning Test

Examples 1-1 to 1-14 and Comparative Examples 1-1 to 1-5

On a substrate (silicon wafer), a spin-on carbon film ODL-102 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, each of the resist compositions in Table 1 was spin coated, then baked on a hot plate at 100° C. for 60 seconds to form a resist film of 80 nm thick.

Using an ArF excimer laser immersion lithography scanner NSR-S610C (Nikon Corp., NA 1.30, σ 0.98/0.78, 35° cross-pole illumination, azimuthally polarized illumination), the resist film was exposed through a 6% halftone phase shift mask bearing a pattern having a line of 60 nm and a pitch of 200 nm (on-wafer size). The resist film was baked (PEB) at the temperature shown in Table 1 for 60 seconds and immediately developed in n-butyl acetate for 30 seconds, yielding a negative trench pattern having a space of 60 nm and a pitch of 200 nm.

In another run, the same procedure as above was followed until the exposure and PEB steps. The resist film was stored in a FOUP at 23° C. for 24 hours before it was developed in n-butyl acetate for 30 seconds, yielding a negative trench pattern at a pitch of 200 nm.

Trench pattern size was measured under a scanning electron microscope (SEM) CG-4000 (Hitachi High-Technologies Corp.). The difference between the size of the trench pattern printed by the continuous procedure from coating to development and the size of the trench pattern printed through 24-hour storage (or delay) after PEB is reported as PPD size.

The results are shown in Table 1.

TABLE 1

|  |  | Polymer (pbw) | Acid generator (pbw) | Quencher (pbw) | Water-repellent polymer (pbw) | Organic solvent (pbw) | PEB temp. (° C.) | Sensitivity (mJ/cm$^2$) | PPD size (nm) |
|---|---|---|---|---|---|---|---|---|---|
| Example | 1-1 | Polymer 1 (100) | PAG1 (8.0) | Quencher 1 (2.50) | Water-repellent polymer 1 (4.0) | PGMEA(2,200) GBL(300) | 95 | 39 | 0.1 |
|  | 1-2 | Polymer 1 (100) | PAG1 (8.0) | Quencher 2 (2.50) | Water-repellent polymer 1 (4.0) | PGMEA(2,200) GBL(300) | 95 | 42 | 0 |

TABLE 1-continued

| | | Polymer (pbw) | Acid generator (pbw) | Quencher (pbw) | Water-repellent polymer (pbw) | Organic solvent (pbw) | PEB temp. (° C.) | Sensitivity (mJ/cm$^2$) | PPD size (nm) |
|---|---|---|---|---|---|---|---|---|---|
| | 1-3 | Polymer 1 (100) | PAG1 (8.0) | Quencher 3 (2.50) | Water-repellent polymer 1 (4.0) | PGMEA(2,200) GBL(300) | 95 | 38 | 0.1 |
| | 1-4 | Polymer 1 (100) | PAG1 (8.0) | Quencher 4 (2.20) | Water-repellent polymer 1 (4.0) | PGMEA(2,200) GBL(300) | 95 | 36 | 0 |
| | 1-5 | Polymer 1 (100) | PAG1 (8.0) | Quencher 5 (2.10) | Water-repellent polymer 1 (4.0) | PGMEA(2,200) GBL(300) | 95 | 37 | 0.1 |
| | 1-6 | Polymer 1 (100) | PAG1 (8.0) | Quencher 6 (2.50) | Water-repellent polymer 1 (4.0) | PGMEA(2,200) GBL(300) | 95 | 38 | 0.2 |
| | 1-7 | Polymer 1 (100) | PAG1 (8.0) | Quencher 7 (2.50) | Water-repellent polymer 1 (4.0) | PGMEA(2,200) GBL(300) | 95 | 41 | 0.1 |
| | 1-8 | Polymer 1 (100) | PAG1 (8.0) | Quencher 8 (3.10) | Water-repellent polymer 1 (4.0) | PGMEA(2,200) GBL(300) | 95 | 39 | 0 |
| | 1-9 | Polymer 1 (100) | PAG1 (8.0) | Quencher 9 (3.50) | Water-repellent polymer 1 (4.0) | PGMEA(2,200) GBL(300) | 95 | 40 | 0 |
| | 1-10 | Polymer 3 (100) | PAG1 (8.0) | Quencher 10 (2.90) | Water-repellent polymer 1 (4.0) | PGMEA(2,200) GBL(300) | 95 | 41 | 0 |
| | 1-11 | Polymer 2 (100) | — | Quencher 10 (2.50) | Water-repellent polymer 1 (4.0) | PGMEA(2,200) GBL(300) | 100 | 44 | 0 |
| | 1-12 | Polymer 2 (100) | — | Quencher 11 (2.10) | Water-repellent polymer 1 (4.0) | PGMEA(2,200) GBL(300) | 100 | 44 | 0 |
| | 1-13 | Polymer 2 (100) | — | Quencher 12 (2.10) | Water-repellent polymer 1 (4.0) | PGMEA(2,200) GBL(300) | 100 | 46 | 0 |
| | 1-14 | Polymer 2 (100) | — | Quencher 13 (2.10) | Water-repellent polymer 1 (4.0) | PGMEA(2,200) GBL(300) | 100 | 48 | 0 |
| Comparative Example | 1-1 | Polymer 1 (100) | PAG1 (8.0) | Comparative Quencher 1 (3.13) | Water-repellent polymer 1 (4.0) | PGMEA(2,200) GBL(300) | 95 | 55 | 1.3 |
| | 1-2 | Polymer 1 (100) | PAG1 (8.0) | Comparative Quencher 2 (3.13) | Water-repellent polymer 1 (4.0) | PGMEA(2,200) GBL(300) | 95 | 56 | 1.5 |
| | 1-3 | Polymer 1 (100) | PAG1 (8.0) | Comparative Quencher 3 (4.50) | Water-repellent polymer 1 (4.0) | PGMEA(2,200) GBL(300) | 95 | 45 | 0.8 |
| | 1-4 | Polymer 1 (100) | PAG1 (8.0) | Comparative Quencher 4 (4.50) | Water-repellent polymer 1 (4.0) | PGMEA(2,200) GBL(300) | 95 | 44 | 0.6 |
| | 1-5 | Polymer 1 (100) | PAG1 (8.0) | Comparative Quencher 5 (4.50) | Water-repellent polymer 1 (4.0) | PGMEA(2,200) GBL(300) | 95 | 55 | 0.5 |

EB Writing Test

Examples 2-1 to 2-5 and Comparative Examples 2-1 to 2-5

Each of the resist compositions in Table 2 was spin coated onto a silicon substrate, which had been vapor primed with hexamethyldisilazane (HMDS), and pre-baked on a hot plate at 110° C. for 60 seconds to form a resist film of 80 nm thick. Using a system HL-800D (Hitachi Ltd.) at an accelerating voltage of 50 kV, the resist film was exposed imagewise to EB in a vacuum chamber. Immediately after the image writing, the resist film was baked (PEB) on a hot plate at 90° C. for 60 seconds and developed in a 2.38 wt % TMAH aqueous solution for 30 seconds to form a pattern. The resist pattern was evaluated as follows.

In the case of positive resist film, the resolution is a minimum trench size at the exposure dose that provides a resolution as designed of a 120-nm trench pattern. In the case of negative resist film, the resolution is a minimum isolated line size at the exposure dose that provides a resolution as designed of a 120-nm isolated line pattern. It is noted that Examples 2-1 to 2-4 and Comparative Examples 2-1 to 2-3, 2-5 are positive resist compositions, and Example 2-5 and Comparative Example 2-4 are negative resist compositions.

The results are shown in Table 2.

TABLE 2

|  |  | Polymer (pbw) | Acid generator (pbw) | Base (pbw) | Organic solvent (pbw) | Sensitivity (μC/cm²) | Resolution (nm) | LWR (nm) |
|---|---|---|---|---|---|---|---|---|
| Example | 2-1 | Polymer 4 (100) | — | Quencher 8 (1.80) | PGMEA(400) CyH(2,000) PGME(100) | 32 | 75 | 3.0 |
|  | 2-2 | Polymer 4 (100) | — | Quencher 9 (1.80) | PGMEA(400) CyH(2,000) PGME(100) | 33 | 75 | 3.1 |
|  | 2-3 | Polymer 4 (100) | — | Quencher 10 (1.90) | PGMEA(400) CyH(2,000) PGME(100) | 35 | 75 | 3.0 |
|  | 2-4 | Polymer 5 (100) | PAG2 (15.0) | Quencher 8 (1.80) | PGMEA(400) CyH(1,600) CyP(500) | 36 | 80 | 3.3 |
|  | 2-5 | Polymer 6 (100) | PAG3 (10.0) | Quencher 8 (1.80) | PGMEA(2,000) CyH(500) | 36 | 75 | 3.9 |
| Comparative Example | 2-1 | Polymer 4 (100) | — | Comparative Quencher 1 (2.50) | PGMEA(400) CyH(2,000) PGME(100) | 38 | 90 | 4.5 |
|  | 2-2 | Polymer 4 (100) | — | Comparative Quencher 2 (2.50) | PGMEA(400) CyH(2,000) PGME(100) | 38 | 90 | 4.6 |
|  | 2-3 | Polymer 4 (100) | — | Comparative Quencher 3 (2.50) | PGMEA(400) CyH(2,000) PGME(100) | 38 | 90 | 4.2 |
|  | 2-4 | Polymer 6 (100) | PAG1 (10.0) | Comparative Quencher 3 (2.50) | PGMEA(2,000) CyH(500) | 38 | 85 | 5.2 |
|  | 2-5 | Polymer 4 (100) | — | Comparative Quencher 5 (2.50) | PGMEA(400) CyH(2,000) PGME(100) | 44 | 90 | 4.3 |

It is demonstrated in Tables 1 and 2 that resist compositions comprising a phosphazene salt compound offer dimensional stability on PPD and a satisfactory resolution and LWR.

Japanese Patent Application Nos. 2015-256346 and 2016-135025 are incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer and a phosphazene salt compound having the formula (A):

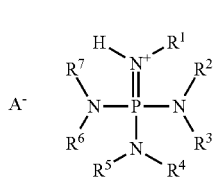

wherein $R^1$ to $R^7$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, which may contain an ester, ether, sulfide, sulfoxide, carbonate, carbamate, sulfone, halogen, amino, amide, hydroxy, thiol or nitro moiety, a pair of $R^1$ and $R^2$, $R^2$ and $R^3$, $R^3$ and $R^4$, $R^4$ and $R^5$, $R^5$ and $R^6$, or $R^6$ and $R^7$ may bond together to form a ring, or a pair of $R^2$ and $R^3$, $R^4$ and $R^5$, or $R^6$ and $R^7$, taken together, may form a double bond or a group having the formula (A)-1, $R^1$ may be a group having the formula (A)-2,

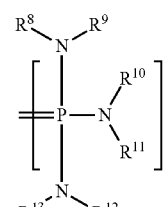

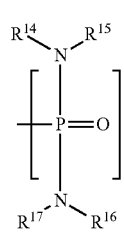

wherein $R^8$ to $R^{17}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, a pair of $R^8$ and $R^9$, $R^9$ and $R^{10}$, $R^{10}$ and $R^{11}$, $R^{11}$ and $R^{12}$, $R^{12}$ and $R^{13}$, $R^{14}$ and $R^{15}$, or $R^{16}$ and $R^{17}$ may bond together to form a ring, or a pair of $R^8$ and $R^9$, $R^{10}$ and $R^{11}$, or $R^{12}$ and $R^{13}$, taken together, may form a double bond or a group having the formula (A)-1, A⁻ is an anion selected from the group consisting of hydroxide, chloride, bromide, iodide, nitrate, nitrite, chlorate, chlorite, perchlorate, hydrogencarbonate, dihydrogenphosphate, hydrogensulfate, thiocyanate, hydrogenoxalate, cyanide, iodate ions, and anions of the formulae (M-1) and (M-2):

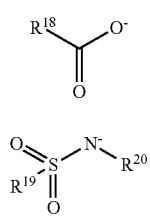 (M)-1

 (M)-2 wherein $R^{18}$ is hydrogen, or a $C_1$-$C_{30}$ straight, branched or cyclic alkyl group, $C_2$-$C_{30}$ straight, branched or cyclic alkenyl group, $C_2$-$C_{30}$ straight, branched or cyclic alkynyl group, $C_6$-$C_{20}$ aryl group, $C_7$-$C_{20}$ aralkyl group, or $C_3$-$C_{20}$ aromatic or aliphatic heterocycle-containing group, which may contain an ester, ether, sulfide, sulfoxide, carbonate, carbamate, sulfone, halogen, amino, amide, hydroxy, thiol or nitro moiety, with the proviso that $R^{18}$ does not contain a group of the formula (A)-3:

(A)-3 wherein Ar is a $C_6$-$C_{16}$ aromatic group, $R^{21}$ and $R^{22}$ are each independently hydrogen, hydroxy, alkoxy, $C_1$-$C_6$ straight, branched or cyclic alkyl group, or $C_6$-$C_{10}$ aryl group, $R^{19}$ is fluorine, or a $C_1$-$C_{10}$ straight, branched or cyclic fluoroalkyl group or fluorophenyl group, which may contain a hydroxy, ether, ester or alkoxy moiety, $R^{20}$ is hydrogen, or a $C_1$-$C_{10}$ straight, branched or cyclic alkyl group, $C_2$-$C_{10}$ straight, branched or cyclic alkenyl group, $C_2$-$C_{10}$ straight or branched alkynyl group, or $C_6$-$C_{10}$ aryl group, which may contain a hydroxy, ether, ester or alkoxy moiety, wherein the carboxylate anion having formula (M-1) is selected from the group consisting of the following formulae:

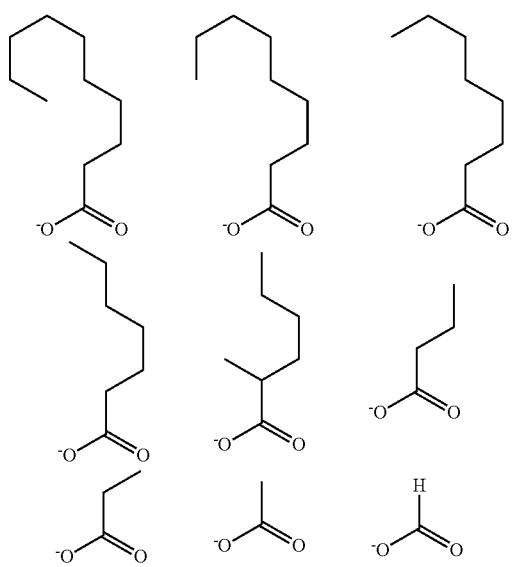

-continued

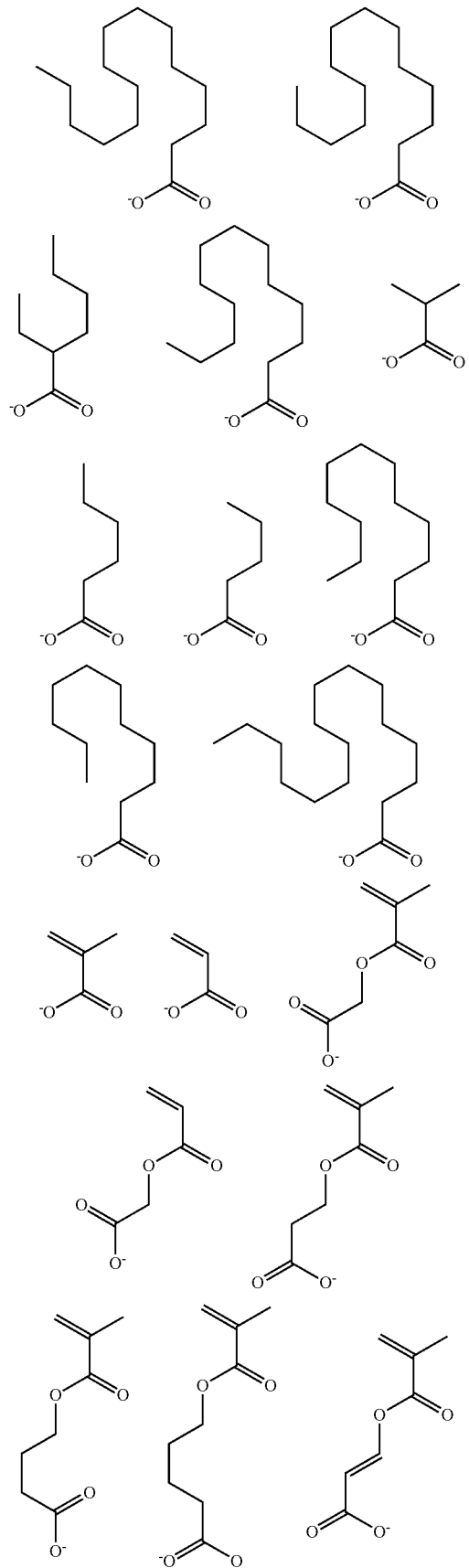

123
-continued
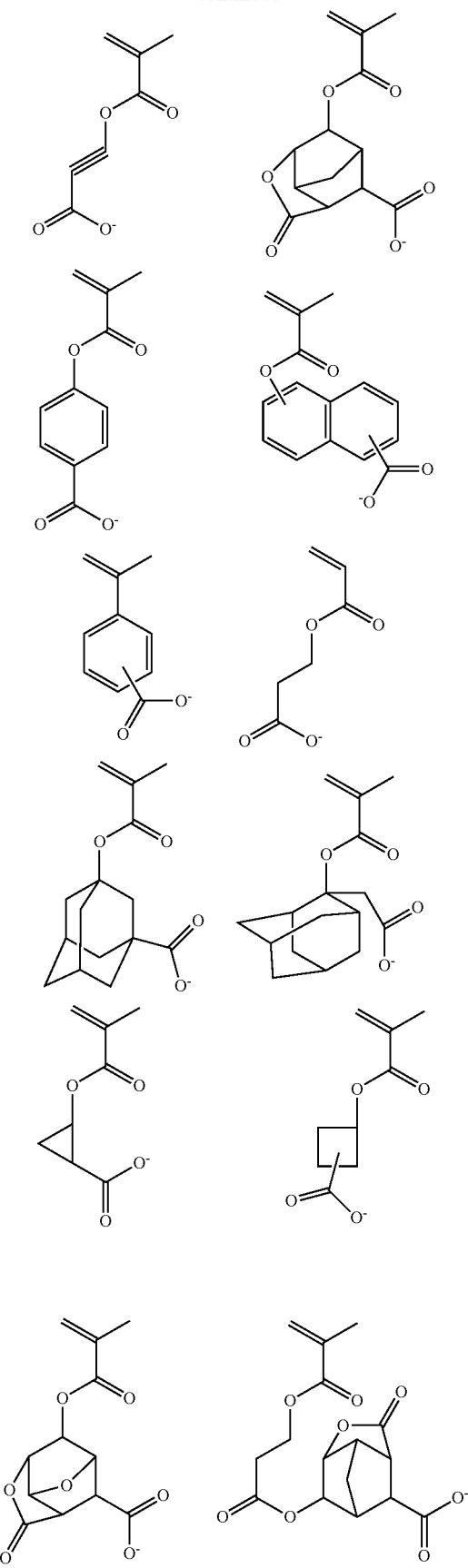
124
-continued
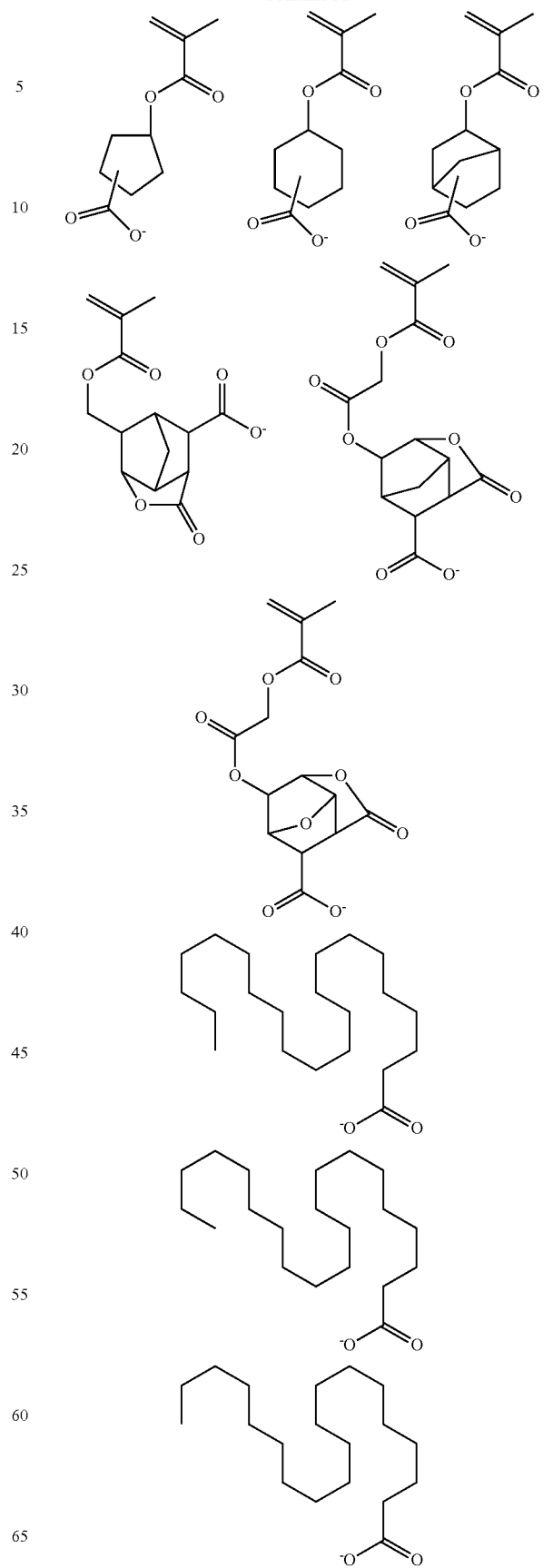

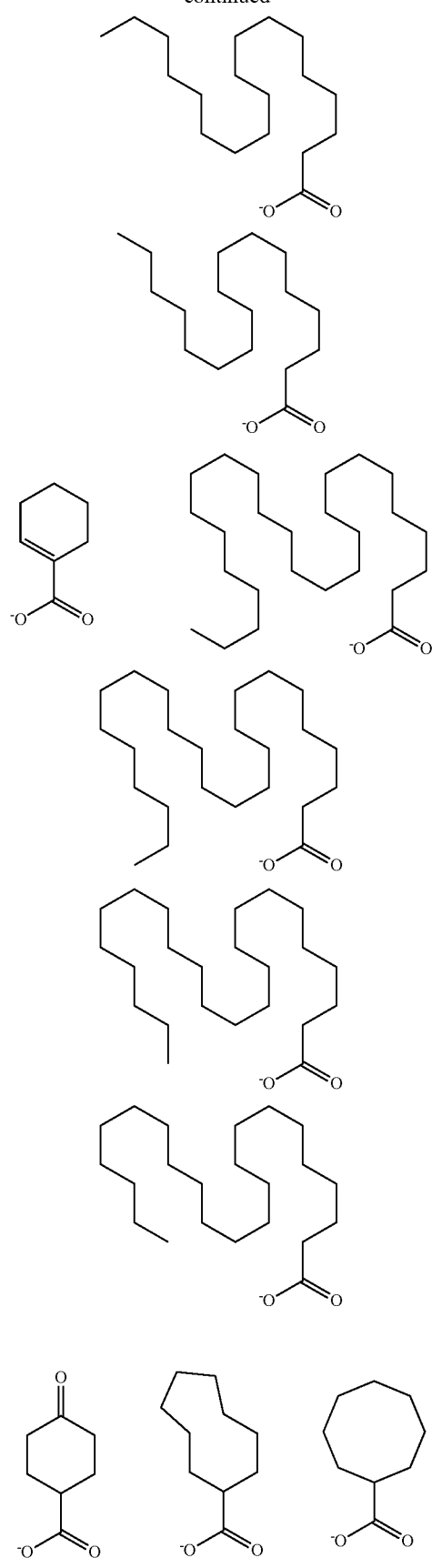
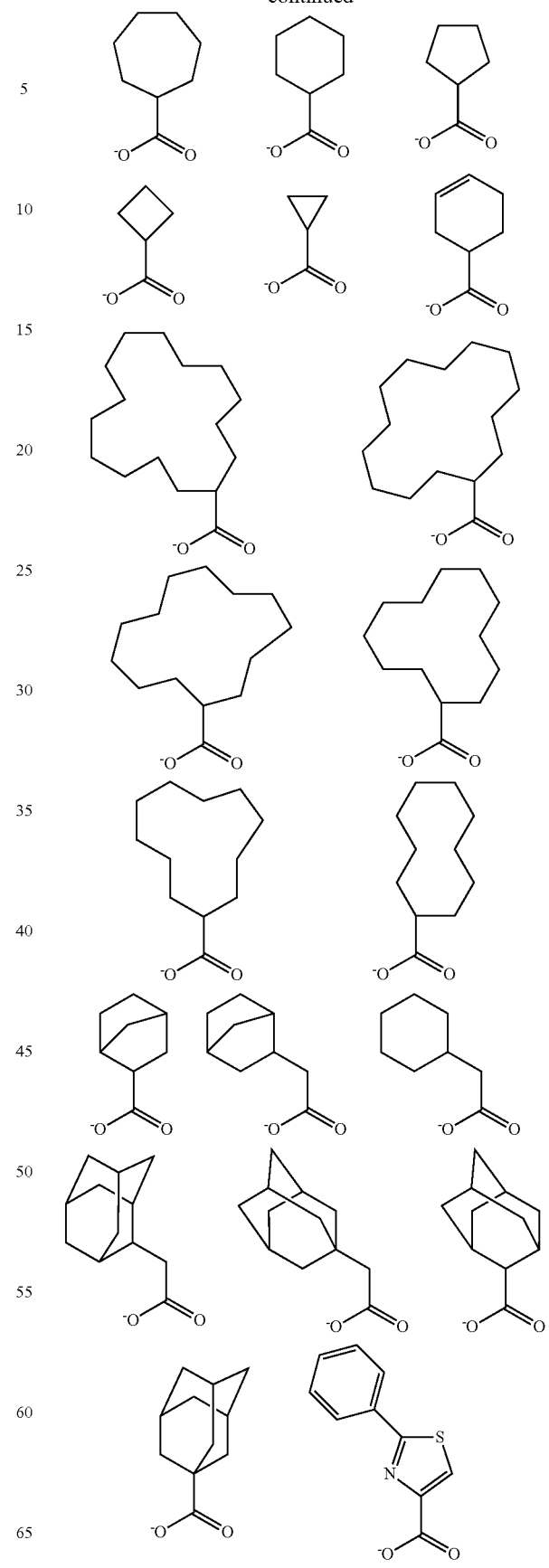

127
-continued
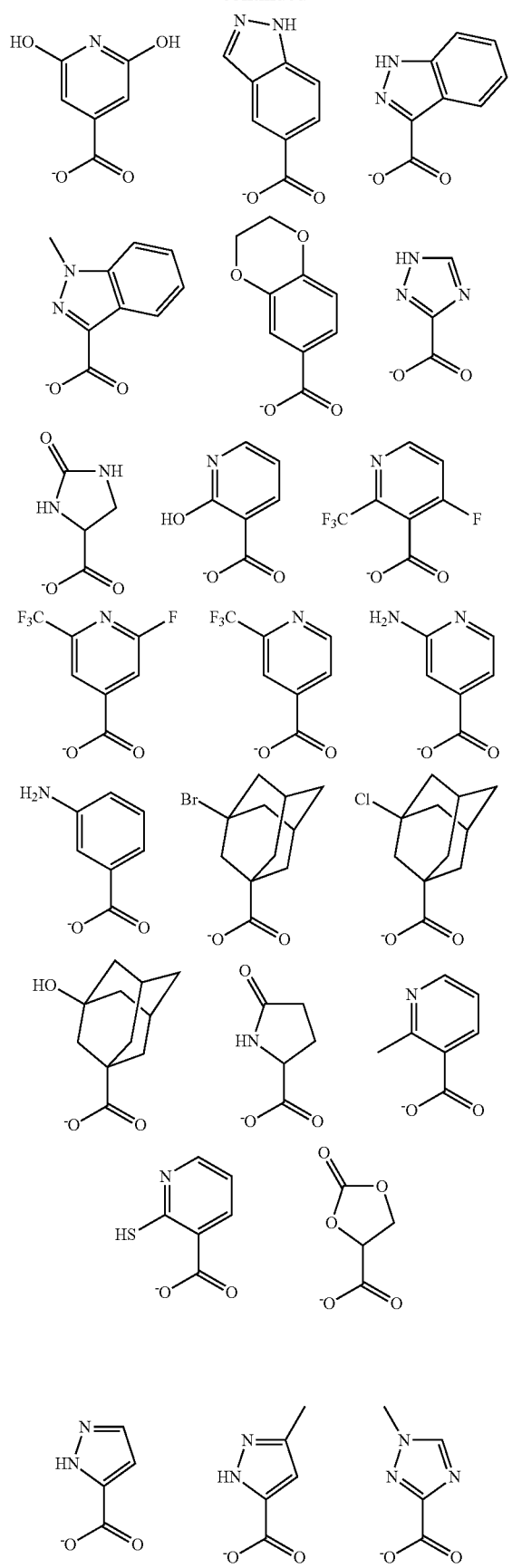
128
-continued
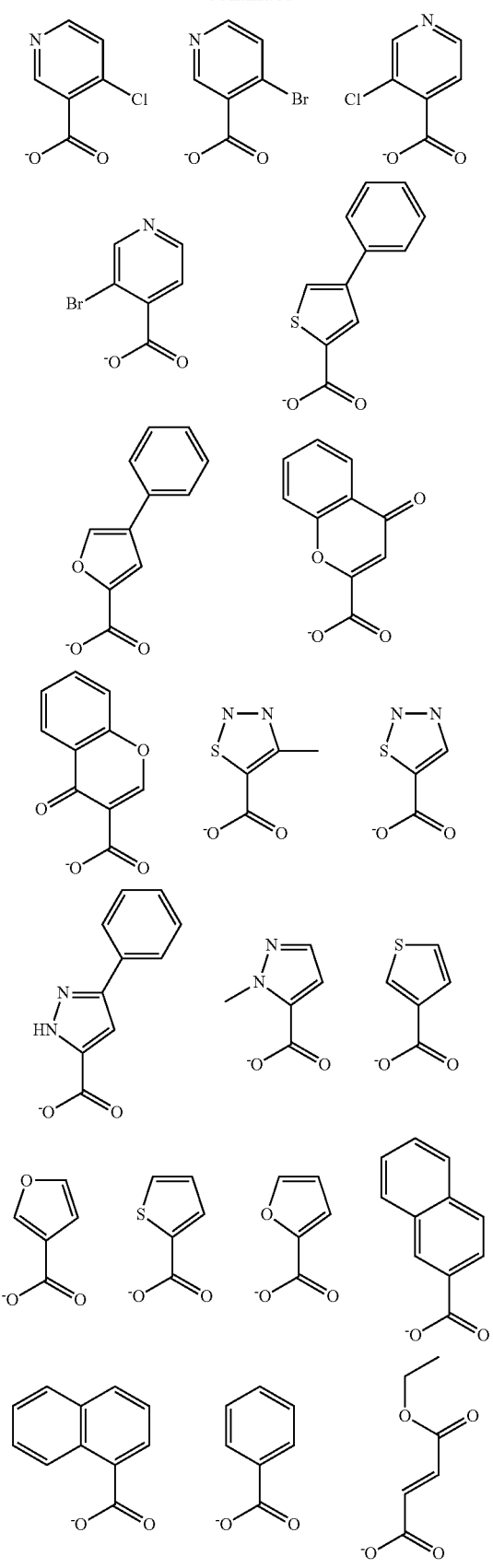

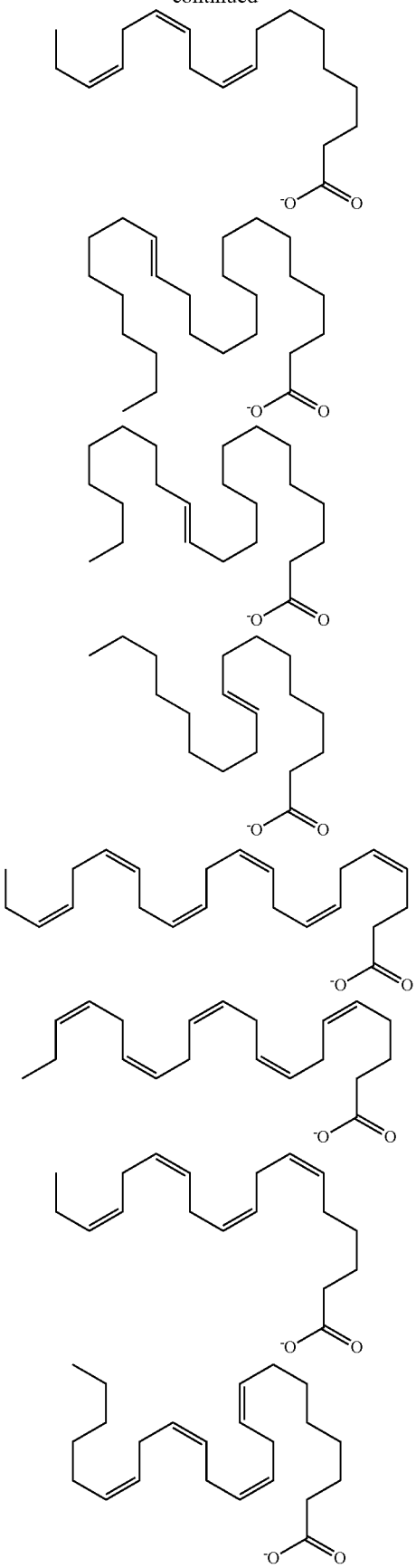
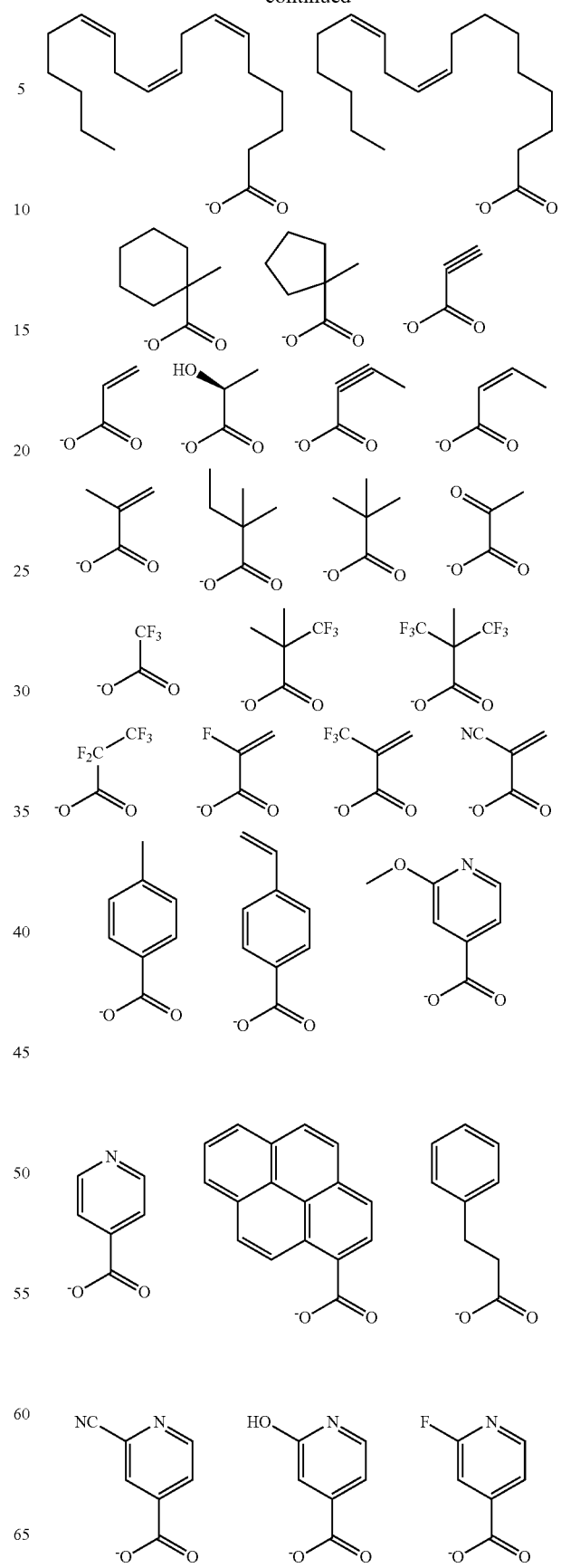

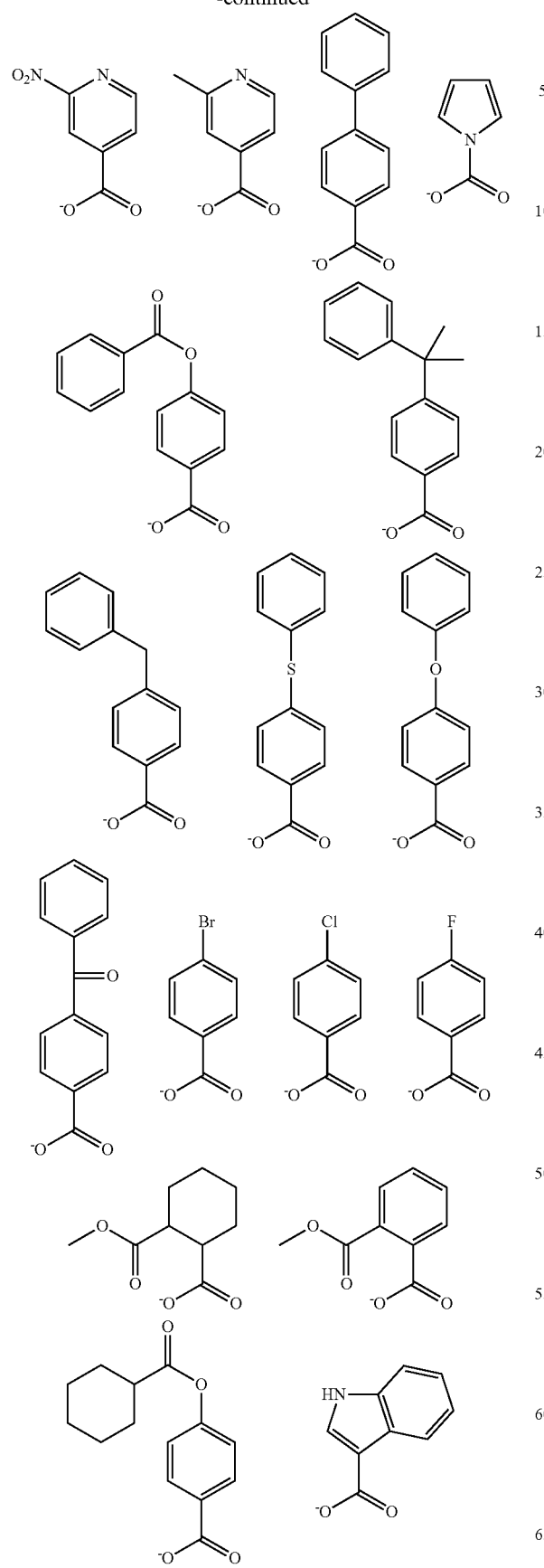
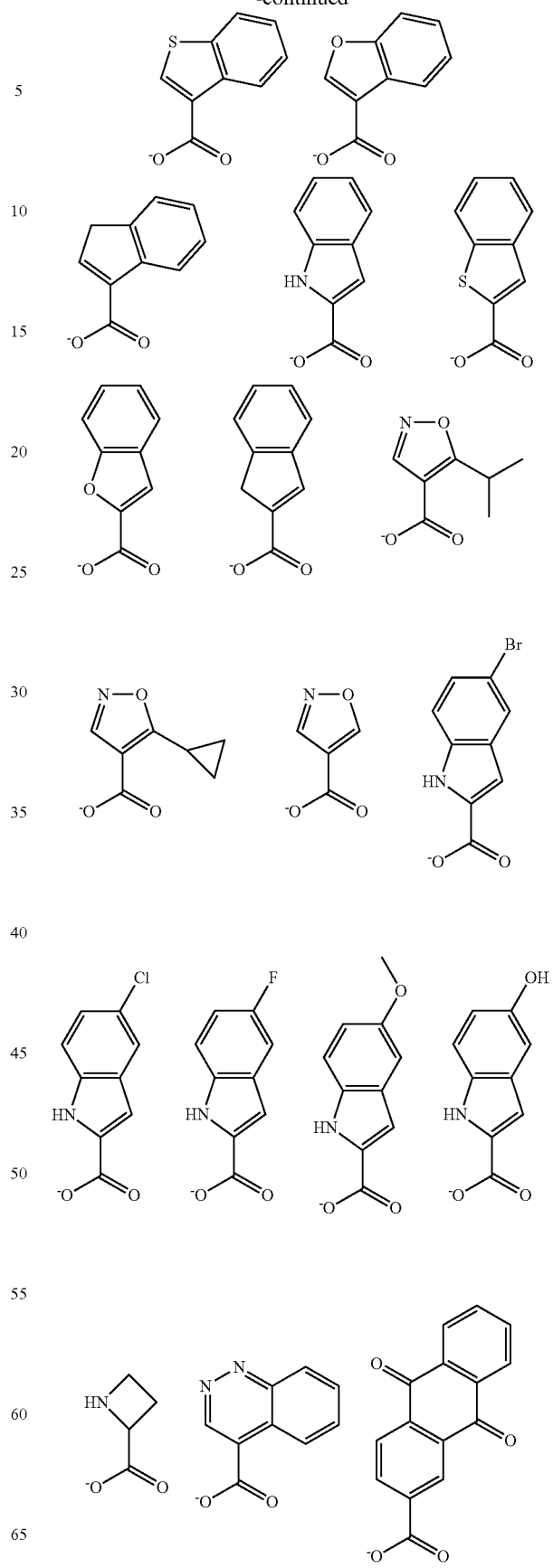

-continued
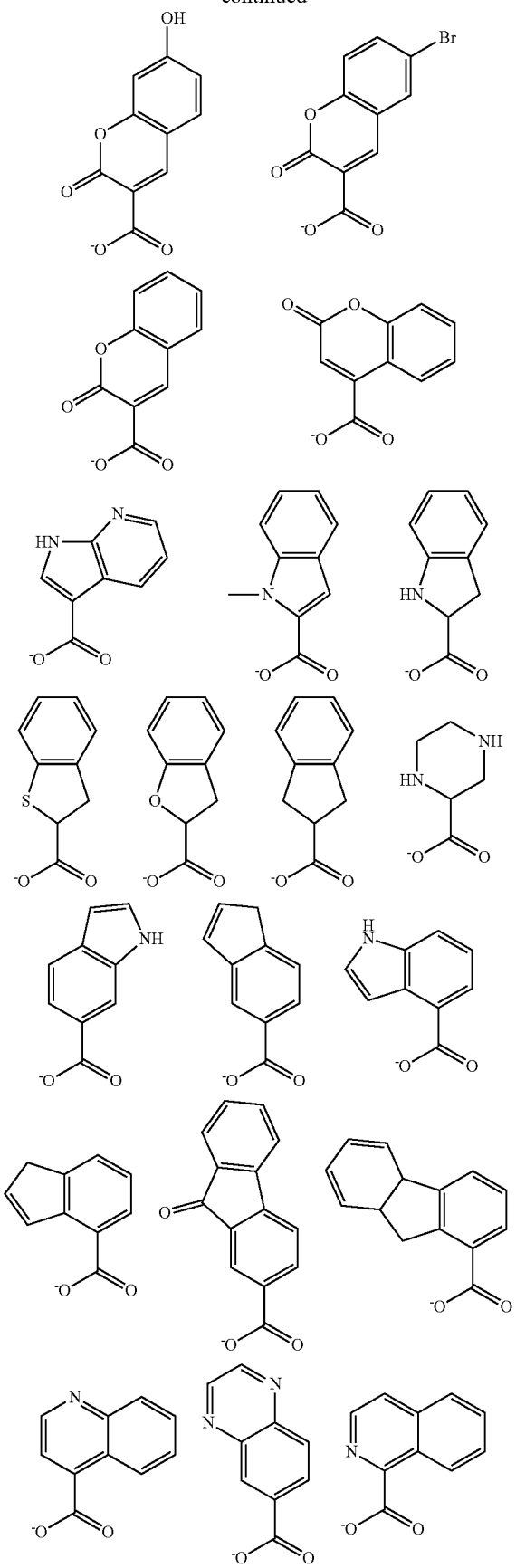
-continued
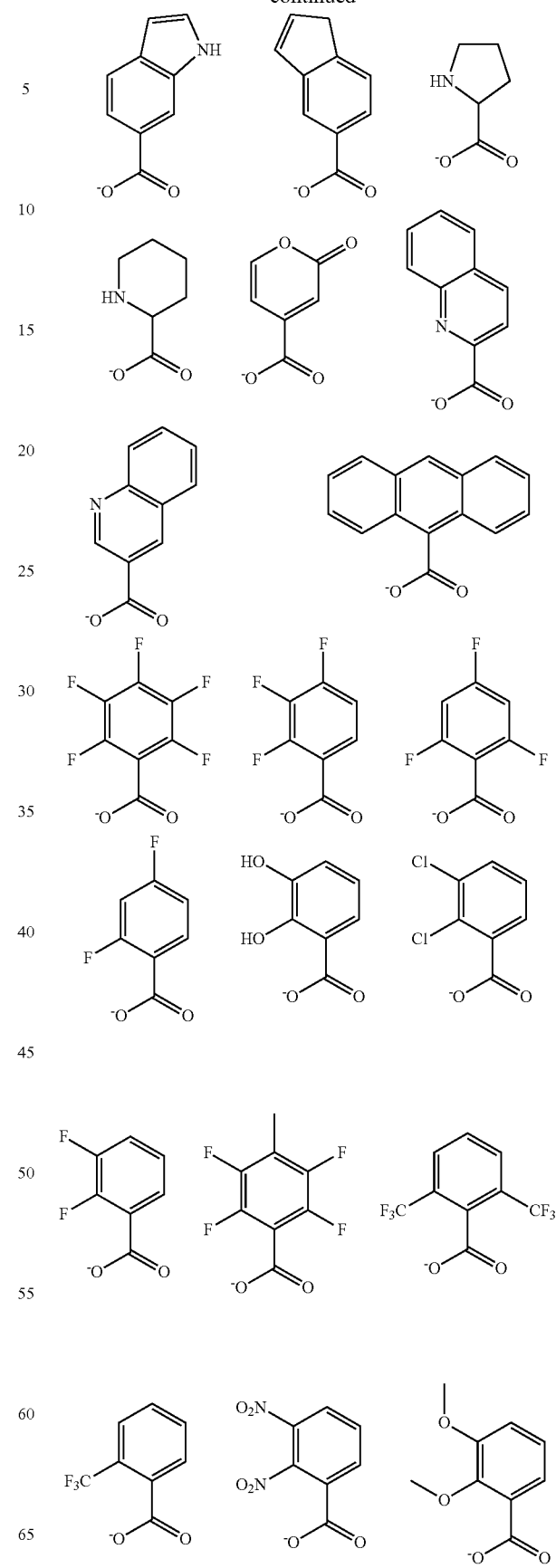

135
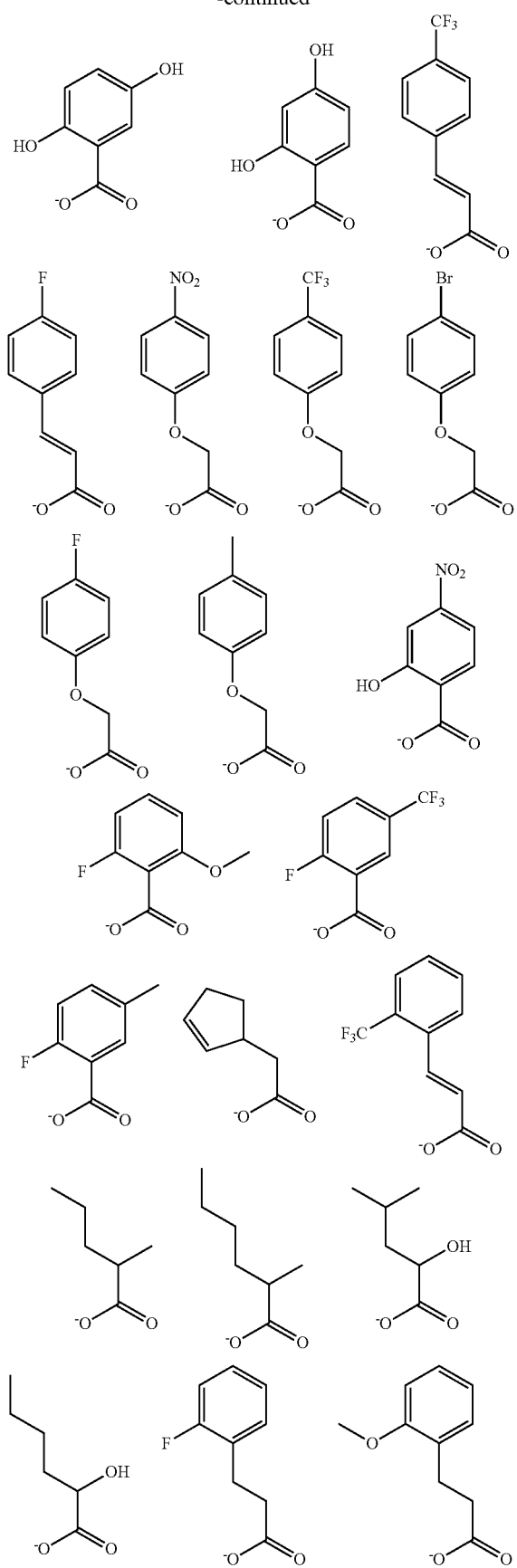
136
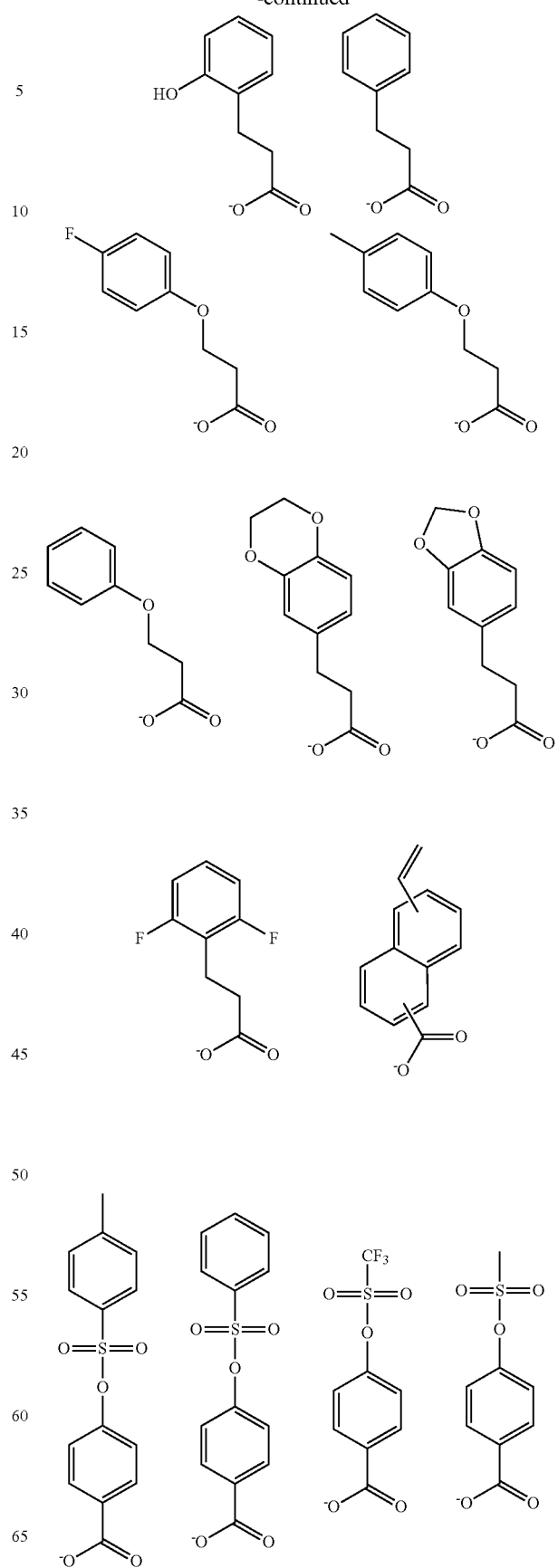

137
-continued
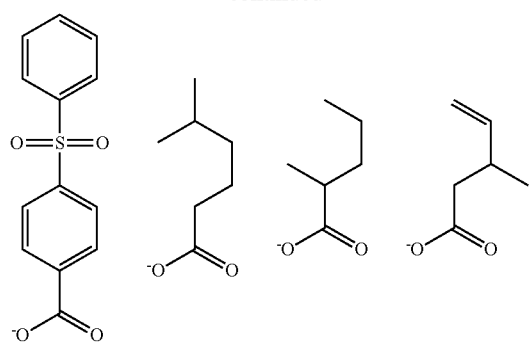
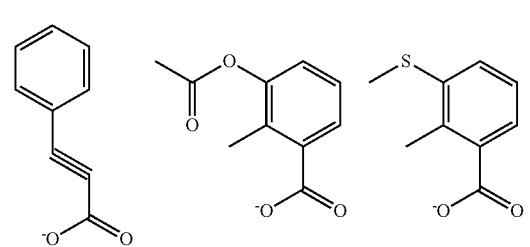
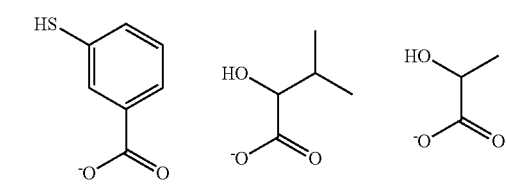
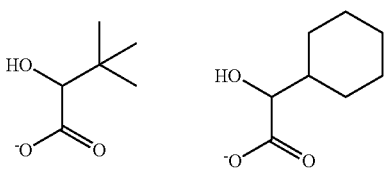
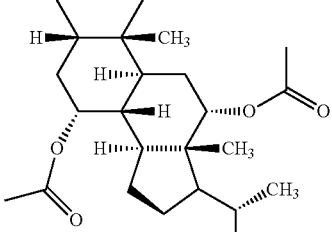
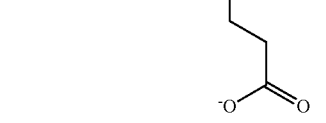
138
-continued
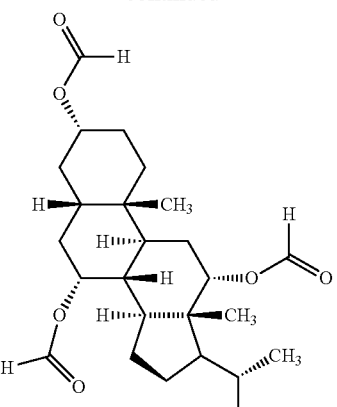
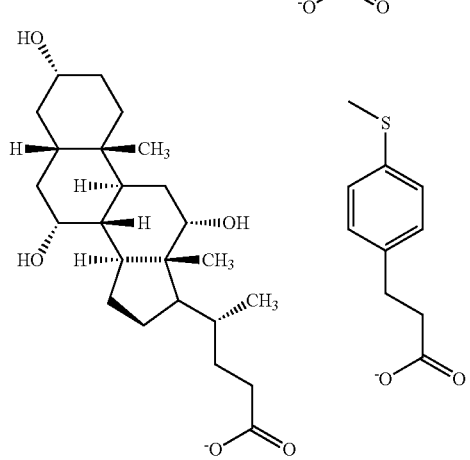
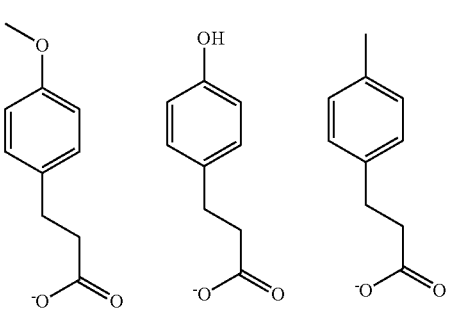
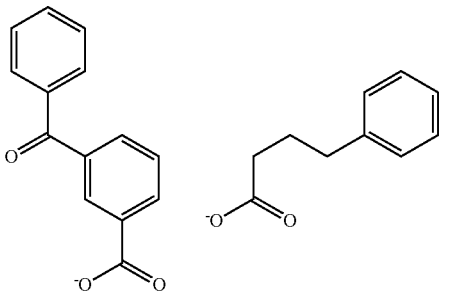

139
-continued
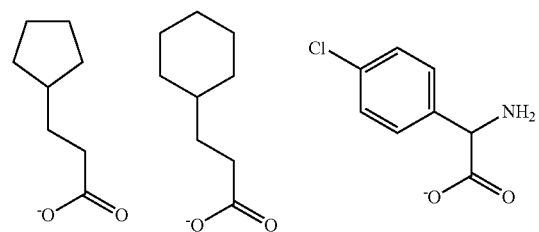
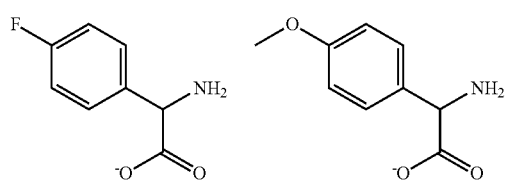
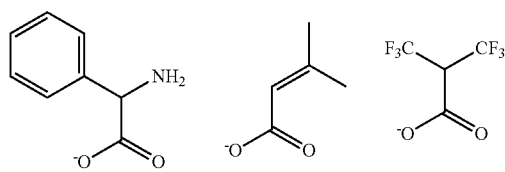
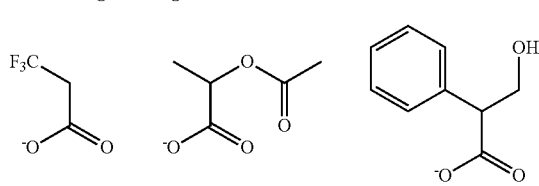
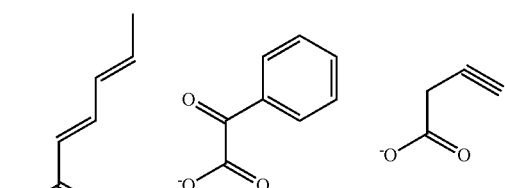
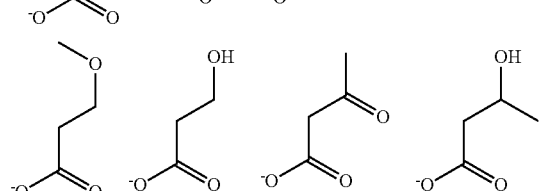
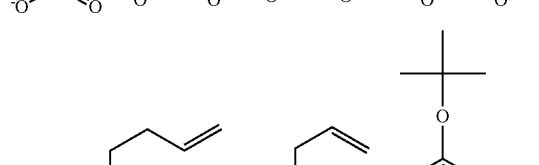
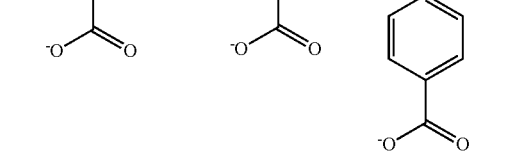
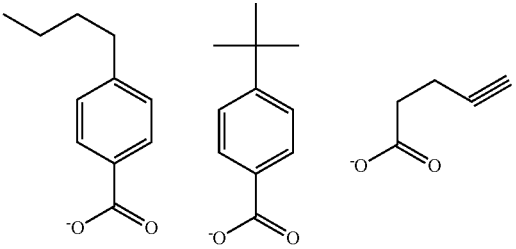
140
-continued
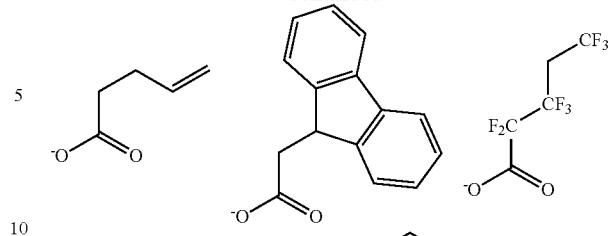
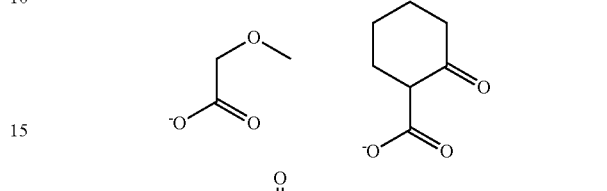
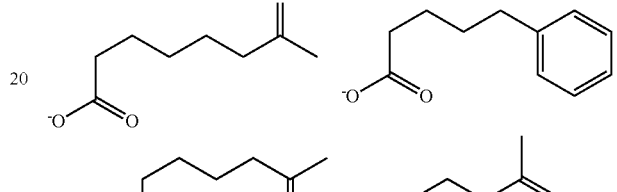
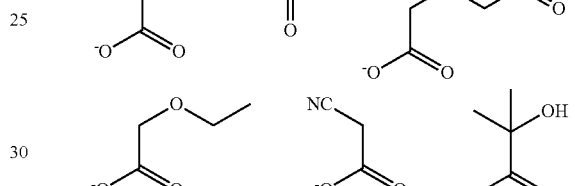
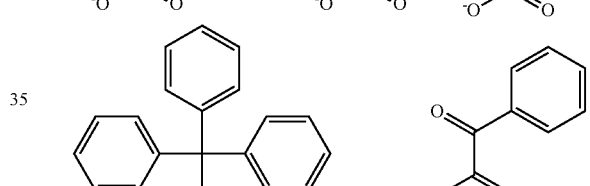
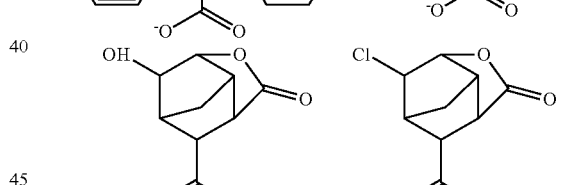
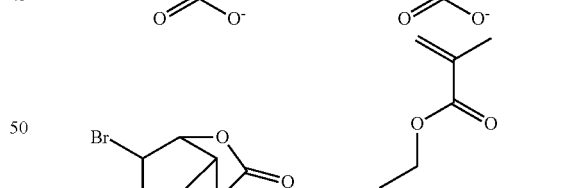
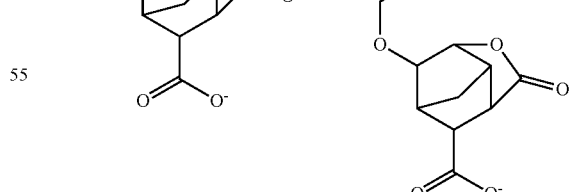
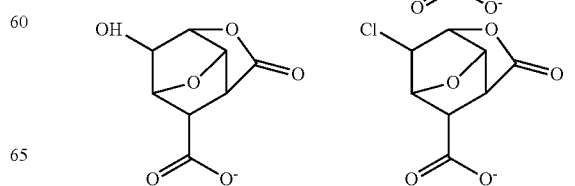

-continued

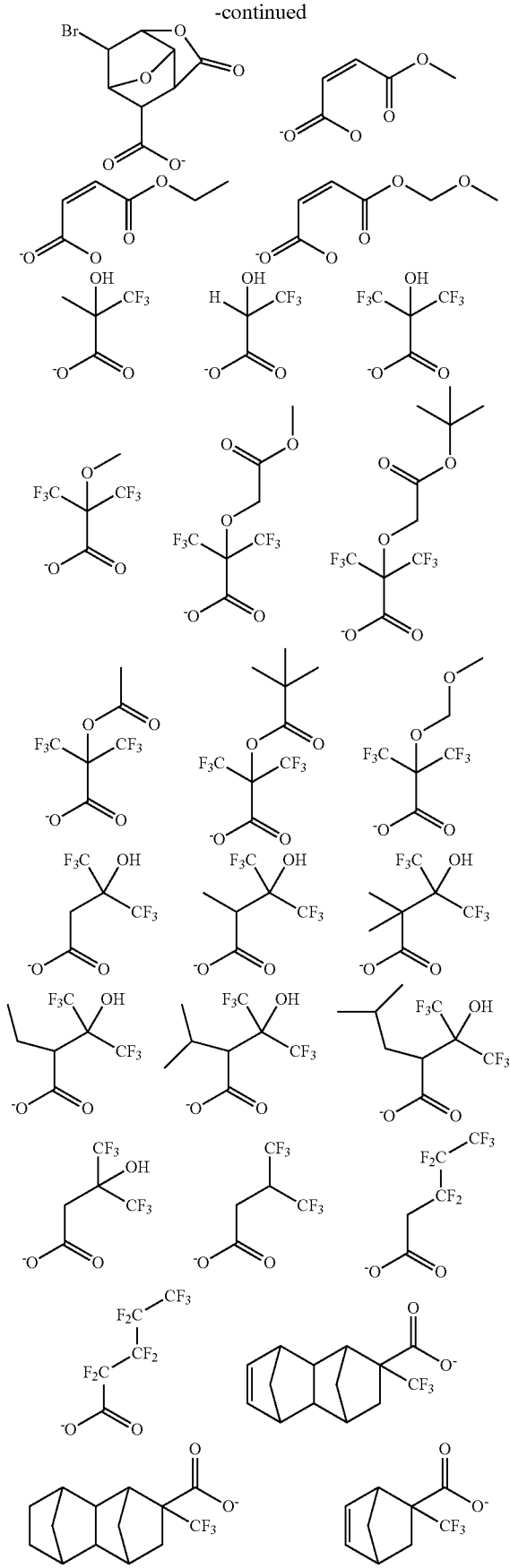

-continued

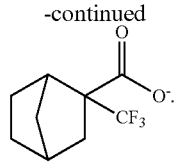

2. The resist composition of claim 1, further comprising an acid generator capable of generating sulfonic acid, sulfonimide or sulfonmethide.

3. The resist composition of claim 1, further comprising an organic solvent.

4. The resist composition of claim 1 wherein the base polymer comprises recurring units having the formula (a1) or recurring units having the formula (a2):

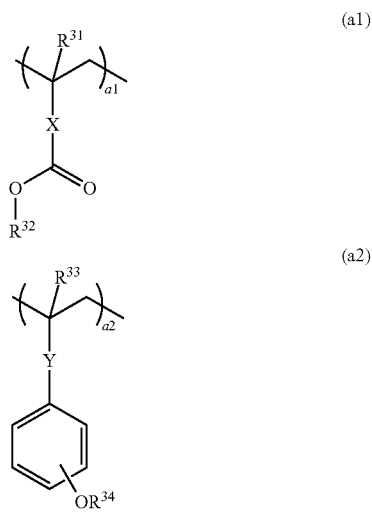

wherein $R^{31}$ and $R^{33}$ are each independently hydrogen or methyl, $R^{32}$ and $R^{34}$ are each independently an acid labile group, X is a single bond, ester group, phenylene group, naphthylene group or a $C_1$-$C_{12}$ linking group containing lactone ring, and Y is a single bond or ester group.

5. The resist composition of claim 4, further comprising a dissolution inhibitor.

6. The resist composition of claim 4 which is a chemically amplified positive resist composition.

7. The resist composition of claim 1 wherein the base polymer is free of an acid labile group.

8. The resist composition of claim 7, further comprising a crosslinker.

9. The resist composition of claim 7 which is a chemically amplified negative resist composition.

10. The resist composition of claim 1 wherein the base polymer comprises recurring units of at least one type selected from the formulae (f1) to (f3):

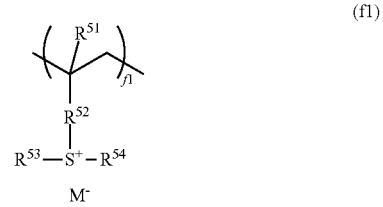

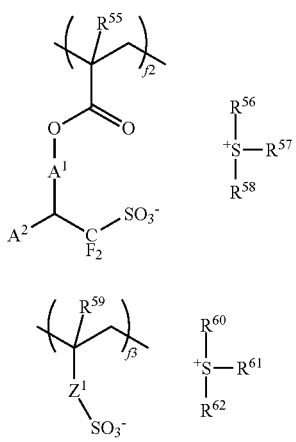

wherein $R^{51}$, $R^{55}$ and $R^{59}$ each are hydrogen or methyl, $R^{52}$ is a single bond, phenylene, —O—$R^{63}$—, or —C(=O)—$Y^1$—$R^{63}$—, $Y^1$ is —O— or —NH—, $R^{63}$ is a $C_1$-$C_6$ straight, branched or cyclic alkylene or alkenylene group which may contain a carbonyl, ester, ether or hydroxyl moiety, or phenylene group, $R^{53}$, $R^{54}$, $R^{56}$, $R^{57}$, $R^{58}$, $R^{60}$, $R^{61}$, and $R^{62}$ are each independently a $C_1$-$C_{12}$ straight, branched or cyclic alkyl group which may contain a carbonyl, ester or ether moiety, or a $C_6$-$C_{12}$ aryl group, $C_7$-$C_{20}$ aralkyl group or mercaptophenyl group, $A^1$ is a single bond, -$A^0$-C(=O)—O—, -$A^0$-O— or -$A^0$-O—C(=O)—, $A^0$ is a $C_1$-$C_{12}$ straight, branched or cyclic alkylene group which may contain a carbonyl, ester or ether moiety, $A^2$ is hydrogen or trifluoromethyl, $Z^1$ is a single bond, methylene, ethylene, phenylene, fluorinated phenylene, —O—$R^{64}$—, or —C(=O)—$Z^2$—$R^{64}$—, $Z^2$ is —O— or —NH—, $R^{64}$ is a $C_1$-$C_6$ straight, branched or cyclic alkylene or alkenylene group which may contain a carbonyl, ester, ether or hydroxyl moiety, or phenylene, fluorinated phenylene or trifluoromethyl-substituted phenylene group, $M^-$ is a non-nucleophilic counter ion, and f1, f2 and f3 are numbers in the range: $0 \leq f1 \leq 0.5$, $0 \leq f2 \leq 0.5$, $0 \leq f3 \leq 0.5$, and $0 < f1+f2+f3 \leq 0.5$.

11. The resist composition of claim 1, further comprising a surfactant.

12. A process for forming a pattern comprising the steps of applying the resist composition of claim 1 onto a substrate, baking to form a resist film, exposing the resist film to high-energy radiation, and developing the exposed film in a developer.

13. The process of claim 12 wherein the high-energy radiation is ArF excimer laser radiation of wavelength 193 nm or KrF excimer laser radiation of wavelength 248 nm.

14. The process of claim 12 wherein the high-energy radiation is electron beam or extreme ultraviolet radiation of wavelength 3 to 15 nm.

15. A resist composition comprising a base polymer and a phosphazene salt compound having the formula (A):

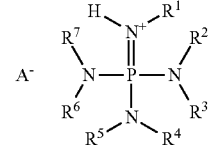

wherein $R^1$ to $R^7$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, which may contain an ester, ether, sulfide, sulfoxide, carbonate, carbamate, sulfone, halogen, amino, amide, hydroxy, thiol or nitro moiety, a pair of $R^1$ and $R^2$, $R^2$ and $R^3$, $R^3$ and $R^4$, $R^4$ and $R^5$, $R^5$ and $R^6$, or $R^6$ and $R^7$ may bond together to form a ring, or a pair of $R^2$ and $R^3$, $R^4$ and $R^5$, or $R^6$ and $R^7$, taken together, may form a double bond or a group having the formula (A)-1, $R^1$ may be a group having the formula (A)-2,

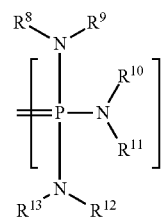

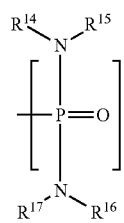

wherein $R^8$ to $R^{17}$ are each independently hydrogen, or a $C_1$-$C_{24}$ straight, branched or cyclic alkyl group, $C_2$-$C_{24}$ straight, branched or cyclic alkenyl group, $C_2$-$C_{24}$ straight, branched or cyclic alkynyl group, or $C_6$-$C_{20}$ aryl group, a pair of $R^8$ and $R^9$, $R^9$ and $R^{10}$, $R^{10}$ and $R^{11}$, $R^{11}$ and $R^{12}$, $R^{12}$ and $R^{13}$, $R^{14}$ and $R^{15}$, or $R^{16}$ and $R^{17}$ may bond together to form a ring, or a pair of $R^8$ and $R^9$, $R^{10}$ and $R^{11}$, or $R^{12}$ and $R^{13}$, taken together, may form a double bond or a group having the formula (A)-1, $A^-$ is an anion selected from the group consisting of hydroxide, chloride, bromide, iodide, nitrate, nitrite, chlorate, chlorite, perchlorate, hydrogencarbonate, dihydrogenphosphate, hydrogensulfate, thiocyanate, hydrogenoxalate, cyanide, iodate ions, and anions of the formulae (M-1) and (M-2):

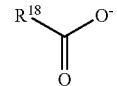

-continued (M)-2

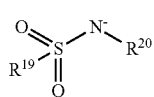

wherein $R^{18}$ is hydrogen, or a $C_1$-$C_{30}$ straight, branched or cyclic alkyl group, $C_2$-$C_{30}$ straight, branched or cyclic alkenyl group, $C_2$-$C_{30}$ straight, branched or cyclic alkynyl group, $C_6$-$C_{20}$ aryl group, or $C_7$-$C_{20}$ aralkyl group, which may contain an ester, ether, sulfide, sulfoxide, carbonate, carbamate, sulfone, halogen, amino, amide, hydroxy, thiol or nitro moiety, with the proviso that $R^{18}$ does not contain a group of the formula (A)-3:

(A)-3

wherein Ar is a $C_6$-$C_{16}$ aromatic group, $R^{21}$ and $R^{22}$ are each independently hydrogen, hydroxy, alkoxy, $C_1$-$C_6$ straight, branched or cyclic alkyl group, or $C_6$-$C_{10}$ aryl group, $R^{19}$ is fluorine, or a $C_1$-$C_{10}$ straight, branched or cyclic fluoroalkyl group or fluorophenyl group, which may contain a hydroxy, ether, ester or alkoxy moiety, $R^{20}$ is hydrogen, or a $C_1$-$C_{10}$ straight, branched or cyclic alkyl group, $C_2$-$C_{10}$ straight, branched or cyclic alkenyl group, $C_2$-$C_{10}$ straight or branched alkynyl group, or $C_6$-$C_{10}$ aryl group, which may contain a hydroxy, ether, ester or alkoxy moiety.

16. The resist composition of claim 15 wherein the base polymer comprises recurring units having the formula (a1) or recurring units having the formula (a2):

(a1)

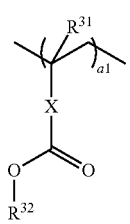

(a2)

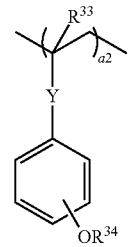

wherein $R^{31}$ and $R^{33}$ are each independently hydrogen or methyl, $R^{32}$ and $R^{34}$ are each independently an acid labile group, X is a single bond, ester group, phenylene group, naphthylene group or a $C_1$-$C_{12}$ linking group containing lactone ring, and Y is a single bond or ester group.

17. The resist composition of claim 16 which is a chemically amplified positive resist composition.

18. The resist composition of claim 15 wherein the base polymer is free of an acid labile group.

19. The resist composition of claim 18 which is a chemically amplified negative resist composition.

20. A process for forming a pattern comprising the steps of applying the resist composition of claim 15 onto a substrate, baking to form a resist film, exposing the resist film to high-energy radiation, and developing the exposed film in a developer.

\* \* \* \* \*